(12) United States Patent
Miller et al.

(10) Patent No.: US 7,667,054 B2
(45) Date of Patent: Feb. 23, 2010

(54) CYTOTOXIC AGENTS COMPRISING NEW TAXANES

(75) Inventors: Michael L. Miller, Framingham, MA (US); Ravi V. J. Chari, Newton, MA (US); Erkan Baloglu, Stoneham, MA (US); Alain Commercon, Vitry-sur-Seine (FR)

(73) Assignee: Aventis Pharma S.A., Antony (FR)

( * ) Notice: Subject to any disclaimer, the term of this patent is extended or adjusted under 35 U.S.C. 154(b) by 710 days.

(21) Appl. No.: 11/295,294

(22) Filed: Dec. 6, 2005

(65) Prior Publication Data

US 2006/0178427 A1  Aug. 10, 2006

(30) Foreign Application Priority Data

Dec. 7, 2004  (EP) .................. 04292898

(51) Int. Cl.
*C07D 305/00* (2006.01)
(52) U.S. Cl. ...................................... 549/510
(58) Field of Classification Search .................. 549/510
See application file for complete search history.

(56) References Cited

U.S. PATENT DOCUMENTS

| | | | |
|---|---|---|---|
| 5,728,849 A | 3/1998 | Bouchard et al. | |
| 6,340,701 B1 | 1/2002 | Chari et al. | |
| 6,372,738 B2 | 4/2002 | Chari et al. | |
| 6,436,931 B1 | 8/2002 | Chari et al. | |

FOREIGN PATENT DOCUMENTS

| | | |
|---|---|---|
| EP | 0 617 034 A1 | 9/1994 |
| WO | WO97/23473 | 7/1997 |
| WO | WO 01/38318 A1 | 5/2001 |
| WO | WO 03/097625 | 11/2003 |
| WO | WO 2004/013093 | 2/2004 |

OTHER PUBLICATIONS

Miller et al, Synthesis of Potent Taxoids for Tumor-specific Delivery Using Monoclonal Antibodies, Bioorganic & Medicinal Chemistry Letters 14 (2004) 4079-4082.

Miller et al, Synthesis of Taxoids with Improved Cytotoxicity and Solubility for Use in Tumor-Specific Delivery, J. Med. Chem, 2004, 47, 4802-4805.

Ojima et al, Tumor-Specific Novel Taxoid-Monoclonal Antibody Conjugates, J. Med. Chem. 2002, 45, 5620-5623.

*Primary Examiner*—Janet L. Andres
*Assistant Examiner*—Raymond Covington
(74) *Attorney, Agent, or Firm*—Paul R. Darkes

(57) ABSTRACT

The invention relates to novel cytotoxic agents comprising taxanes and their therapeutic use as a result of delivering the taxanes to a specific cell population in a targeted fashion by chemically linking the taxane to a cell binding agent.

48 Claims, 2 Drawing Sheets

Fig. 1 Relative binding affinities of huC242 antibody and its taxoid conjugate huC242-IGT-15-075
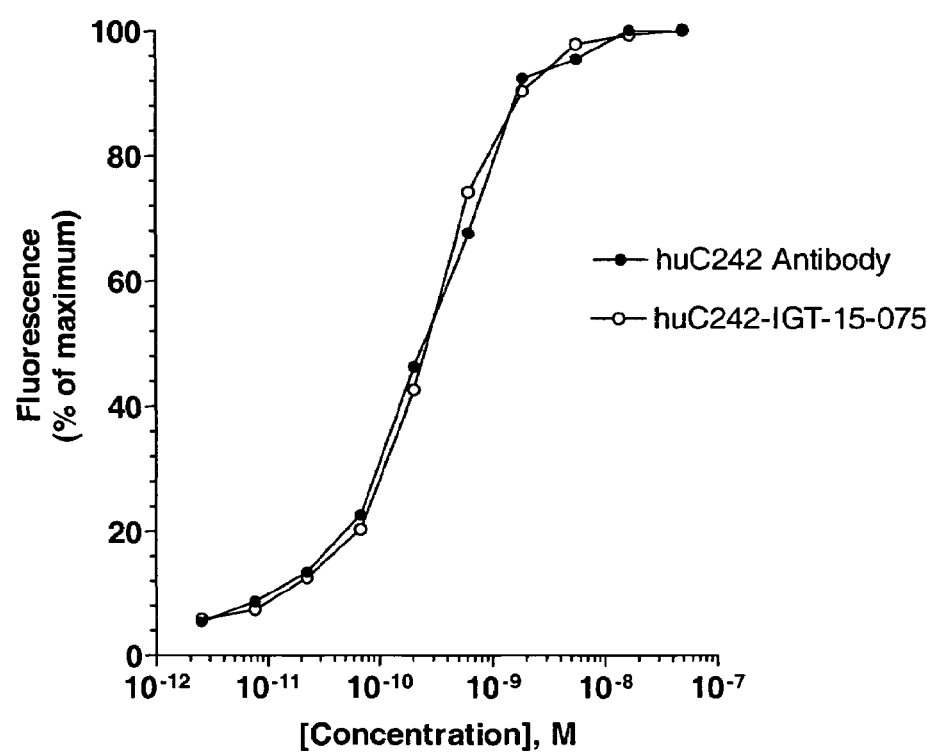

Fig. 2a In vitro potency of huC242-Txaxid IGT-15-075 towards antigen positive COLO 205 cells and antigen negative A-375 cells.
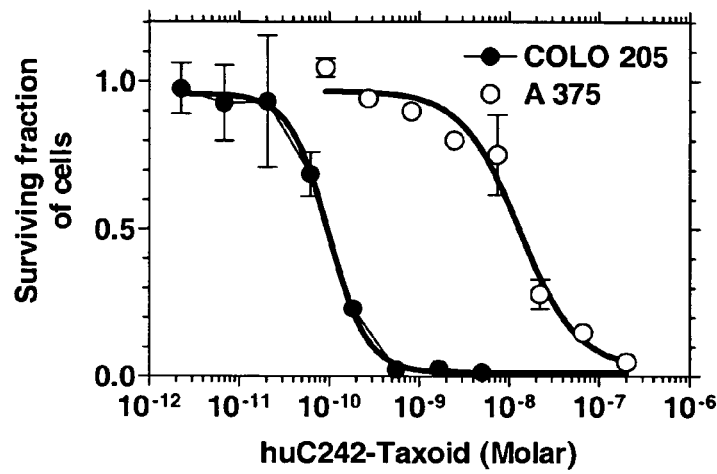
Fig. 2b In vitro potency of free Taxoid IGT-15-075 towards COLO 205 and A-375 cells.
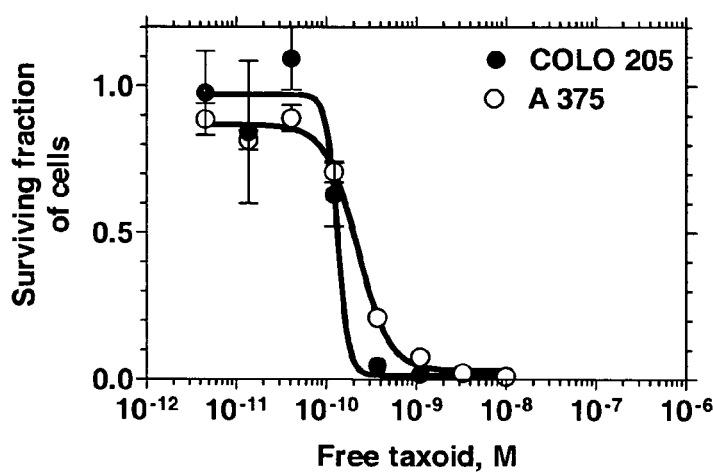

CYTOTOXIC AGENTS COMPRISING NEW TAXANES

FIELD OF THE INVENTION

The present invention relates to novel cytotoxic agents and their therapeutic use. More specifically, the invention relates to novel cytotoxic agents comprising taxanes and their therapeutic use. These novel cytotoxic agents have therapeutic use as a result of delivering the taxanes to a specific cell population in a targeted fashion by chemically linking the taxane to a cell binding agent.

BACKGROUND OF THE INVENTION

Many reports have appeared on the attempted specific targeting of tumor cells with monoclonal antibody-drug conjugates (Sela et al, in *Immunoconjugates* 189-216 (C. Vogel, ed. 1987); Ghose et al, in *Targeted Drugs* 1-22 (E. Goldberg, ed. 1983); Diener et al, in *Antibody mediated delivery systems* 1-23 (J. Rodwell, ed. 1988); Pietersz et al, in *Antibody mediated delivery systems* 25-53 (J. Rodwell, ed. 1988); Bumol et al, in *Antibody mediated delivery systems* 55-79 (J. Rodwell, ed. 1988). All references and patents cited herein are incorporated by reference.

Cytotoxic drugs such as methotrexate, daunorubicin, doxorubicin, vincristine, vinblastine, melphalan, mitomycin C, and chlorambucil have been conjugated to a variety of murine monoclonal antibodies. In some cases, the drug molecules were linked to the antibody molecules through an intermediary carrier molecule such as serum albumin (Garnett et al, 46 *Cancer Res.* 2407-2412 (1986); Ohkawa et al 23 *Cancer Immunol. Immunother.* 81-86 (1986); Endo et al, 47 *Cancer Res.* 1076-1080 (1980)), dextran (Hurwitz et al, 2 *Appl. Biochem.* 25-35 (1980); Manabi et al, 34 *Biochem. Pharmacol.* 289-291 (1985); Dillman et al, 46 *Cancer Res.* 4886-4891 (1986); Shoval et al, 85 *Proc. Natl. Acad. Sci.* 8276-8280 (1988)), or polyglutamic acid (Tsukada et al, 73 *J. Natl. Canc. Inst.* 721-729 (1984); Kato et al 27 *J. Med. Chem.* 1602-1607 (1984); Tsukada et al, 52 *Br. J. Cancer* 111-116 (1985)).

A wide array of linker technologies has been employed for the preparation of such immunoconjugates and both cleavable and non-cleavable linkers have been investigated. In most cases, the full cytotoxic potential of the drugs could only be observed, however, if the drug molecules could be released from the conjugates in unmodified form at the target site.

One of the cleavable linkers that has been employed for the preparation of antibody-drug conjugates is an acid-labile linker based on cis-aconitic acid that takes advantage of the acidic environment of different intracellular compartments such as the endosomes encountered during receptor mediated endocytosis and the lysosomes. Shen and Ryser introduced this method for the preparation of conjugates of daunorubicin with macromolecular carriers (102 *Biochem. Biophys. Res. Commun.* 1048-1054 (1981)). Yang and Reisfeld used the same technique to conjugate daunorubicin to an anti-melanoma antibody (80 *J. Natl. Canc. Inst.* 1154-1159 (1988)). Dillman et al. also used an acid-labile linker in a similar fashion to prepare conjugates of daunorubicin with an anti-T cell antibody (48 *Cancer Res.* 6097-6102 (1988)).

An alternative approach, explored by Trouet et al, involved linking daunorubicin to an antibody via a peptide spacer arm (79 *Proc. Natl. Acad. Sci.* 626-629 (1982)). This was done under the premise that free drug could be released from such a conjugate by the action of lysosomal peptidases.

In vitro cytotoxicity tests, however, have revealed that antibody-drug conjugates rarely achieved the same cytotoxic potency as the free unconjugated drugs. This suggested that mechanisms by which drug molecules are released from the antibodies are very inefficient. In the area of immunotoxins, conjugates formed via disulfide bridges between monoclonal antibodies and catalytically active protein toxins were shown to be more cytotoxic than conjugates containing other linkers. See, Lambert et al, 260 *J. Biol. Chem.* 12035-12041 (1985); Lambert et al, in *Immunotoxins* 175-209 (A. Frankel, ed. 1988); Ghetie et al, 48 *Cancer Res.* 2610-2617 (1988). This was attributed to the high intracellular concentration of glutathione contributing to the efficient cleavage of the disulfide bond between an antibody molecule and a toxin. Despite this, there are only a few reported examples of the use of disulfide bridges for the preparation of conjugates between drugs and macromolecules. Shen et al (260 *J. Biol. Chem.* 10905-10908 (1985)) described the conversion of methotrexate into a mercaptoethylamide derivative followed by conjugation with poly-D-lysine via a disulfide bond. Another report described the preparation of a conjugate of the trisulfide containing toxic drug calicheamycin with an antibody (Hinman et al., 53 *Cancer Res.* 3336-3342 (1993)).

One reason for the lack of disulfide linked antibody-drug conjugates is the unavailability of cytotoxic drugs possessing a sulfur atom containing moiety that can be readily used to link the drug to an antibody via a disulfide bridge. Furthermore, chemical modification of existing drugs is difficult without diminishing their cytotoxic potential.

Another major drawback with existing antibody-drug conjugates is their inability to deliver a sufficient concentration of drug to the target site because of the limited number of targeted antigens and the relatively moderate cytotoxicity of cancerostatic drugs like methotrexate, daunorubicin, and vincristine. In order to achieve significant cytotoxicity, linkage of a large number of drug molecules, either directly to the antibody or through a polymeric carrier molecule, becomes necessary. However, such heavily modified antibodies often display impaired binding to the target antigen and fast in vivo clearance from the blood stream.

In spite of the above described difficulties, useful cytotoxic agents comprising cell binding moieties and the group of cytotoxic drugs known as maytansinoids have been reported (U.S. Pat. No. 5,208,020, U.S. Pat. No. 5,416,064, and R. V. J. Chari, 31 *Advanced Drug Delivery Reviews* 89-104 (1998)). Similarly, useful cytotoxic agents comprising cell binding moieties and analogues and derivatives of the potent antitumor antibotic CC-1065 have also been reported (U.S. Pat. No. 5,475,092 and U.S. Pat. No. 5,585,499).

Paclitaxel (Taxol), a cytotoxic natural product, and docetaxel (Taxotere), a semi-synthetic derivative, are widely used in the treatment of cancer. These compounds belong to the family of compounds called taxanes. Taxanes are mitotic spindle poisons that inhibit the depolymerization of tubulin, resulting in an increase in the rate of microtubule assembly and cell death. While docetaxel and paclitaxel are useful agents in the treatment of cancer, their antitumor activity is limited because of their non-specific toxicity towards abnormal cells.

Further, compounds like paclitaxel and docetaxel themselves are not sufficiently potent to be used in conjugates of cell binding agents. Recently, a few new docetaxel analogs with greater potency than either docetaxel or paclitaxel have been described (Ojima et al., 39, *J. Med. Chem.* 3889-3896 (1996)). However, these compounds lack a suitable functionality that allows linkage via a cleavable bond to cell binding agents.

Accordingly, a method of treating diseases with taxanes wherein their side effects are reduced without compromising their cytotoxicity is greatly needed.

U.S. Pat. No. 6,436,931, U.S. Pat. No. 6,372,738 and U.S. Pat. No. 6,340,701 described taxanes linked by a disulfide bridge to the monoclonal antibody. Those taxanes seem to be not sufficiently potent to be used.

SUMMARY OF THE INVENTION

As disclosed in a first embodiment, one object of the present invention is to provide taxanes that are highly toxic and that can still be effectively used in the treatment of many diseases.

Another object of the present invention is to provide novel taxanes.

These and other objects have been achieved by providing a cytotoxic agent comprising one or more taxanes linked to a cell binding agent.

In a second embodiment, the present invention provides a therapeutic composition comprising:

(A) an effective amount of one or more taxanes linked to a cell binding agent, and (B) a pharmaceutically acceptable carrier, diluent, or excipient In a third embodiment, the present invention provides a method of killing selected cell populations comprising contacting target cells or tissue containing target cells, with a cytotoxic amount of a cytotoxic agent comprising one or more taxanes linked to a cell binding agent.

BRIEF DESCRIPTION of the DRAWINGS

FIG. 1 shows the relative binding affinities of huC242 antibody and its taxoid conjugate huC242 IGT-15-075.

FIG. 2a shows the in vitro potency of huC242-Taxoid IGT-15-075 towards antigen positive COLO 205 cells and antigen negative A-375 cells.

FIG. 2b show the in vitro potence of free Taxoid IGT-15-075 towards COLO 205 and A-375 cells.

DETAILED DESCRIPTION OF THE INVENTION

This invention is based on the synthesis of novel taxanes that retain high cytotoxicity and that can be effectively linked to cell binding agents. It has previously been shown that the linkage of highly cytotoxic drugs to antibodies using a cleavable link, such as a disulfide bond, ensures the release of fully active drugs inside the cell, and such conjugates are cytotoxic in an antigen specific manner (U.S. Pat. No. 6,340,701; U.S. Pat. No. 6,372,738; U.S. Pat. No. 6,436,931). However, the art reveals that it is extremely difficult to modify existing drugs without diminishing their cytotoxic potential. The disclosed invention overcomes this problem by modifying the disclosed taxanes with chemical moieties. As a result, the disclosed novel taxanes preserve, and in some cases could even enhance, the cytotoxic potency of known taxanes. The cell binding agent-taxane complexes permit the full measure of the cytotoxic action of the taxanes to be applied in a targeted fashion against unwanted cells only, therefore, avoiding side effects due to damage to non-targeted healthy cells. Thus, the invention provides useful agents for the elimination of diseased or abnormal cells that are to be killed or lysed such as tumor cells (particularly solid tumor cells).

The cytotoxic agent according to the present invention comprises one or more taxanes linked to a cell binding agent via a linking group. The linking group is part of a chemical moiety that is covalently bound to a taxane through conventional methods. In a preferred embodiment, the chemical moiety can be covalently bound to the taxane via an ester linkage.

The taxanes useful in the present invention have the formula (I) shown below:

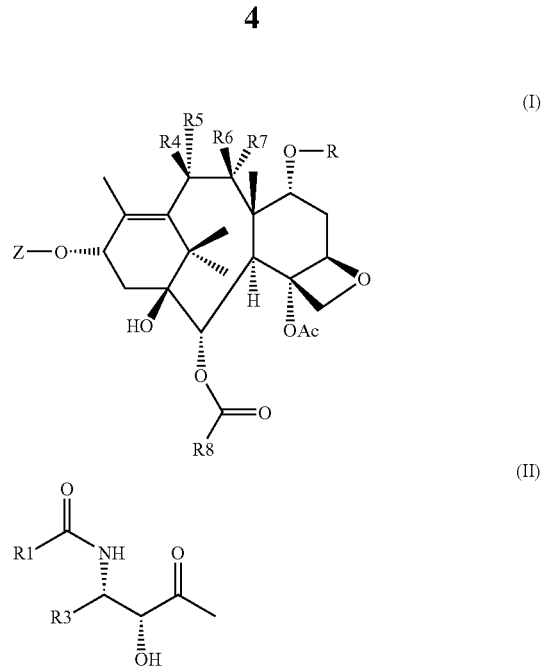

Z=H or a radical of formula II $R_1$ is a linker or an optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms, —$OR_2$ or a carbamate formed from any of said alkyl having from 1 to 10 carbon atoms, alkenyl or alkynyl having from 2 to 10 carbon atoms, cycloalkyl or cycloalkenyl having from 3 to 10 carbon atoms, or optionally substituted aryl or heterocyclyl radical. Preferably $R_1$ is —$OR_2$ or an optionally substituted aryl or heterocyclic radical $R_2$ is an alkyl radical having from 1 to 10 carbon atoms, alkenyl or alkynyl having from 2 to 10 carbon atoms, cycloalkyl or cycloalkenyl having from 3 to 10 carbon atoms, optionally substituted aryl or heterocyclic radical. Preferably $R_2$ is an alkyl group and more preferably a substituted alkyl group such as a terbutyl group.

$R_3$ is a linker or an optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms $R_4$ is a linker, H, a hydroxy radical, an alkoxy, an alkenyloxy, an optionally substituted alkanoyloxy, aroyloxy, alkenoyloxy, alkynoyloxy, cycloalkanoyloxy, alkoxyacetyl, alkylthioacetyl, alkyloxycarbonyloxy, cycloalkyloxy, cycloalkenyloxy, carbamoyloxy, alkylcarbamoyloxy, or dialkylcarbamoyloxy, a heterocyclic or aryl ether, ester or carbamate, or, a linear, branched, or cyclic alkyl or alkenyl ester or ether having from 1 to 10 carbon atoms or a carbamate of the formula —OCOX, wherein X is a nitrogen-containing heterocycle such as unsubstituted or substituted piperidino, morpholino, piperazino, N-methylpiperazino, or a carbamate of the formula —$OCONR_9R_{10}$, wherein $R_9$ and $R_{10}$ are the same or different and are H, linear, branched, or cyclic alkyl having from 1 to 10 atoms or unsubstituted or substituted aryl having from 1 to 10 carbon atoms. Preferably $R_4$ is a linker or an alkanoyloxy radical.

$R_5$ or $R_7$ is H $R_6$ is H $R_7$ or $R_5$ and R form a bond (cyclic ether)

$R_8$=optionally substituted aryl or heterocyclic radical

The present invention will be more completely described with its 3 major embodiments.

Embodiment 1: $R_4$ is the linker

Z

=H or radical of formula II $R_1$ is an optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms, —$OR_2$ or a carbamate formed from any of said alkyl having from 1 to 10 carbon atoms, alkenyl or alkynyl having from 2 to 10 carbon atoms, cycloalkyl or cycloalkenyl having from 3 to 10 carbon atoms, or optionally substituted aryl or heterocyclyl radical $R_2$ is alkyl having from 1 to 10 carbon atoms, alkenyl or alkynyl having from 2 to 10 carbon atoms, cycloalkyl or cycloalkenyl having from 3 to 10 carbon atoms, optionally substituted aryl or heterocyclic radical Preferably, $R_1$ is t-butoxy, crotyl, dimethylacrylyl, isobutenyl, hexenyl, cyclopentenyl, cyclohexenyl, furyl, pyrollyl, thienyl, thiazolyl, imidazolyl, pyridyl, morpholino, piperidino, piperazino, oxazolyl, indolyl, benzofuranyl or benzothienyl.

More preferably, $R_1$ is t-butoxy, isobutenyl, crotyl, dimethyacrylyl, thienyl, thiazolyl or furyl $R_3$ is optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms Preferably, $R_3$ is crotyl, dimethylacrylyl, propenyl, isobutenyl, hexenyl, cyclopentenyl, cyclohexenyl, furyl, pyrollyl, thienyl, thiazolyl, pyridyl, oxazolyl, indolyl, benzofuranyl or benzothienyl.

More preferably, $R_3$ is iso-butenyl, crotyl, dimethacrylyl, thienyl, thiazolyl, pyridyl, tert-butyl, or furyl.

$R_4$ is the linking group.

Suitable linking groups are well known in the art and include disulfide groups, thioether groups, acid labile groups, photolabile groups, peptidase labile groups and esterase labile groups. Preferred are disulfide groups and thioether groups.

When the linking group is a thiol- or disulfide-containing group, the side chain carrying the thiol or disulfide group can be linear or branched, aromatic or heterocyclic. One of ordinary skill in the art can readily identify suitable side chains.

Specific examples of the thiol- or disulfide-containing substituents include —O(CR$_{13}$R$_{14}$)$_m$(CR$_{15}$R$_{16}$)$_n$(OCH$_2$CH$_2$)$_y$SZ', —OCO(CR$_{13}$R$_{14}$)$_m$(CR$_{15}$R$_{16}$)$_n$(OCH$_2$CH$_2$)$_y$SZ', —O(CR$_{13}$R$_{14}$)$_m$(CR$_{17}$=CR$_{18}$)(CR$_{15}$R$_{16}$)$_m$(OCH$_2$CH$_2$)$_y$ SZ', —OCO—(CR$_{13}$R$_{14}$)$_m$(CR$_{17}$=CR$_{18}$)(CR$_{15}$R$_{16}$)$_m$ (OCH$_2$CH$_2$)$_y$SZ', —OCONR$_{12}$(CR$_{13}$R$_{14}$)$_m$(CR$_{15}$R$_{16}$)$_n$ (OCH$_2$CH$_2$)$_y$SZ', —OCO-phenyl-X'SZ', —OCO-furyl-X'SZ', —OCO-oxazolyl-X'SZ', —OCO-thiazolyl-X'SZ', —OCO-thienyl-X'SZ', —OCO-imidazolyl-X'SZ', —OCO-morpholino-X'SZ', —OCO-piperazino-X'SZ', —OCO-piperidino-X'SZ', and —OCO—N-methylpiperazino-X'SZ', or —OCO—N-methylpiperazino-X'SZ', wherein:

Z' is H, a thiol protective group or SR', wherein X' is a direct link or a linear alkyl or branched alkyl having from 1-10 carbon atoms or a polyethylene glycol spacer with 2 to 20 repeating ethylene oxy units;

R' and $R_{12}$ are the same or different and are linear alkyl, branched alkyl or cyclic alkyl having from 1 to 10 carbon atoms, or simple or substituted aryl or heterocyclic, and $R_{12}$ can in addition be H, $R_{13}$, $R_{14}$, $R_{15}$ and $R_{16}$ are the same or different and are H or a linear or branched alkyl having from 1 to 4 carbon atoms, $R_{17}$ and $R_{18}$ are H or alkyl, n is an integer of 1 to 10, m is an integer from 1 to 10 and can also be 0, y is an integer from 1 to 20 and can also be 0.

$R_5$ or $R_7$ is H $R_6$ is H $R_7$ or $R_5$ and R form a bond (cyclic ether)

$R_8$ is an optionally substituted aryl or heterocyclic radical

Preferably, $R_8$ is 3-methoxyphenyl, 3-chlorophenyl, 2,5-dimethoxyphenyl, furyl, pyrollyl, thienyl, thiazolyl, imidazolyl, pyridyl, indolyl, oxazolyl, benzofuranyl or benzothienyl.

Embodiment 2: $R_1$ is the linker

Z is a radical of formula II $R_1$ is the linking group.

Suitable linking groups are well known in the art and include disulfide groups, thioether groups, acid labile groups, photolabile groups, peptidase labile groups and esterase labile groups. Preferred are disulfide groups and thioether groups.

When the linking group is a thiol- or disulfide-containing group, the side chain carrying the thiol or disulfide group can be linear or branched, aromatic or heterocyclic. One of ordinary skill in the art can readily identify suitable side chains.

Specific examples of the thiol- or disulfide-containing substituents include —(CR$_{13}$R$_{14}$)$_m$(CR$_{15}$R$_{16}$)$_n$(OCH$_2$CH$_2$)$_y$SZ', —O(CR$_{13}$R$_{14}$)$_m$(CR$_{15}$R$_{16}$)$_n$(OCH$_2$CH$_2$)$_y$SZ', —(CR$_{13}$R$_{14}$)$_m$ (CR$_{17}$=CR$_{18}$)(CR$_{15}$R$_{16}$)$_m$(OCH$_2$CH$_2$)$_y$SZ', —O— (CR$_{13}$R$_{14}$)$_m$(CR$_{17}$=CR$_{18}$)(CR$_{15}$R$_{16}$)$_m$(OCH$_2$CH$_2$)$_y$SZ', —NR$_{12}$(CR$_{13}$R$_{14}$)$_m$(CR$_{15}$R$_{16}$)$_n$(OCH$_2$CH$_2$)$_y$SZ', phenyl-X'SZ', furyl-XSZ', oxazolyl-X'SZ', thiazolyl-X'SZ', thienyl-X'SZ', imidazolyl-X'SZ', morpholino-X'SZ', -piperazino-X'SZ', piperidino-XSZ', -furyl-X'SZ', -thienyl-X'SZ', -thiazolyl-X'SZ' and —N-methylpiperazino-X'SZ', -morpholino-X'SZ', -piperazino-X'SZ', -piperidino-X'SZ', or —N-methylpiperazino-X'SZ', wherein:

Z' is H, a thiol protective group or SR', wherein X' is a direct link or a linear alkyl or branched alkyl having from 1-10 carbon atoms or a polyethylene glycol spacer with 2 to 20 repeating ethylene oxy units;

R' and $R_{12}$ are the same or different and are linear alkyl, branched alkyl or cyclic alkyl having from 1 to 10 carbon atoms, or simple or substituted aryl or heterocyclic, and $R_{12}$ can in addition be H, $R_{13}$, $R_{14}$, $R_{15}$ and $R_{16}$ are the same or different and are H or a linear or branched alkyl having from 1 to 4 carbon atoms, $R_{17}$ and $R_{18}$ are H or alkyl, n is an integer of 1 to 10, m is an integer from 1 to 10 and can also be 0, y is an integer from 1 to 20 and can also be 0.

$R_3$ is optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms Preferably, $R_3$ is crotyl, dimethylacrylyl, propenyl, isobutenyl, hexenyl, cyclopentenyl, cyclohexenyl, furyl, pyrollyl, thienyl, thiazolyl, imidazolyl, pyridyl, oxazolyl, indolyl, benzofuranyl or benzothienyl.

More preferably, $R_3$ is iso-bufenyl, crotyl, dimethyacrylyl, thienyl, thiazolyl, pyridyl, tert-butyl, or furyl.

$R_4$ is H, a hydroxy radical, an alkoxy, an alkenyloxy, an optionally substituted alkanoyloxy, aroyloxy, alkenoyloxy, alkynoyloxy, cycloalkanoyloxy, alkoxyacetyl, alkylthioacetyl, alkyloxycarbonyloxy, cycloalkyloxy, cycloalkenyloxy, carbamoyloxy, alkylcarbamoyloxy, or dialkylcarbamoyloxy, a heterocyclic or aryl ether, ester or carbamate, or, a linear, branched, or cyclic alkyl or alkenyl ester or ether having from 1 to 10 carbon atoms or a carbamate of the formula —OCOX, wherein X is a nitrogen-containing heterocycle such as unsubstituted or substituted piperidino, morpholino, piperazino, N-methylpiperazino, or a carbamate of the formula —OCONR$_9$R$_{10}$, wherein R$_9$ and R$_{10}$ are the same or different and are H, linear, branched, or cyclic alkyl having from 1 to 10 atoms or simple or substituted aryl having from 5 to 10 carbon atoms;

R$_5$ or R$_7$ is H

R$_6$ is H

R$_7$ or R$_5$ and R form a bond (cyclic ether)

R$_8$ is an optionally substituted aryl or heterocyclic radical

Preferably, R$_8$ is 3-methoxyphenyl, 3-chlorophenyl, 2,5-dimethoxyphenyl, furyl, pyrollyl, thienyl, thiazolyl, oxazolyl, imidazolyl, pyridyl, indolyl, benzofuranyl or benzothienyl.

Embodiment 3: R$_3$ is the linker

Z is a radical of formula II

R$_1$ is an optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms, —OR$_2$ or a carbamate formed from any of said alkyl having from 1 to 10 carbon atoms, alkenyl or alkynyl having from 2 to 10 carbon atoms, cycloalkyl or cycloalkenyl having from 3 to 10 carbon atoms, or optionally substituted aryl or heterocyclyl radical R$_2$ is alkyl radical having from 1 to 10 carbon atoms, alkenyl or alkynyl having from 2 to 10 carbon atoms, cycloalkyl or cycloalkenyl having from 3 to 10 carbon atoms, optionally substituted aryl or heterocyclic radical Preferably, R$_1$ is t-butoxy, crotyl, dimethylacrylyl, isobutenyl, hexenyl, cyclopentenyl, cyclohexenyl, furyl, pyrollyl, thienyl, thiazolyl, imidazolyl, pyridyl, morpholino, piperidino, piperazino, oxazolyl, indolyl, benzofuranyl or benzothienyl.

More preferably, R$_1$ is t-butoxy, isobutenyl, crotyl, dimethyacrylyl, thienyl, thiazolyl or furyl R$_3$ is the linking group.

Suitable linking groups are well known in the art and include disulfide groups, thioether groups, acid labile groups, photolabile groups, peptidase labile groups and esterase labile groups. Preferred are disulfide groups and thioether groups.

When the linking group is a thiol- or disulfide-containing group, the side chain carrying the thiol or disulfide group can be linear or branched, aromatic or heterocyclic. One of ordinary skill in the art can readily identify suitable side chains.

Specific examples of the thiol- or disulfide-containing substituents include —(CR$_{13}$R$_{14}$)$_m$(CR$_{15}$R$_{16}$)$_n$(OCH$_2$CH$_2$)$_y$SZ', —(CR$_{13}$R$_{14}$)$_m$(CR$_{17}$=CR$_{18}$)(CR$_{15}$R$_{16}$)$_m$(OCH$_2$CH$_2$)$_y$SZ', phenyl-X'SZ', furyl-X'SZ', oxazolyl-X'SZ', thiazolyl-X'SZ', thienyl-X'SZ', imidazolyl-X'SZ', wherein:

Z' is H, a thiol protective group or SR',

Wherein X' is a direct link or a linear alkyl or branched alkyl having from 1-10 carbon atoms or a polyethylene glycol spacer with 2 to 20 repeating ethylene oxy units;

R' is linear alkyl, branched alkyl or cyclic alkyl having from 1 to 10 carbon atoms, or simple or substituted aryl or heterocyclic, R$_{13}$, R$_{14}$, R$_{15}$ and R$_{16}$ are the same or different and are H or a linear or branched alkyl having from 1 to 4 carbon atoms, R$_{17}$ and R$_{18}$ are H or alkyl, n is an integer of 1 to 10, m is an integer from 1 to 10 and can also be 0, y is an integer from 1 to 20 and can also be 0.

R$_4$ is H, a hydroxy radical, an alkoxy, an alkenyloxy, an optionally substituted alkanoyloxy, aroyloxy, alkenoyloxy, alkynoyloxy, cycloalkanoyloxy, alkoxyacetyl, alkylthioacetyl, alkyloxycarbonyloxy, cycloalkyloxy, cycloalkenyloxy, carbamoyloxy, alkylcarbamoyloxy, or dialkylcarbamoyloxy, a heterocyclic or aryl ether, ester or carbamate, or, a linear, branched, or cyclic alkyl or alkenyl ester or ether having from 1 to 10 carbon atoms or a carbamate of the formula —OCOX, wherein X is a nitrogen-containing heterocycle such as unsubstituted or substituted piperidino, morpholino, piperazino, N-methylpiperazino, or a carbamate of the formula —OCONR$_9$R$_{10}$, wherein R$_9$ and R$_{10}$ are the same or different and are H, linear, branched, or cyclic alkyl having from 1 to 10 atoms or simple or substituted aryl having from 5 to 10 carbon atoms;

R$_5$ or R$_7$ is H

R$_6$ is H,

R$_7$ or R$_5$ and R form a bond (cyclic ether)

R$_8$ is an optionally substituted aryl or heterocyclic radical

Preferably, R$_8$ is 3-methoxyphenyl, 3-chlorophenyl, 2,5-dimethoxyphenyl, furyl, pyrollyl, thienyl, thiazolyl, imidazolyl, pyridyl, oxazolyl, indolyl, benzofuranyl or benzothienyl.

The following compounds of the invention have been synthesized

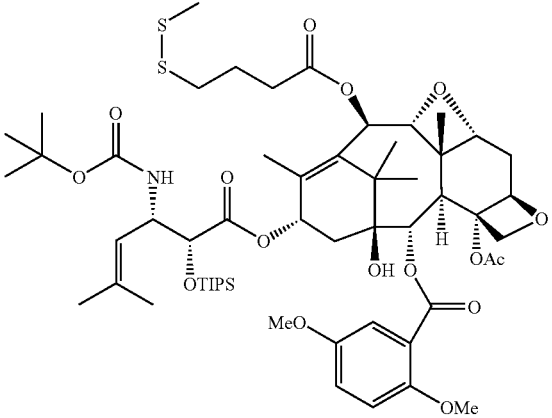

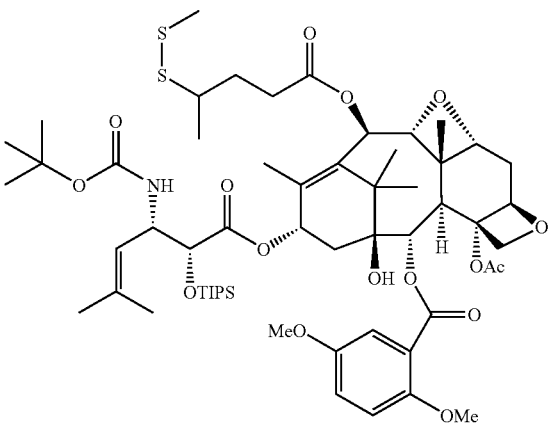

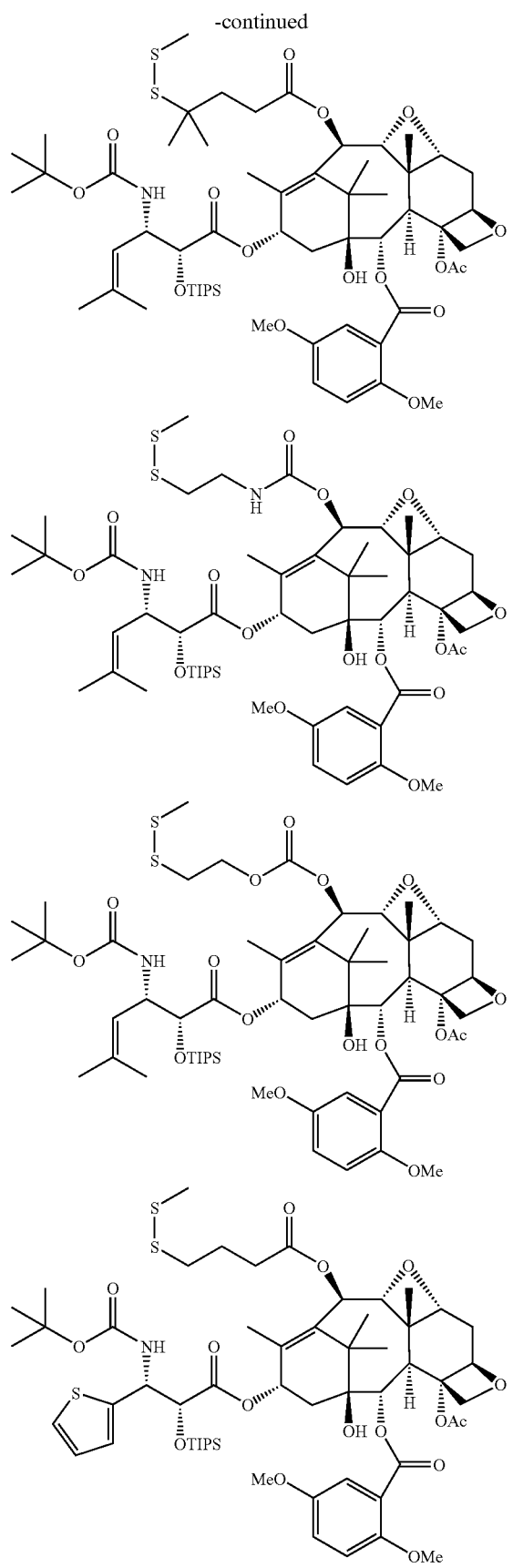
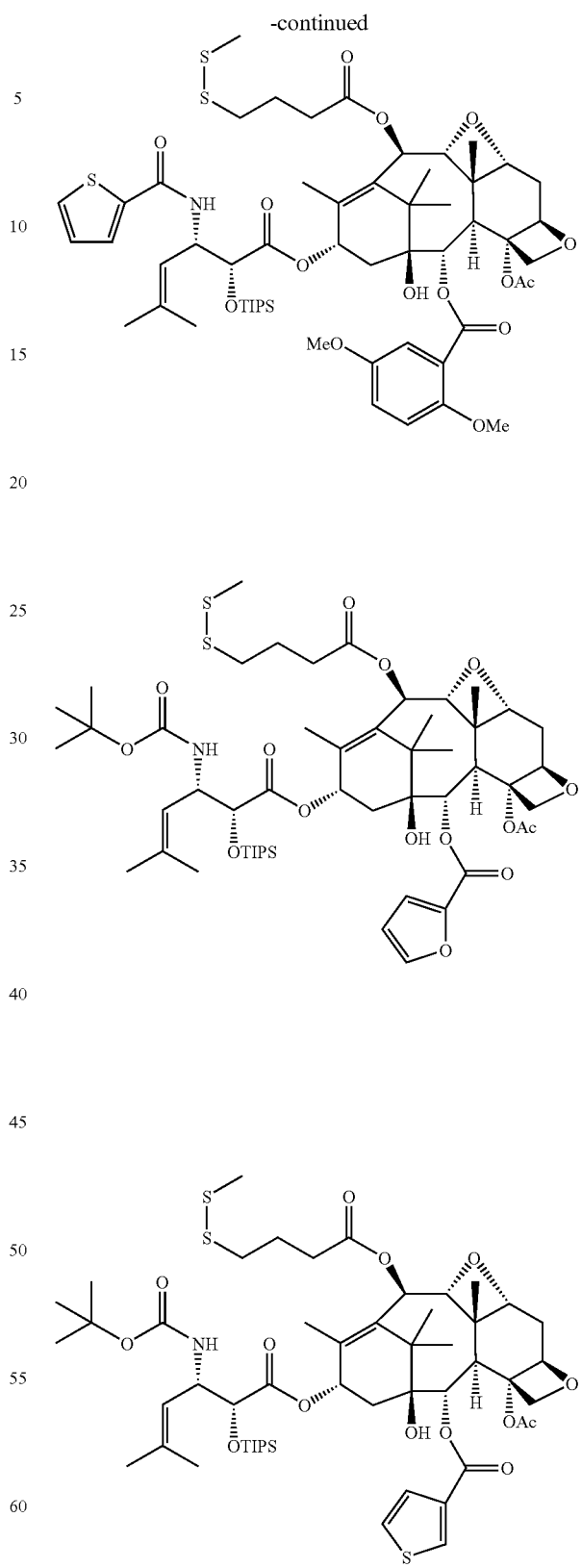
Many other possibilities exist
3'-isobutenyl series

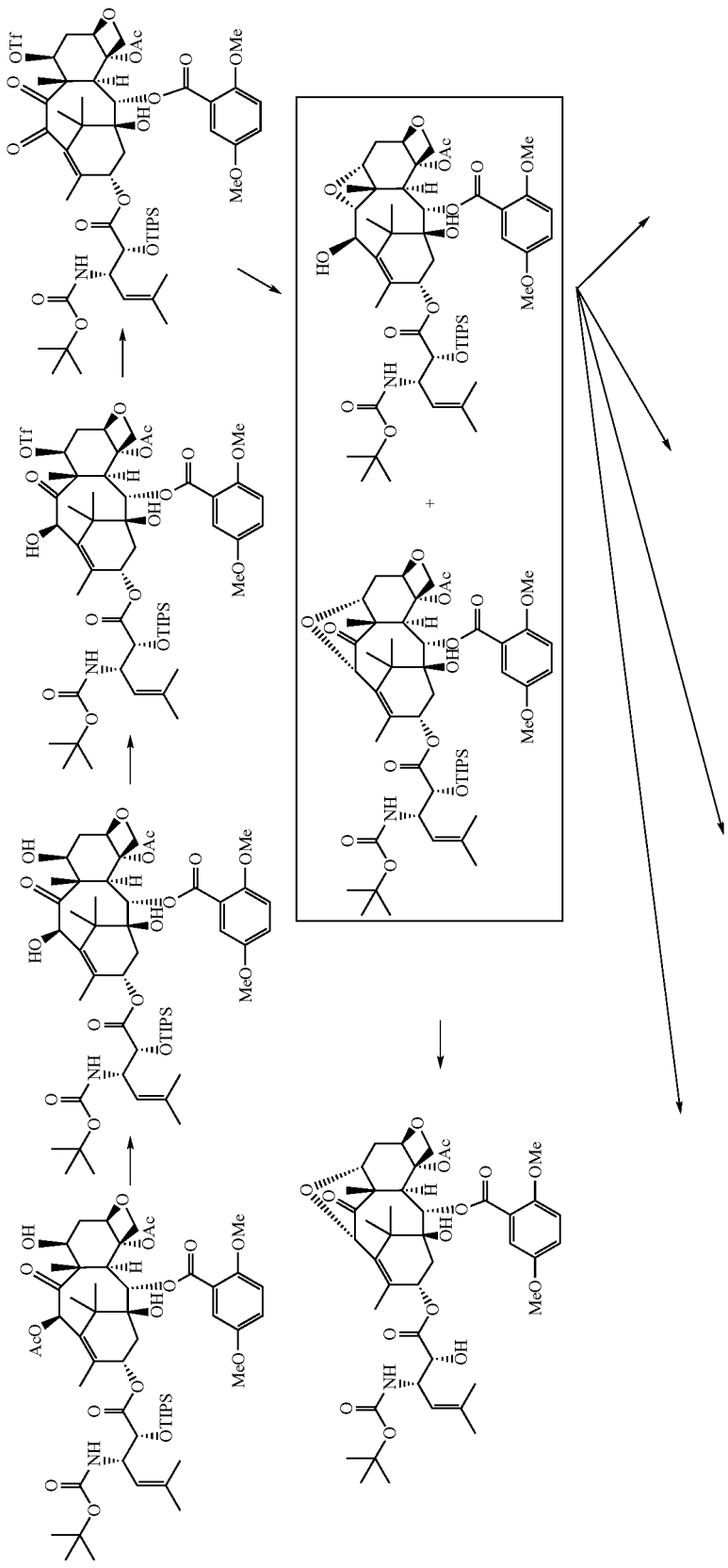

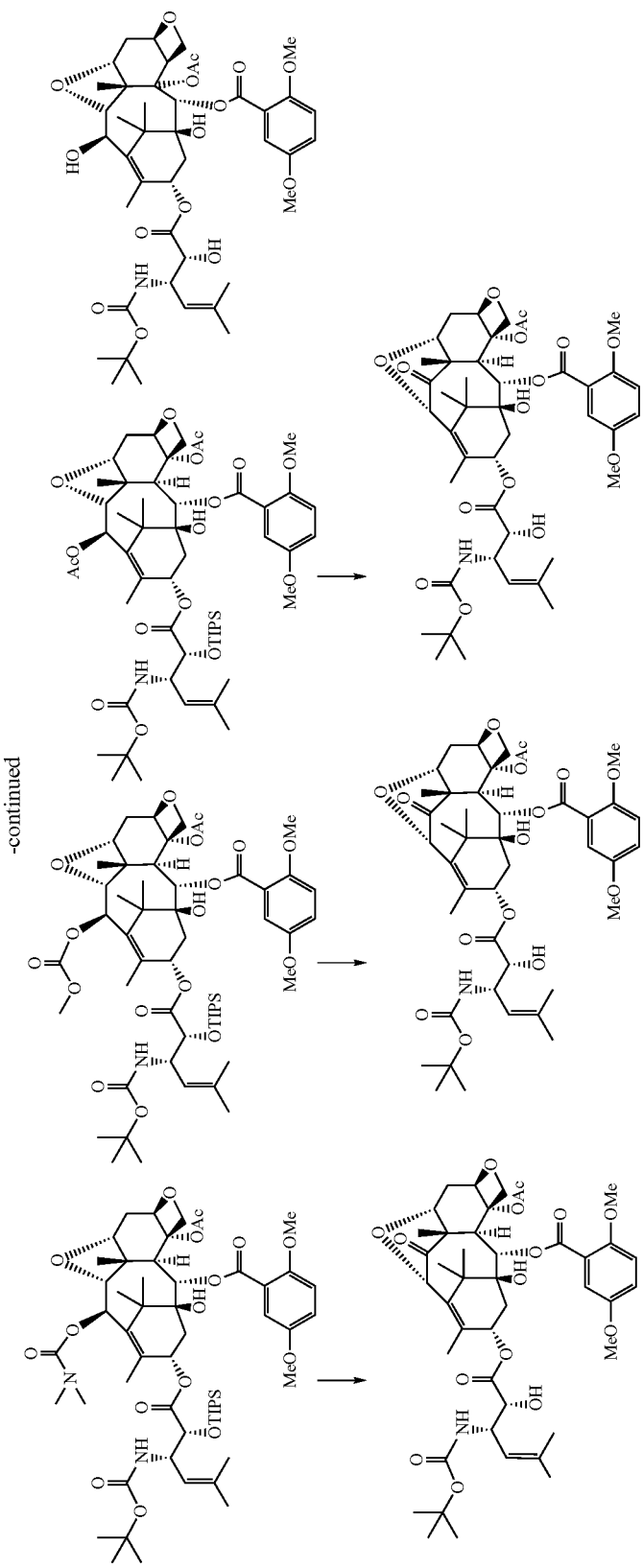

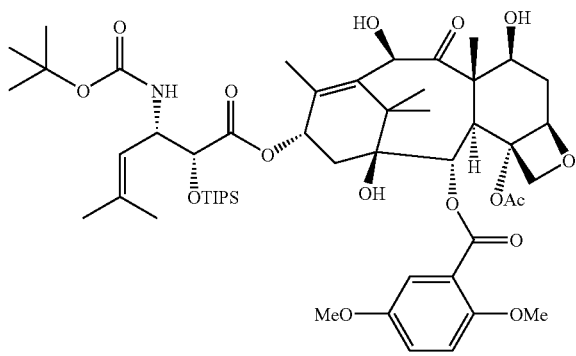

C₅₂H₇₉NO₁₆Si
Exact Mass: 1001.52

2'-(triisopropylsilyloxy)-3'-dephenyl-3'-(isobutenyl)-
2-debenzoyl-2-(2,5-dimethoxybenzoyl)-docetaxel To a solution of 10-acetoxy-2'-(triisopropylsilyloxy)-3'-dephenyl-3'-(isobutenyl)-2-debenzoyl-2-(2,5-dimethoxybenzoyl)-docetaxel (1.30 g, 1.25 mmol) in ethanol (25 mL) was added hydrazine monohydrate (10.5 mL) with stirring. After 15 minutes the reaction was diluted with ethyl acetate (50 mL) and the organic layer was extracted with ammonium chloride (50 mL), water (50 mL), and brine (50 mL). The organic layer was then dried over anhydrous sodium sulfate, filtered, and concentrated in vacuo. The residue was purified on a silica gel column using 40% ethyl acetate in hexane as the eluant. The fractions containing the desired product were pooled and concentrated to give 1.1 g of 2'-(triisopropylsilyloxy)-3'-dephenyl-3'-(isobutenyl)-2-debenzoyl-2-(2,5-dimethoxybenzoyl)-docetaxel as a white solid. $^1$H NMR (CDCl$_3$) δ 1.08 (s, 24H), 1.23 (s, 3H), 1.36 (s, 9H), 1.67 (s, 3H), 1.70 (s, 3H), 1.76 (s, 3H), 1.82 (m, 1H), 1.88 s, 3H), 2.16 (s, 3H), 2.31 (m, 1H), 2.50 (m, 2H), 3.17 (br s, 1H), 3.79 (s, 3H), 3.85 (d, J=6.4 Hz, 1H), 3.95 (s, 1H), 4.18 (m, 2H), 4.29 (d, J=8.4 Hz, 1H), 4.37 (d, J=2 Hz, 1H), 4.41 (d, J=8.4 Hz, 1H), 4.74 (t, J=9 Hz, 1H), 4.90 (t, J=9.8 Hz, 2 H), 5.17 (d, J=1.6 Hz, 1H), 5.32 (d, J=9.2 Hz, 1H), 5.65 (d, J=6.8 Hz, 1H), 6.10 (t, J=8.8 Hz, 1H), 6.93 (d, J=9.2 Hz, 1H), 7.05 (dd, J=9.2, 3.0 Hz, 1H), 7.28 (d, J=3.0 Hz, 1H). m/z LC/MS for C$_{52}$H$_{79}$NO$_{16}$SiNa$^+$: calcd: 1024.5; found: 1024.3.

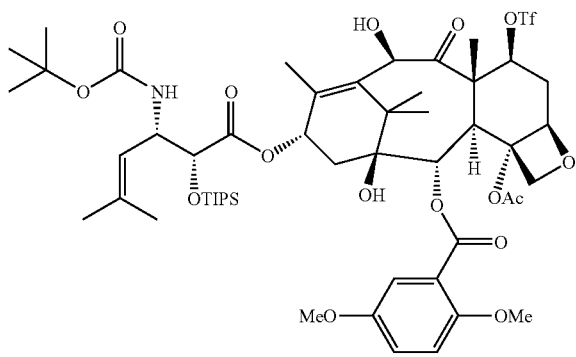

C₅₃H₇₈F₃NO₁₈SSi
Exact Mass: 1133.47

7-(trifluoromethanesulfonyloxy)-2'-(triisopropylsily-
loxy)-3'-dephenyl-3'-(isobutenyl)-2-debenzoyl-2-(2,
5-dimethoxybenzoyl)-docetaxel A solution of 2'-(triisopropylsilyloxy)-3'-dephenyl-3'-(isobutenyl)-2-debenzoyl-2-(2,5-dimethoxybenzoyl)-docetaxel (1.1 g, 1.1 mmol) in methylene chloride (7 mL) and pyridine (0.44 mL, 5.5 mmol) was cooled to −30° C. in a dry ice and acetone bath. A solution containing triflic anhydride (0.37 mL, 2.2 mmol) dissolved in methylene chloride (0.3 mL) was added dropwise. The resulting solution was allowed to gradually warm to room temperature with stirring. After one hour the reaction was diluted with ethyl acetate (25 mL) and the organic layer was extracted with ammonium chloride (25 mL), water (25 mL), and brine (25 mL). The organic layer was then dried over anhydrous sodium sulfate, filtered, and concentrated in vacuo. The residue was purified on a silica gel column using 20% ethyl acetate in hexane as the eluant. Fractions containing the desired product were pooled and concentrated to give 565 mg of 7-(trifluoromethanesulfonyloxy)-2'-(triisopropylsilyloxy)-3'-dephenyl-3'-(isobutenyl)-2-debenzoyl-2-(2,5-dimethoxybenzoyl)-docetaxel as a solid.
$^1$H NMR (CDCl$_3$) δ 1.10 (m, 24H), 1.26 (s, 3H), 1.38 (s, 9H), 1.68 (s, 3H), 1.72 (s, 3H), 1.92 (s, 3H), 1.95 (s, 3H), 2.20 (s, 3H), 2.28 (m, 1H), 2.31 (m, 1H), 2.50 (m, 1H), 2.80 (m, 1H), 3.80 (s, 3H), 3.95 (d, J=6.4 Hz, 1H), 3.98 (s, 3H), 4.36 (d, J=8.0 Hz, 1H), 4.38 (d, J=2.4 Hz, 1H), 4.44 (d, J=8.0 Hz, 1H), 4.76 (t, J=9.2 Hz, 1H), 4.88 (m, 2H), 5.33 (m, 2H), 5.38 (dd, J=6.8, 10.4 Hz, 1H), 5.68 (d, J=6.4 Hz, 1H), 6.13 (t, J=8.8 Hz, 1H), 6.95 (d, J=9.2 Hz, 1H), 7.07 (dd, J=3.2, 9.2 Hz, 1H), 7.26 (d, J=3.2 Hz, 1H). m/z LC/MS for C$_{53}$H$_{78}$F$_3$NO$_{18}$SSiNa$^+$: calcd: 1156.4. found: 1156.1.

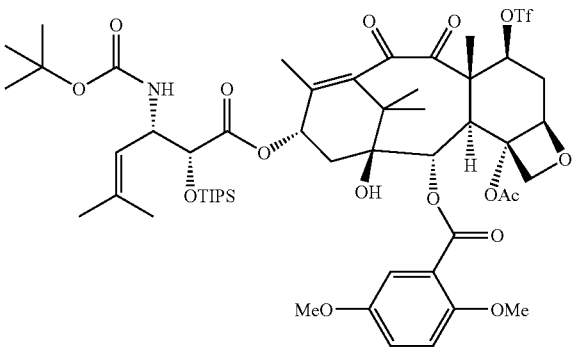

C₅₃H₇₆F₃NO₁₈SSi
Exact Mass: 1131.45

7-(trifluoromethanesulfonyloxy)-2'-(triisopropylsily-
loxy)-3'-dephenyl-3'-(isobutenyl)-10-oxo-2-deben-
zoyl-2-(2,5-dimethoxybenzoyl)-docetaxel To a stirred solution of 7-(trifluoromethanesulfonyloxy)-2'-(triisopropylsilyloxy)-3'-dephenyl-3'-(isobutenyl)-2-debenzoyl-2-(2,5-dimethoxybenzoyl)-docetaxel (565 mg, 0.5 mmol) in methylene chloride (20 mL) was added 4-methylmorpholine N-oxide (NMO) (117 mg, 1.00 mmol) followed by the addition of tetrapropylammonium perruthenate (TPAP) (10 mg, 0.03 mmol). The resulting mixture was allowed to stir at room temperature with monitoring. After 8 hours the reaction was filtered through celite and the pad of celite was rinsed with methylene chloride. The combined supernatant was concentrated in vacuo and the resulting residue was purified on a silica gel column using 25% ethyl acetate in hexane. The fractions containing the product were pooled and concentrated to give 325 mg of 7-(trifluoromethanesulfonyloxy)-2'-(triisopropylsilyloxy)-3'-dephenyl-3'-(isobutenyl)-10-oxo-2-debenzoyl-2-(2,5-dimethoxybenzoyl)-docetaxel as a solid.

$^1$H NMR (CDCl$_3$) δ 1.10 (m, 21H), 1.20 (s, 3H), 1.30 (s, 3H), 1.38 (s, 9H), 1.68 (s, 3H), 1.72 (s, 3H), 1.92 (s, 3H), 1.94 (s, 3H), 2.18 (s, 3H), 2.23 (m, 1H), 2.35 (m, 1H), 2.63 (m, 1H), 2.83 (m, 1H), 3.71 (m, 2H), 3.81 (s, 3H), 4.00 (s, 3H), 4.34 (d, J=8.4 Hz, 1H), 4.39 (d, J=2.0 Hz, 1H), 4.45 (d, J=8.4 Hz, 1H), 4.78 (t, J=9.2 Hz, 1H), 4.87 (m, 2H), 5.19 (dd, J=8.0, 10.0 Hz, 1H), 5.34 (d, J=8.8 Hz, 1H), 5.79 (d, J=6.0 Hz, 1H), 6.09 (t, J=8.8 Hz, 1H), 6.98 (d, J=9.2 Hz, 1H), 7.09 (dd, J=3.2 9.2 Hz, 1H), 7.25 (d, J=3.2 Hz, 1H). m/z LC/MS for C$_{53}$H$_{76}$F$_3$NO$_{18}$SSiNa$^+$: calcd: 1154.4. found: 1154.4.

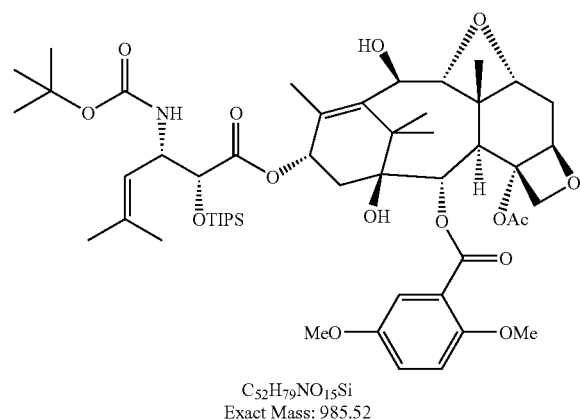

C$_{52}$H$_{79}$NO$_{15}$Si
Exact Mass: 985.52

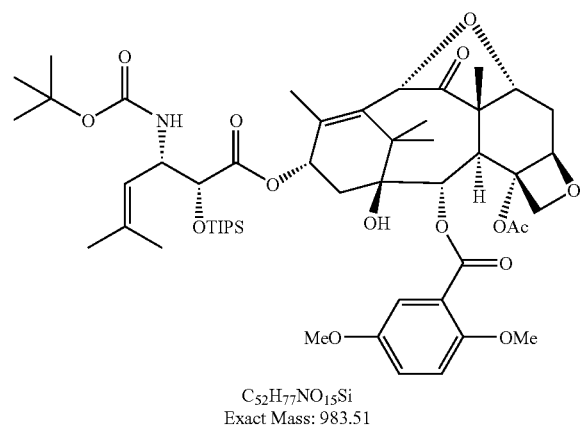

C$_{52}$H$_{77}$NO$_{15}$Si
Exact Mass: 983.51

7α,9α-epoxy-2'-(triisopropylsilyloxy)-3'-dephenyl-3'-(isobutenyl)-2-debenzoyl-2-(2,5-dimethoxybenzoyl)-docetaxel To a well stirred mixture of 7-(trifluoromethane-sulfonyloxy)-2'-(triisopropylsilyloxy)-3'-dephenyl-3'-(isobutenyl)-10-oxo-2-debenzoyl-2-(2,5-dimethoxybenzoyl)-docetaxel (323 mg, 0.286 mmol) in ethanol (3.5 mL) was added sodium borohydride (58 mg, 1.5 mmol). After 10 minutes the reaction was diluted with ethyl acetate (15 mL) and extracted twice with brine (15 mL). The organic layer was dried over anhydrous sodium sulfate, filtered, and concentrated in vacuo. The residue was purified by silica ptlc using 50% ethyl acetate in hexane as the developing solvent to give the desired product, 7α,9α-epoxy-2'-(triisopropylsilyloxy)-3'-dephenyl-3'-(isobutenyl)-2-debenzoyl-2-(2,5-dimethoxybenzoyl)-docetaxel (171 mg) and the side product 7α,10α-epoxy-2'-(triisopropylsilyloxy)-3'-dephenyl-3'-(isobutenyl)-2-debenzoyl-2-(2,5-dimethoxybenzoyl)-docetaxel (78 mg).

7α,9α-epoxy-2'-(triisopropylsilyloxy)-3'-dephenyl-3'-(isobutenyl)-2-debenzoyl-2-(2,5-dimethoxybenzoyl)-docetaxel $^1$H NMR (CDCl$_3$) δ 1.09 (m, 24H), 1.24 (s, 3H), 1.38 (s, 9H), 1.68 (s, 3H), 1.71 (s, 3H), 1.78 (s, 3H), 1.97 (s, 3H), 2.10 (s, 3H), 2.23-2.33 (m, 2H), 2.34-2.45 (m, 2H), 2.50 (d, J=3.2 Hz, 1H), 3.80 (s, 3H), 3.98 (s, 3H), 4.02 (d, J=6.0 Hz, 1H), 4.25 (d, J=7.2 Hz, 1H), 4.34 (d, J=7.2 Hz, 1H), 4.45 (d, J=2.4 Hz, 1H), 4.73-4.83 (m, 4H), 4.98 (m, 2H), 5.35 (d, J=8.8 Hz, 1H), 5.67 (d, J=6.4 Hz, 1 H), 5.97 (t, J=8.8 Hz, 1H), 6.96 (d, J=9.2 Hz, 1H), 7.06 (dd, J=3.2 9.2 Hz, 1H), 7.29 (d, J=3.2 Hz, 1H). m/z LC/MS for C$_{52}$H$_{79}$NO$_{15}$SiNa$^+$: calcd: 1008.5. found: 1008.4.

7α,10α-epoxy-2'-(triisopropylsilyloxy)-3'-dephenyl-3'-(isobutenyl)-2-debenzoyl-2-(2,5-dimethoxybenzoyl)-docetaxel $^1$H NMR (CDCl$_3$) δ 1.10 (m, 21H), 1.19 (s, 3H), 1.34 (s, 3H), 1.39 (s, 9H), 1.66 (s, 3H), 1.70 (s, 3H), 1.84 (s, 3H), 1.88 (s, 3H), 2.07 (s, 3H), 2.21 (m, 1H), 2.29 (m, 1H), 2.38 (m, 2H), 3.66 (d, J=7.6 Hz, 1H), 3.81 (s, 3H), 3.96 (s, 3H), 4.39-4.47 (m, 4H), 4.74 (t, J=8.4 Hz, 1H), 4.82 (br s, 1H), 4.90 (m, 1H), 5.08 (d, J=4.4 Hz, 1H), 5.35 (d, J=8.8 Hz, 1H), 5.42 (d, J=6.0 Hz, 1H), 6.12 (t, J=8.8 Hz, 1H), 6.95 (d, J=8.8 Hz, 1H), 7.07 (dd, J=3.2, 8.8 Hz, 1H), 7.32 (d, J=3.2 Hz, 1H). m/z LC/MS for C$_{52}$H$_{77}$NO$_{15}$SiNa$^+$: calcd: 1006.5. found: 1006.4.

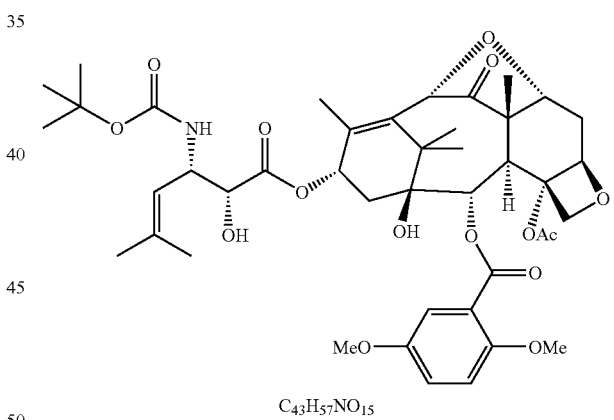

C$_{43}$H$_{57}$NO$_{15}$
Exact Mass: 827.37

7α,10α-epoxy-3'-dephenyl-3'-(isobutenyl)-2-debenzoyl-2-(2,5-dimethoxybenzoyl)-docetaxel A solution containing 7α,10α-epoxy-2'-(triisopropylsilyloxy)-3'-dephenyl-3'-(isobutenyl)-2-debenzoyl-2-(2,5-dimethoxy-benzoyl)-docetaxel (20 mg, 0.02 mmol) dissolved in a 1:1 mixture of acetonitrile: pyridine (2 mL) was cooled to 0° C. in an ice bath. To this was added hydrogen fluoride-pyridine (0.2 mL) and the solution was allowed to gradually warm to room temperature. After 16 hours the reaction was diluted with ethyl acetate (15 mL) and quenched with a saturated sodium bicarbonate solution (15 mL). The organic layer was washed once with brine (20 mL) and then dried over anhydrous sodium sulfate, filtered, and concentrated in vacuo. The crude residue was purified by silica ptlc using 70% ethyl acetate in hexane as the developing solvent. The band containing the desired product was scraped and rinsed with ethyl acetate at the filter. The organic layers were combined and concentrated in vacuo to give 12 mg of 7α,10α-epoxy-3'-dephenyl-3'-(isobutenyl)-2-debenzoyl-2-(2,5-dimethoxybenzoyl)-docetaxel as a white solid.

$^1$H NMR (CDCl$_3$) δ 1.19 (s, 3H), 1.32 (s, 3H), 1.41 (s, 9H), 1.73 (s, 6H), 1.85 (s, 3H), 1.89 (s, 3H), 2.03 (s, 3H), 2.28-2.42 (m, 4H), 3.69 (dd, J=2.0, 7.2 Hz, 1H), 3.81 (s, 3H), 3.89 (s, 3H), 4.25 (dd, J=2.4, 4.4, 1H), 4.34 (d, J=6.0 Hz, 1H), 4.36 (d, J=6.0 Hz, 1H), 4.53 (d, J=7.6 Hz, 1H), 4.82 (m, 2H), 5.00 (d, J=9.2 Hz, 1H), 5.08 (m, 1H), 5.25 (d, J=8.8 Hz, 1H), 5.35 (d, J=6.0 Hz, 1H), 6.17 (t, J=7.6 Hz, 1H), 6.94 (d, J=9.2 Hz, 1H), 7.06 (dd, J=3.2, 9.2 Hz, 1H), 7.28 (d, J=3.2 Hz, 1H). m/z LC/MS for C$_{43}$H$_{57}$NO$_{15}$Na$^+$: calcd: 850.4. found: 850.3.

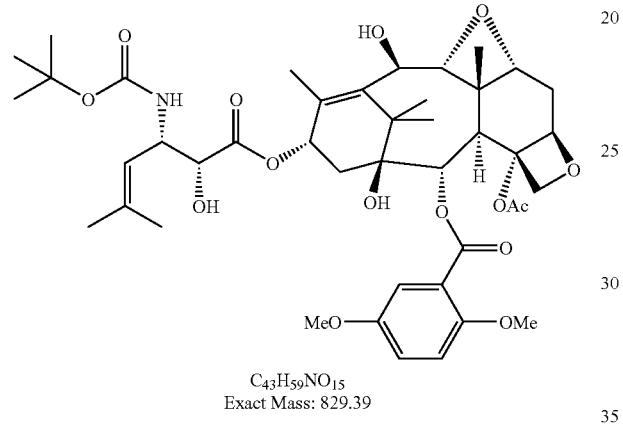

C$_{43}$H$_{59}$NO$_{15}$
Exact Mass: 829.39

7α,9α-epoxy-2'-3'-dephenyl-3'-(isobutenyl)-2-debenzoyl-2-(2,5-dimethoxybenzoyl)-docetaxel A solution containing 7α,9α-epoxy-2'-(triisopropylsilyloxy)-3'-dephenyl-3'-(isobutenyl)-2-debenzoyl-2-(2,5-dimethoxybenzoyl)-docetaxel (25 mg, 0.025 mmol) dissolved in a 1:1 mixture of acetonitrile: pyridine (2 mL) was cooled to 0° C. in an ice bath. To this was added hydrogen fluoride-pyridine (0.25 mL) and the solution was allowed to gradually warm to room temperature. After 16 hours the reaction was diluted with ethyl acetate (15 mL) and quenched with a saturated sodium bicarbonate solution (15 mL). The organic layer was washed once with brine (20 mL) and then dried over anhydrous sodium sulfate, filtered, and concentrated in vacuo. The crude residue was purified by silica ptlc using 70% ethyl acetate in hexane as the developing solvent. The band containing the desired product was scraped and rinsed with ethyl acetate at the filter. The organic layers were combined and concentrated in vacuo to give 12 mg of 7α,9α-epoxy-3'-dephenyl-3'-(isobutenyl)-2-debenzoyl-2-(2,5-dimethoxybenzoyl)-docetaxel as a white solid.

$^1$H NMR (CDCl$_3$) δ 1.12 (s, 3H), 1.23 (s, 3H), 1.41 (s, 9H), 1.73 (s, 6H), 1.80 (s, 3H), 2.01 (s, 3H), 2.07 (s, 3H), 2.15-2.21 (m, 1H), 2.23-2.28 (m, 1H), 2.36-2.44 (m, 1H), 2.43-2.49 (m, 1H), 2.52 (d, J=6.8 Hz, 1H), 3.75 (br s, 1H), 3.80 (s, 3H), 3.93 (s, 3H), 4.05 (d, J=6.4 Hz, 1H), 4.26 (d, J=2.4, 4.8 Hz, 1H), 4.30 (d, J=7.6 Hz, 1H), 4.32 (d, J=7.6 Hz, 1H), 4.76-4.83 (m, 4H), 4.91 (t, J=2.0 Hz, 1H), 4.98 (d, J=9.6 Hz, 1H), 5.26 (d, J=8.4 Hz, 1H), 5.65 (d, J=6.4 Hz, 1 H), 6.01 (t, J=8.8 Hz, 1H), 6.95 (d, J=9.2 Hz, 1H), 7.06 (dd, J=3.2 9.2 Hz, 1H), 7.28 (d, J=3.2 Hz, 1H). m/z LC/MS for C$_{43}$H$_{59}$NO$_{15}$Na$^+$: calcd: 852.4. found: 852.3.

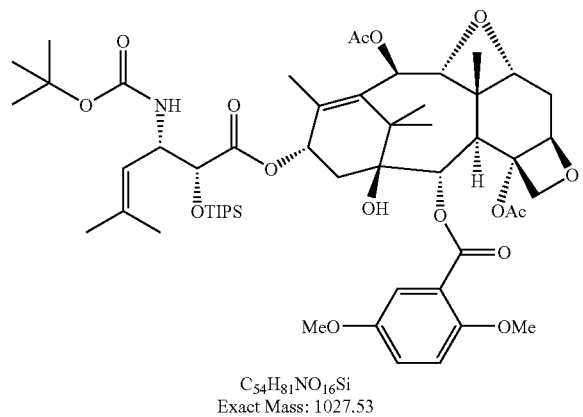

C$_{54}$H$_{81}$NO$_{16}$Si
Exact Mass: 1027.53

7α,9α-epoxy-2'-(triisopropylsilyloxy)-3'-dephenyl-3'-(isobutenyl)-2-debenzoyl-2-(2,5-dimethoxybenzoyl)-10-acetoxy-docetaxel To a solution of 7α,9α-epoxy-2'-(triisopropylsilyloxy)-3'-dephenyl-3'-(isobutenyl)-2-debenzoyl-2-(2,5-dimethoxybenzoyl)-docetaxel (85 mg, 0.086 mmol) dissolved in pyridine (1 mL) under nitrogen was added dimethylamino pyridine (DMAP) (16 mg, 0.13 mmol) and acetic anhydride (0.025 mL, 0.26 mmol). The reaction was stirred at room temperature and after 4 hours was diluted with ethyl acetate (20 mL) and washed once with brine (25 mL). The organic layer was separated, dried over anhydrous sodium sulfate, filtered, and concentrated in vacuo. The residue was purified by silica ptlc using 50% ethyl acetate in hexane as the developing solvent. The band containing the desired product was scraped and rinsed with ethyl acetate at the filter. The organic layers were combined and concentrated in vacuo to give 75 mg of 7α,9α-epoxy-2'-(triisopropylsilyloxy)-3'-dephenyl-3'-(isobutenyl)-2-debenzoyl-2-(2,5-dimethoxybenzoyl)-10-acetoxy-docetaxel as a white solid.

$^1$H NMR (CDCl$_3$) δ 1.10 (m, 21H), 1.22 (s, 6H), 1.38 (s, 9H), 1.67 (s, 3H), 1.70 (s, 3H), 1.73 (s, 3H), 1.94 (s, 3H), 2.07 (s, 3H), 2.10 (s, 3H), 2.31 (m, 3H), 2.48 (m, 1H), 3.78 (s, 3H), 3.97 (s, 3H), 3.98 (d, J=6.0 Hz, 1H), 4.24 (d, J=7.2 Hz, 1H), 4.32 (d, J=7.2 Hz, 1H), 4.45 (d, J=2.0 Hz, 1H), 4.77 (m, 2H), 4.82 (d, J=6.0 Hz, 1H), 4.91 (s, 1H), 4.93 (d, J=9.2 Hz, 1H), 5.36 (d, J=8.4 Hz, 1H), 5.68 (d, J=9.2 Hz, 1H), 5.70 (d, J=6.0 Hz, 1H), 5.89 (t, J=8.8 Hz, 1H), 6.94 (d, J=9.2 Hz, 1H), 7.05 (dd, J=3.2 9.2 Hz, 1H), 7.29 (d, J=3.2 Hz, 1H). m/z LC/MS for C$_{54}$H$_{81}$NO$_{16}$SiNa$^+$: calcd: 1050.5. found: 1050.5.

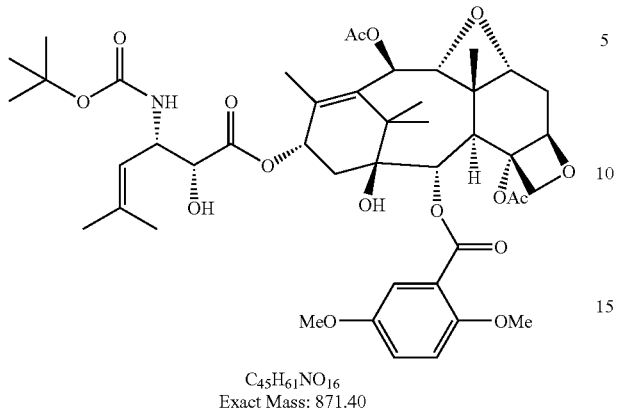

$C_{45}H_{61}NO_{16}$
Exact Mass: 871.40

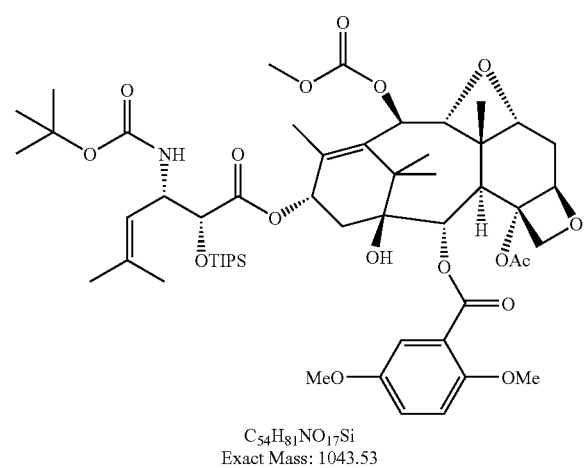

$C_{54}H_{81}NO_{17}Si$
Exact Mass: 1043.53

7α,9α-epoxy-3'-dephenyl-3'-(isobutenyl)-2-debenzoyl-2-(2,5-dimethoxybenzoyl)-10-acetoxy-docetaxel A solution containing 7α,9α-epoxy-2'-(triisopropylsilyloxy)-3'-dephenyl-3'-(isobutenyl)-2-debenzoyl-2-(2,5-dimethoxybenzoyl)-10-acetoxy-docetaxel (75 mg, 0.073 mmol) dissolved in a 1:1 mixture of acetonitrile: pyridine (3 mL) was cooled to 0° C. in an ice bath. To this was added hydrogen fluoride-pyridine (0.5 mL) and the solution was allowed to gradually warm to room temperature. After 16 hours the reaction was diluted with ethyl acetate (25 mL) and quenched with a saturated sodium bicarbonate solution (25 mL). The organic layer was washed once with brine (30 mL) and then dried over anhydrous sodium sulfate, filtered, and concentrated in vacuo. The crude residue was purified by silica ptlc using 70% ethyl acetate in hexane as the developing solvent. The band containing the desired product was scraped and rinsed with ethyl acetate at the filter. The organic layers were combined and concentrated in vacuo to give 52 mg of 7α,9α-epoxy-3'-dephenyl-3'-(isobutenyl)-2-debenzoyl-2-(2,5-dimethoxybenzoyl)-10-acetoxy-docetaxel.

$^1$H NMR (CDCl$_3$) δ 1.26 (s, 3H), 1.28 (s, 3H), 1.41 (s, 9H), 1.74 (s, 6H), 1.76 (s, 3H), 1.99 (s, 3H), 2.09 (s, 3H), 2.11 (s, 3H), 2.18 (m, 1H), 2.27 (m, 1H), 2.36 (m, 1H), 2.49 (m, 1H), 3.81 (s, 3H), 3.91 (s, 1H), 3.94 (s, 3H), 4.02 (d, J=6.0 Hz, 1H), 4.28 (m, 2H), 4.33 (d, J=7.2 Hz, 1H), 4.80 (m, 2H), 4.86 (d, J=6.4 Hz, 1H), 4.91 (s, 1H), 5.00 (d, J=9.2 Hz, 1H), 5.29 (d, J=8.4 Hz, 1H), 5.67 (d, J=6.4 Hz, 1H), 5.71 (d, J=6.4 Hz, 1H), 6.01 (t, J=8.8 Hz, 1H), 6.96 (d, J=9.2 Hz, 1H), 7.07 (dd, J=3.2 9.2 Hz, 1H), 7.28 (d, J=3.2 Hz, 1H). m/z LC/MS for C$_{45}$H$_{61}$NO$_{16}$Na$^+$: calcd: 894.4. found: 894.5.

7α,9α-epoxy-2'-(triisopropylsilyloxy)-3'-dephenyl-3'-(isobutenyl)-2-debenzoyl-2-(2,5-dimethoxybenzoyl)-10-methoxycarbonyloxy-docetaxel A solution of 7α,9α-epoxy-2'-(triisopropylsilyloxy)-3'-dephenyl-3'-(isobutenyl)-2-debenzoyl-2-(2,5-dimethoxybenzoyl)-docetaxel (28 mg, 0.029 mmol) dissolved in anhydrous tetrahydrofuran (0.65 mL) under nitrogen was cooled to −40° C. in a dry ice and acetone bath. To this solution was added 1.0 M LiHMDS (0.04 mL, 0.039 mmol) and allowed to stir for 15 minutes. To this was added methyl chloroformate (0.003 mL, 0.036 mmol) and the reaction was monitored at −40° C. After one hour the reaction was diluted with ethyl acetate (15 mL) and extracted with water (15 mL) followed by washing the organic layer with brine (15 mL). The organic layer was dried over anhydrous sodium sulfate, filtered, and concentrated in vacuo. The residue was purified by silica ptlc using 5% methanol in methylene chloride as the developing solvent. The band containing the desired product was scraped and rinsed with ethyl acetate at the filter. The organic layers were combined and concentrated in vacuo to give 9 mg of 7α,9α-epoxy-2'-(triisopropylsilyloxy)-3'-dephenyl-3'-(isobutenyl)-2-debenzoyl-2-(2,5-dimethoxybenzoyl)-10-methoxycarbonyloxy-docetaxel as a white solid.

$^1$H NMR (CDCl$_3$) δ 1.10 (m, 21H), 1.22 (s, 3H), 1.24 (s, 3H), 1.39 (s, 9H), 1.68 (s, 3H), 1.71 (s, 3H), 1.75 (s, 3H), 1.96 (s, 3H), 2.08 (s, 3H), 2.30 (m, 3H), 2.50 (m, 1H), 3.78 (s, 3H), 3.80 (s, 3H), 3.98 (d, J=6.0 Hz, 1H), 3.99 (s, 3H), 4.25 (d, J=7.2 Hz, 1H), 4.34 (d, J=7.2 Hz, 1H), 4.46 (d, J=2.0 Hz, 1H), 4.78 (m, 2H), 4.91 (m, 3H), 5.37 (d, J=8.4 Hz, 1H), 5.57 (d, J=6.4 Hz, 1H), 5.70 (d, J=6.0 Hz, 1H), 5.93 (t, J=8.8 Hz, 1H), 6.95 (d, J=9.2 Hz, 1H), 7.06 (dd, J=3.2 9.2 Hz, 1H), 7.30 (d, J=3.2 Hz, 1H). m/z LC/MS for C$_{45}$H$_{81}$NO$_{17}$SiNa$^+$: calcd: 1066.5. found: 1066.3.

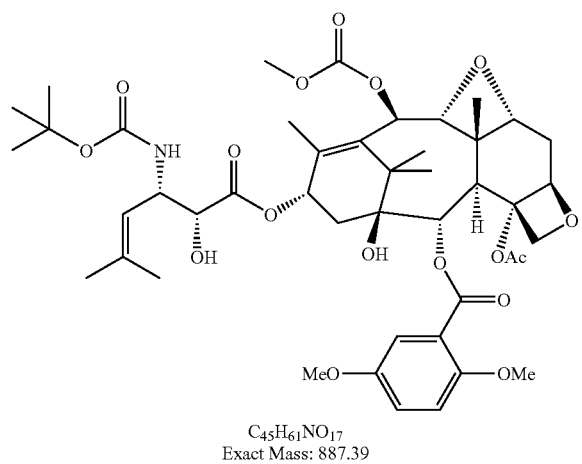

C₄₅H₆₁NO₁₇
Exact Mass: 887.39

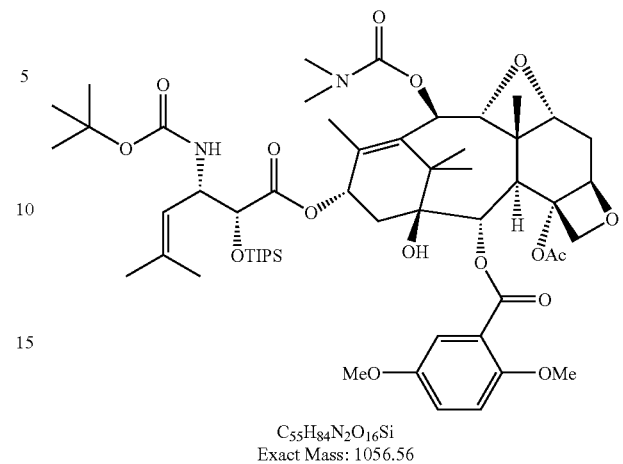

C₅₅H₈₄N₂O₁₆Si
Exact Mass: 1056.56

7α,9α-epoxy-3'-dephenyl-3'-(isobutenyl)-2-debenzoyl-2-(2,5-dimethoxybenzoyl)-10-methoxycarbonyloxy-docetaxel A solution containing 7α,9α-epoxy-2'-(triisopropylsilyloxy)-3'-dephenyl-3'-(isobutenyl)-2-debenzoyl-2-(2,5-dimethoxybenzoyl)-10-methoxycarbonyloxy-docetaxel (9 mg, 0.008 mmol) dissolved in a 1:1 mixture of acetonitrile:pyridine (1.2 mL) was cooled to 0° C. in an ice bath. To this was added hydrogen fluoride-pyridine (0.15 mL) and the solution was allowed to gradually warm to room temperature. After 16 hours the reaction was diluted with ethyl acetate (15 mL) and quenched with a saturated sodium bicarbonate solution (15 mL). The organic layer was washed once with brine (15 mL) and then dried over anhydrous sodium sulfate, filtered, and concentrated in vacuo. The crude residue was purified by silica ptlc using 60% ethyl acetate in hexane as the developing solvent. The band containing the desired product was scraped and rinsed with ethyl acetate at the filter. The organic layers were combined and concentrated in vacuo to give 4 mg of 7α,9α-epoxy-3'-dephenyl-3'-(isobutenyl)-2-debenzoyl-2-(2,5-dimethoxybenzoyl)-10-methoxycarbonyloxy-docetaxel.

$^1$H NMR (CDCl$_3$) δ 1.25 (s, 3H), 1.27 (s, 3H), 1.40 (s, 9H), 1.73 (s, 6H), 1.76 (s, 3H), 1.99 (s, 3H), 2.07 (s, 3H), 2.18 (m, 1H), 2.25 (m, 1H), 2.34 (m, 1H), 2.48 (m, 1H), 3.78 (s, 3H), 3.80 (s, 3H), 3.83 (s, 1H), 3.93 (s, 3H), 4.01 (d, J=6.0 Hz, 1H), 4.28 (m, 2H), 4.31 (d, J=7.6 Hz, 1H), 4.80 (m, 2H), 4.90 (s, 1H), 4.94 (d, J=7.6 Hz, 1H), 4.97 (d, J=9.6 Hz, 1H), 5.27 (d, J=7.6 Hz, 1H), 5.55 (d, J=6.0 Hz, 1H), 5.70 (d, J=6.0 Hz, 1H), 6.03 (t, J=8.8 Hz, 1H), 6.95 (d, J=9.2 Hz, 1H), 7.06 (dd, J=3.2 9.2 Hz, 1H), 7.28 (d, J=3.2 Hz, 1H). m/z LC/MS for C$_{45}$H$_{61}$NO$_{17}$Na$^+$: calcd: 910.4. found: 910.4.

7α,9α-epoxy-2'-(triisopropylsilyloxy)-3'-dephenyl-3'-(isobutenyl)-2-debenzoyl-2-(2,5-dimethoxybenzoyl)-10-dimethyaminocarbonyloxy-docetaxel A solution of 7α,9α-epoxy-2'-(triisopropylsilyloxy)-3'-dephenyl-3'-(isobutenyl)-2-debenzoyl-2-(2,5-dimethoxybenzoyl)-docetaxel (28 mg, 0.029 mmol) dissolved in anhydrous tetrahydrofuran (0.65 mL) under nitrogen was cooled to −40° C. in a dry ice and acetone bath. To this solution was added 1.0 M LiHMDS (0.04 mL, 0.039 mmol) and allowed to stir for 15 minutes. To this was added dimethyl carbamyl chloride (0.003 mg, 0.031 mmol) and the reaction was monitored at −40° C. After one hour the reaction was diluted with ethyl acetate (15 mL) and extracted with water (15 mL) followed by washing the organic layer with brine (15 mL). The organic layer was dried over anhydrous sodium sulfate, filtered, and concentrated in vacuo. The residue was purified by silica ptlc using 5% methanol in methylene chloride as the developing solvent. The band containing the desired product was scraped and rinsed with ethyl acetate at the filter. The organic layers were combined and concentrated in vacuo to give 20 mg of 7α,9α-epoxy-2'-(triisopropylsilyloxy)-3'-dephenyl-3'-(isobutenyl)-2-debenzoyl-2-(2,5-dimethoxybenzoyl)-10-dimethyaminocarbonyloxy-docetaxel as a white solid.

$^1$H NMR (CDCl$_3$) δ 1.10 (m, 21H), 1.23 (s, 6H), 1.39 (s, 9H), 1.68 (s, 3H), 1.71 (s, 3H), 1.73 (s, 3H), 1.98 (s, 3H), 2.09 (s, 3H), 2.31 (m, 3H), 2.49 (m, 1H), 2.93 m(s, 6H), 3.80 (s, 3H), 3.98 (s, 3H), 3.96 (d, J=6.0 Hz, 1H), 4.25 (d, J=7.2 Hz, 1H), 4.33 (d, J=7.2 Hz, 1H), 4.46 (d, J=2.0 Hz, 1H), 4.77 (m, 2H), 4.88 (d, J=6.4 Hz, 1H), 4.92 (m, 2H), 5.36 (d, J=8.4 Hz, 1H), 5.68 (d, J=6.0 Hz, 1H), 5.71 (d, J=6.4 Hz, 1H), 5.93 (t, J=8.8 Hz, 1H), 6.95 (d, J=9.2 Hz, 1H), 7.05 (dd, J=3.2 9.2 Hz, 1H), 7.30 (d, J=3.2 Hz, 1H). m/z LC/MS for C$_{55}$H$_{84}$N$_2$O$_{16}$SiNa$^+$: calcd: 1079.6. found: 1079.5.

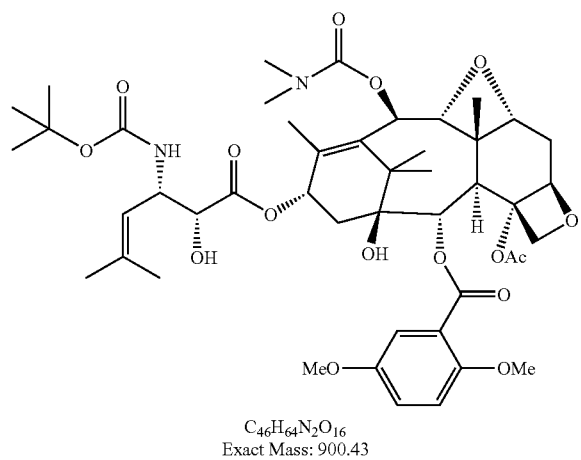

C₄₆H₆₄N₂O₁₆
Exact Mass: 900.43

7α,9α-epoxy-3'-dephenyl-3'-(isobutenyl)-2-debenzoyl-2-(2,5-dimethoxybenzoyl)-10-dimethyaminocarbonyloxy-docetaxel A solution containing 7α,9α-epoxy-2'-(triisopropylsilyloxy)-3'-dephenyl-3'-(isobutenyl)-2-debenzoyl-2-(2,5-dimethoxybenzoyl)-10-dimethyaminocarbonyloxy-docetaxel (20 mg, 0.016 mmol) dissolved in a 1:1 mixture of acetonitrile: pyridine (1.2 mL) was cooled to 0° C. in an ice bath. To this was added hydrogen fluoride-pyridine (0.25 mL) and the solution was allowed to gradually warm to room temperature. After 16 hours the reaction was diluted with ethyl acetate (15 mL) and quenched with a saturated sodium bicarbonate solution (15 mL). The organic layer was washed once with brine (15 mL) and then dried over anhydrous sodium sulfate, filtered, and concentrated in vacuo. The crude residue was purified by silica ptlc using 70% ethyl acetate in hexane as the developing solvent. The band containing the desired product was scraped and rinsed with ethyl acetate at the filter. The organic layers were combined and concentrated in vacuo to give 12 mg of 7α,9α-epoxy-3'-dephenyl-3'-(isobutenyl)-2-debenzoyl-2-(2,5-dimethoxybenzoyl)-10-dimethyaminocarbonyloxy-docetaxel.

$^1$H NMR (CDCl$_3$) δ 1.24 (s, 3H), 1.26 (s, 3H), 1.40 (s, 9H), 1.73 (s, 6H), 1.74 (s, 3H), 2.00 (s, 3H), 2.07 (s, 3H), 2.17 (m, 1H), 2.25 (m, 1H), 2.36 (m, 1H), 2.48 (m, 1H), 2.93 (s, 3H), 2.94 (s, 3H), 3.79 (s, 3H), 3.86 (s, 1H), 3.92 (s, 3H), 4.02 (d, J=6.0 Hz, 1H), 4.28 (m, 2H), 4.31 (d, J=7.6 Hz, 1H), 4.80 (m, 2H), 4.89 (d, J=6.0 Hz, 1H), 4.90 (s, 1H), 4.97 (d, J=9.6 Hz, 1H), 5.28 (d, J=8.4 Hz, 1H), 5.67 (d, J=6.0 Hz, 1H), 5.70 (d, J=6.0 Hz, 1H), 6.02 (t, J=8.4 Hz, 1H), 6.94 (d, J=9.2 Hz, 1H), 7.05 (dd, J=3.2 9.2 Hz, 1H), 7.29 (d, J=3.2 Hz, 1H). m/z LC/MS for C$_{46}$H$_{64}$N$_2$O$_{16}$Na$^+$: calcd: 923.4. found: 923.4.

3'-(2-furyl) series

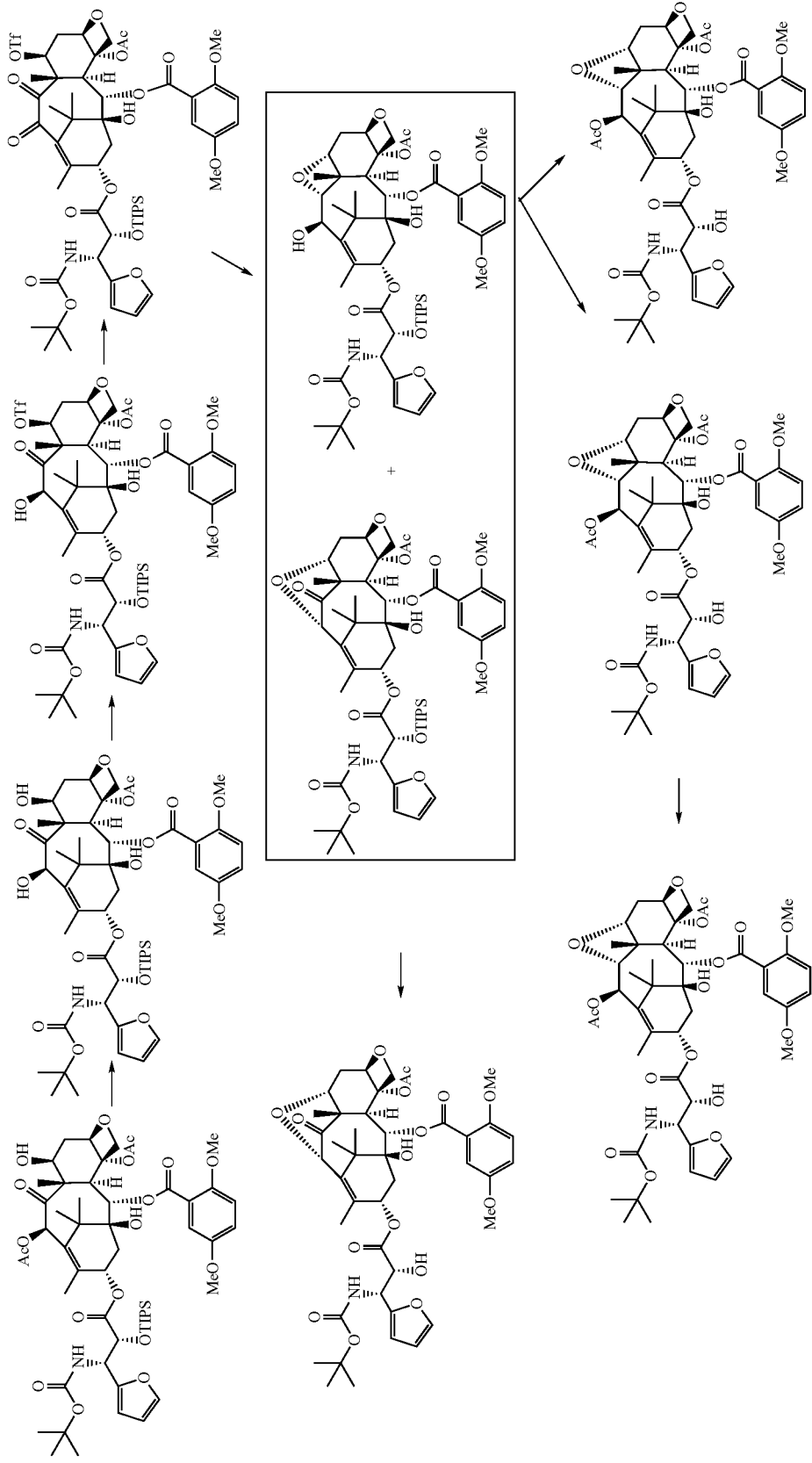

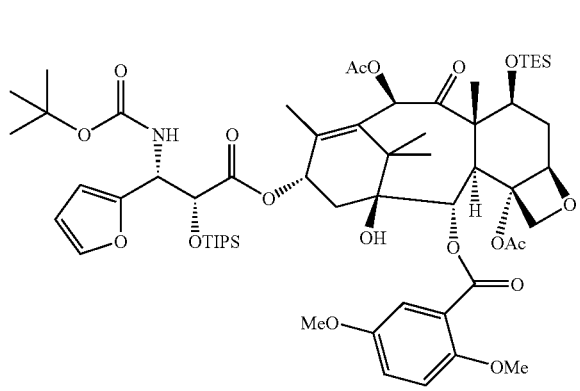

C₆₀H₉₁NO₁₈Si₂
Exact Mass: 1169.58

10-Acetoxy-7-(triethylsilyl)-2'-(triisopropylsily-loxy)-3'-dephenyl-3'-(2-furyl)-2-debenzoyl-2-(2,5-dimethoxybenzoyl)-docetaxel A mixture of (3R,4S)-1-tert-butoxycarbonyl)-3-triisopropylsilyloxy-4-(2-furyl)-azetidin-2-one (1.27 g, 3.11 mmol) and 7-(triethylsilyl)-2-debenzoyl-2-(2,5-dimethoxybenzoyl)-baccatin III (1.9 g, 2.5 mmol) were dissolved in anhydrous THF (20 mL). The mixture was cooled to −40° C. and 1.0 M LiHMDS (3.5 mL, 3.5 mmol) was added dropwise. The reaction was allowed to stir between −40 and −20° C. for 1 hour, after which it was complete. The reaction was quenched with saturated aqueous ammonium chloride and extracted into ethyl acetate (100 mL×2). The combined organic layers were washed with water (30 mL×1), dried over magnesium sulfate and concentrated in vacuo. The crude residue was purified on a silica gel column with 30% ethyl acetate in hexanes as the eluant, yielding 10-Acetoxy-7-(triethylsilyl)-2'-(triisopropylsilyloxy)-3'-dephenyl-3'-(2-furyl)-2-debenzoyl-2-(2,5-dimethoxybenzoyl)-docetaxel as a white solid (2.88 g, 98%): ¹H NMR (CDCl₃) δ 0.53 (m, 6H), 0.89 (m, 30H), 1.18 (s, 6H), 1.36 (s, 9H), 1.69 (s, 3H), 1.85 (m, 1H), 1.96 (s, 3H), 2.11 (s, 3H), 2.25 (s, 3H), 2.35 (m, 2H), 2.46 (m, 1H), 3.33 (s, 1H), 3.71 (s, 3H), 3.72 (d, J=6.8 Hz, 1H), 3.87 (s, 3H), 4.22 (d, J=8.0 Hz, 1H), 4.40 (m, 2H), 4.84 (d, J=8.0, 1H), 4.89 (d, J=1.2 Hz, 1 H), 5.24 (m, 2H), 5.61 (d, J=6.8 Hz, 1H), 6.12 (t, J=8.4 Hz, 1H), 6.18 (d, J=3.2 Hz, 1H), 6.27 (dd, J=3.2, 2.0 Hz, 1H), 6.41 (s, 1H), 6.88 (d, J=9.2 Hz, 1H), 6.97 (dd, J=9.2, 3.2 Hz, 1H), 7.20 (d, J=3.2 Hz, 1H), 7.28 (br s, 1H). m/z LC/MS for C₆₀H₉₁NO₁₈Si₂Na⁺: calcd: 1192.6. found: 1192.3.

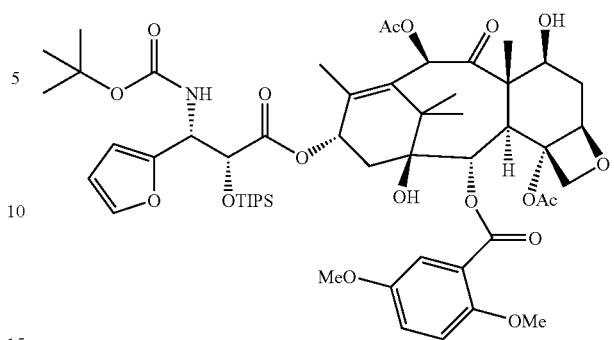

C₅₄H₇₇NO₁₈Si
Exact Mass: 1055.49

10-Acetoxy-2'-(triisopropylsilyloxy)-3'-dephenyl-3'-(2-furyl)-2-debenzoyl-2-(2,5-dimethoxybenzoyl)-docetaxel 10-Acetoxy-7-(triethylsilyl)-2'-(triisopropylsilyloxy)-3'-dephenyl-3'-(2-furyl)-2-debenzoyl-2-(2,5-dimethoxybenzoyl)-docetaxel (670 mg, 0.57 mmol) was dissolved in ethanol (2.5 mL). A solution of 5% hydrochloric acid in ethanol (5.0 mL) was added dropwise. The reaction was allowed to stir at room temperature for 5 h, after which it was complete. The reaction was quenched with saturated aqueous sodium bicarbonate and the product was extracted into ethyl acetate (75 mL×2). The combined ethyl acetate layers were washed with water (25 mL×1) and brine (25 mL×1), dried over magnesium sulfate and concentrated in vacuo. The crude 10-Acetoxy-2'-(triisopropylsilyloxy)-3'-dephenyl-3'-(2-furyl)-2-debenzoyl-2-(2,5-dimethoxybenzoyl)-docetaxel was used without purification: ¹H NMR (CDCl₃) δ 0.92 (m, 21H), 1.12 (s, 3H), 1.25 (s, 3H), 1.39 (s, 9H), 1.70 (s, 3H), 1.85 (m, 4H), 2.19 (s, 3H), 2.27 (s, 3H), 2.37 (m, 2H), 2.51 (m, 1H), 3.33 (s, 1H), 3.74 (m, 4H), 3.89 (s, 3H), 4.26 (d, J=8.4, 1H), 4.38 (m, 2H), 4.90 (m, 2H), 5.24 (m, 2H), 5.62 (d, J=6.8 Hz, 1H), 6.19 (m, 2H), 6.30 (m, 2H), 6.88 (d, J=9.2,1H), 7.00 (dd, J=9.2, 3.2 Hz, 1H), 7.21 (d, J=3.2 Hz, 1 H), 7.30 (br s, 1H). m/z LC/MS for C₅₄H₇₇NO₁₈SiNa⁺: calcd: 1078.5. found: 1078.3.

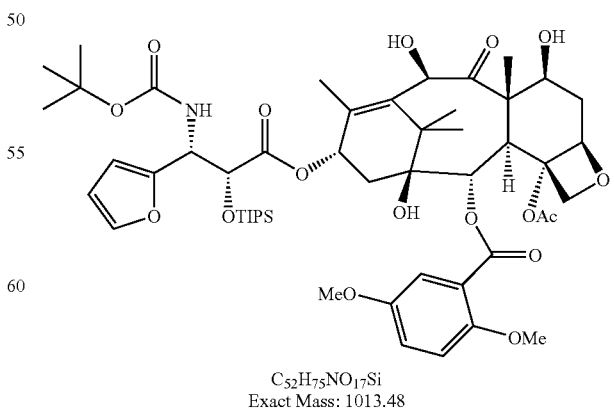

C₅₂H₇₅NO₁₇Si
Exact Mass: 1013.48

2'-(triisopropylsilyloxy)-3'-dephenyl-3'-(2-furyl)-2-debenzoyl-2-(2,5-dimethoxybenzoyl)-docetaxel 10-Acetoxy-2'-(triisopropylsilyloxy)-3'-dephenyl-3'-(2-furyl)-2-debenzoyl-2-(2,5-dimethoxybenzoyl)-docetaxel (605 mg, 0.573 mmol) was dissolved in ethanol (12.0 mL). Hydrazine monohydrate (5.0 mL) was added dropwise over 5 min, after which the reaction was complete. The reaction was diluted with ethyl acetate and quenched with saturated aqueous ammonium chloride. The product was extracted into ethyl acetate (75 mL×2), washed with water (25 mL×1) and brine (25 mL×1), dried over anhydrous sodium sulfate and concentrated in vacuo. The crude residue was purified on a silica gel column with 40% ethyl acetate in hexanes as the eluant, yielding 2'-(triisopropylsilyloxy)-3'-dephenyl-3'-(2-furyl)-2-debenzoyl-2-(2,5-dimethoxybenzoyl)-docetaxel as a white solid (507.6 mg, 87%, two steps): $^1$H NMR (CDCl$_3$) δ 0.95 (m, 21H), 1.11 (s, 3H), 1.24 (s, 3H), 1.40 (s, 9 H), 1.79 (s, 3H), 1.86 (m, 1H), 1.91 (s, 3H), 2.29 (s, 3H), 2.36 (m, 2H), 2.57 (m, 1 H), 3.29 (br s, 1H), 3.76 (s, 3H), 3.88 (d, J=6.8 Hz, 1H), 3.92 (s, 3H), 4.19 (m, 2 H), 4.43 (d, J=8.4 Hz, 1H), 4.45 (d, J=8.4 Hz, 1H), 4.91 (m, 2H), 5.24 (m, 3H), 5.65 (d, J=6.8 Hz, 1H), 6.21 (m, 2H), 6.31 (dd, J 3.2, 1.6, 1H), 6.90 (d, J=9.2 Hz, 1H), 7.02 (dd, J=9.2, 3.2 Hz, 1H), 7.23 (d, J=3.2 Hz, 1H), 7.30 (br s, 1H). m/z LC/MS for $C_{52}H_{75}NO_{17}SiNa^+$: calcd: 1036.5. found: 1036.3.

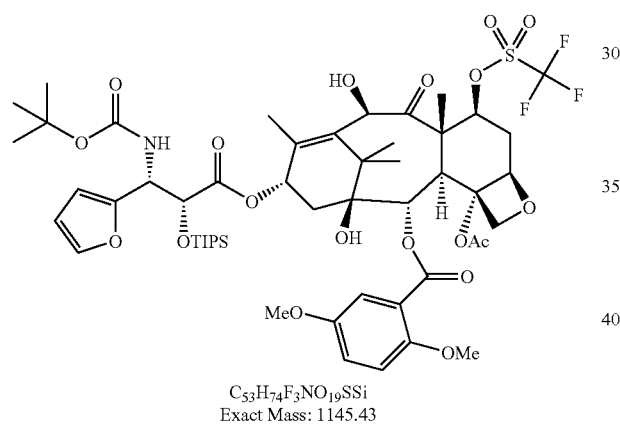

$C_{53}H_{74}F_3NO_{19}SSi$
Exact Mass: 1145.43

7-(trifluoromethanesulfonyloxy)-2'-(triisopropylsilyloxy)-3'-dephenyl-3'-(2-furyl)-2-debenzoyl-2-(2,5dimethoxybenzoyl)-docetaxel 2'-(triisopropylsilyloxy)-3'-dephenyl-3'-(2-furyl)-2-debenzoyl-2-(2,5-dimethoxybenzoyl)-docetaxel (1.7 g, 1.68 mmol) was dissolved in methylene chloride (10.0 mL) and cooled to −30° C. Pyridine (0.68 mL, 8.4 mmol) was added, followed by triflic anhydride (0.57 mL, 3.4 mmol) in methylene chloride (0.5 mL), turning the reaction yellow. The reaction was allowed to warm to 0° C. slowly over 1 h, at which point it was complete. The product was extracted into ethyl acetate (150 mL×1), washed with water (50 mL×1) and brine (50 mL×1), dried over magnesium sulfate and concentrated in vacuo. The crude reside was purified on a silica gel column with 25% ethyl acetate in hexanes as the eluant, yielding 7-(trifluoromethanesulfonyloxy)-2'-(triisopropylsilyloxy)-3'-dephenyl-3'-(2-furyl)-2-debenzoyl-2-(2,5-dimethoxybenzoyl)-docetaxel as a white solid(1.44 g, 75%): $^1$H NMR (CDCl$_3$) δ 0.94 (m, 21H), 1.09 (s, 3H), 1.22 (s, 3H), 1.39 (s, 9H), 1.92 (m, 6H), 2.30 (m, 5H), 2.40 (m, 1H), 2.79 (m, 1H), 3.44 (s, 1H), 3.74 (s, 3H), 3.91 (s, 3H), 3.95 (d, J=6.4 Hz, 1H), 4.01 (d, J=1.6 Hz, 1H), 4.30 (d, J=8.4 Hz, 1H), 4.42 (d, J=8.4 Hz, 1H), 4.89 (m, 2H), 5.24 (m, 2H), 5.36 (m, 2H), 5.64 (d, J=6.4 Hz, 1H), 6.21 (m, 2H), 6.30 (dd, J=3.2, 1.6 Hz, 1H), 6.90 (d, J=9.2 Hz, 1H), 7.02 (dd, J=9.2, 3.2 Hz, 1 H), 7.19 (d, J=3.2 Hz, 1H), 7.30 (br s, 1H). m/z LC/MS for $C_{53}H_{74}F_3NO_{19}SSiNa^+$: calcd: 1168.4. found: 1168.4.

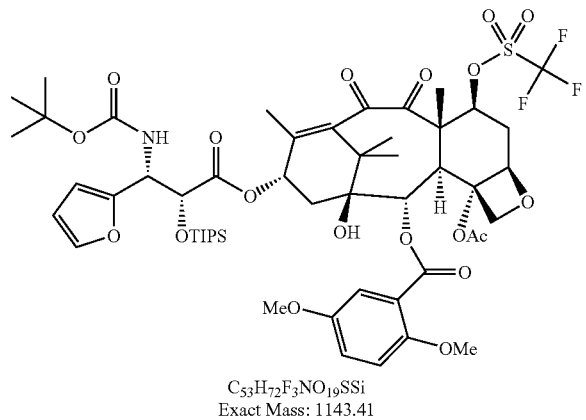

$C_{53}H_{72}F_3NO_{19}SSi$
Exact Mass: 1143.41

7-(trifluoromethanesulfonyloxy)-2'-(triisopropylsilyloxy)-3'-dephenyl-3'-(2-furyl)-10-oxo-2-debenzoyl-2-(2,5-dimethoxybenzoyl)-docetaxel To a stirred solution of 7-(trifluoromethanesulfonyloxy)-2'-(triisopropylsilyloxy)-3'-dephenyl-3'-(2-furyl)-2-debenzoyl-2-(2,5-dimethoxybenzoyl)-docetaxel (1.44 g, 1.26 mmol) in methylene chloride (30 mL) was added 4-methylmorpholine N-oxide (NMO) (590 mg, 5 mmol) followed by the addition of tetrapropylammonium perruthenate (TPAP) (62 mg, 0.18 mmol). The resulting mixture was allowed to stir at room temperature with monitoring. After 8 hours the reaction was filtered through celite and the pad of celite was rinsed with methylene chloride. The combined supernatent was concentrated in vacuo and the resulting residue was purified on a silica gel column using 10% ethyl acetate in hexane. The fractions containing the product were pooled and concentrated to give 619 mg of 7-(trifluoromethanesulfonyloxy)-2'-(triisopropylsilyloxy)-3'-dephenyl-3'-(2-furyl)-10-oxo-2-debenzoyl-2-(2,5-dimethoxybenzoyl)-docetaxel as a solid. $^1$H NMR (CDCl$_3$) δ 0.91 (m, 21H), 1.15 (s, 3H), 1.25(s, 3H), 1.37 (s, 9H), 1.89 (s, 6H), 2.14 (m, 1H), 2.27 (s, 3H), 2.32 (m, 1 H) 2.51, (m, 1H), 2.79 (m, 1H), 3.67 (d, J=6.4 Hz, 1H), 3.73 (s, 3H), 3.85 (s, 1H), 3.91 (s, 3H), 4.38 (d, J=8.4 Hz, 1H), 4.40 (d, J=8.4 Hz, 1H), 4.81 (d, J=8.8 z, 1 H), 4.89 (d, J=1.2 Hz, 1H), 5.17 (m, 1H), 5.24 (m, 2H), 5.72 (d, J=6.0 Hz, 1H), 6.14 (t, J=8.8 Hz, 1H), 6.20 (d, J=3.2 Hz, 1H), 6.28 (d, J=3.2,1.6 Hz, 1H), 6.90 (d, J=9.2 Hz, 1H), 7.01 (dd, J=9.2, 3.2 Hz, 1H), 7.15 (d, J=3.2 Hz, 1H), 7.29 (br s, 1H). m/z LC/MS for $C_{53}H_{72}F_3NO_{19}SSiNa^+$: calcd: 1166.4. found: 1166.1.

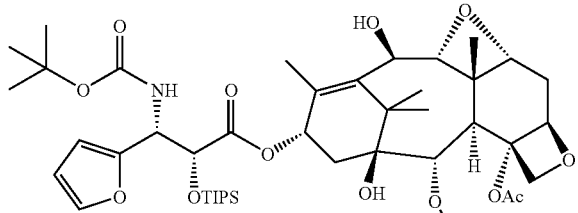

C₅₂H₇₅NO₁₆Si
Exact Mass: 997.49

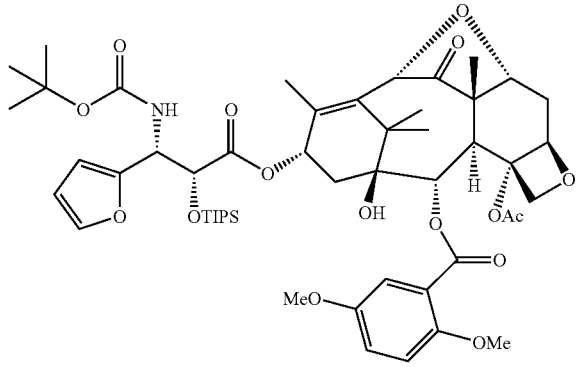

C₅₂H₇₃NO₁₆Si
Exact Mass: 995.47

7α,9α-epoxy-2'-(triisopropylsilyloxy)-3'-dephenyl-3'-(2-furyl)-2-debenzoyl-2-(2,5-dimethoxybenzoyl)-docetaxel and 7α,10α-epoxy-2'-(triisopropylsilyloxy)-3'-dephenyl-3'-(2-furyl)-2-debenzoyl-2-(2,5-dimethoxybenzoyl)-docetaxel Sodium borohydride (102 mg, 2.7 mmol) was added to the 7-(trifluoromethanesulfonyloxy)-2'-(triisopropylsilyloxy)-3'-dephenyl-3'-(2-furyl)-10-oxo-2-debenzoyl-2-(2,5-dimethoxybenzoyl)-docetaxel (618 mg, 0.54 mmol) dissolved in ethanol (7.0 mL). After 5 min, the reaction was complete and diluted with ethyl acetate. The product was extracted into ethyl acetate (100 mL×1), washed with saturated aqueous sodium chloride (50 mL×1), dried over anhydrous sodium sulfate and concentrated in vacuo. The crude residue was purified on a silica gel column with 50% ethyl acetate in hexanes as the eluant, yielding the 7α,9α-epoxy-2'-(triisopropylsilyloxy)-3'-dephenyl-3'-(2-furyl)-2-debenzoyl-2-(2,5-dimethoxybenzoyl)-docetaxel (258 mg, 48%) and 7α,10α-epoxy-2'-(triisopropylsilyloxy)-3'-dephenyl-3'-(2-furyl)-2-debenzoyl-2-(2,5-dimethoxybenzoyl)-docetaxel (231 mg, 43%).

7α,9α-epoxy-2'-(triisopropylsilyloxy)-3'-dephenyl-3'-(2-furyl)-2-debenzoyl-2-(2,5-dimethoxybenzoyl)-docetaxel $^1$H NMR (CDCl₃) δ 0.92 (m, 21 H), 1.08 (s, 3H), 1.23 (s, 3H), 1.41 (s, 9H), 1.77 (s, 3H), 1.99 (s, 3H), 2.15 (s, 3 H), 2.33 (m, 4H), 2.56 (d, J=6.8 Hz, 1H), 3.55 (s, 1H), 3.76 (s, 3H), 3.93 (s, 3H), 4.01 (d, J=6.0 Hz, 1, H), 4.25 (d, J=7.2 Hz, 1H), 4.32 (d, J=7.2 Hz, 1H), 4.77 (m, 3H), 4.92 (br s, 1H), 4.95 (br s, 1H), 5.27 (m, 2H), 5.64 (d, J=6.4 Hz, 1H), 6.06 (t, J=8.8 Hz, 1H), 6.20 (d, J=2.8 Hz, 1H), 6.29 (dd, J=3.2, 2.0 Hz, 1H), 6.90 (d, J=9.2 Hz, 1H), 7.00 (dd, J=9.2, 3.2 Hz, 1H), 7.23 (d, J=3.2 Hz, 1H), 7.31 (s, 1H). m/z LC/MS for C₅₂H₇₅NO₁₆SiNa⁺: calcd: 1020.5. found: 1020.4.

7α,10α-epoxy-2'-(triisopropylsilyloxy)-3'-dephenyl-3'-(2-furyl)-2-debenzoyl-2-(2,5-dimethoxybenzoyl)-docetaxel $^1$H NMR (CDCl₃) δ 0.95 (m, 21 H), 1.15 (s, 3H), 1.31 (s, 3H), 1.39 (s, 9H), 1.83 (m, 6H), 2.11 (s, 3H), 2.20-2.36 (m, 4H), 3.62 (m, 2H), 3.75 (s, 3H), 3.89 (s, 3H), 4.40 (m, 3H), 4.78 (br s, 1H), 4.92 (br s, 1H), 5.06 (d, J=4.0 Hz, 1H), 5.25 (m, 2H), 5.36 (d, J=6.0 Hz, 1H), 6.18 (m, 2H), 6.27 (dd, J=2.8, 1.6 Hz, 1H), 6.88 (d, J=9.2 Hz, 1H), 6.99 (dd, J=9.2, 3.2 Hz, 1H), 7.22 (d, J=3.2 Hz, 1H), 7.29 (br s, 1H). m/z LC/MS for C₅₂H₇₃NO₁₆SiNa⁺: calcd: 1018.5. found: 1018.4.

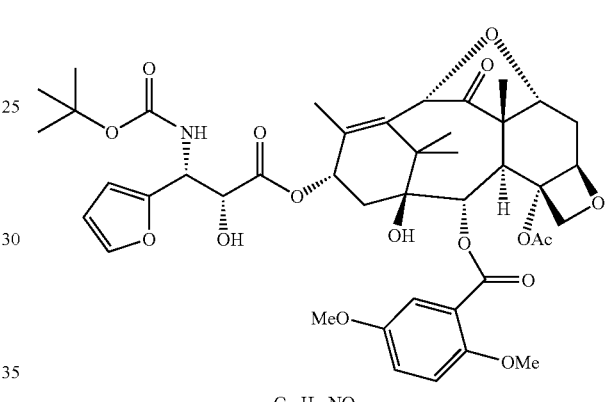

C₄₃H₅₃NO₁₆
Exact Mass: 839.34

7α,10α-epoxy-3'-dephenyl-3'-(2-furyl)-2-debenzoyl-2-(2,5-dimethoxybenzoyl)-docetaxel 7α,10α-epoxy-2'-(triisopropylsilyloxy)-3'-dephenyl-3'-(isobutenyl)-2-debenzoyl-2-(2,5-dimethoxybenzoyl)-docetaxel (49.1 mg, 0.049 mmol) was dissolved in pyridine-acetonitrile (1/1, 2.0 mL) and cooled to 0° C. HF/pyridine (70/30, 0.5 mL) was added and the reaction was allowed to warm to room temperature slowly overnight. The reaction was quenched with saturated aqueous sodium bicarbonate and diluted with ethyl acetate. The ethyl acetate layer was washed with additional saturated aqueous sodium bicarbonate (15 mL×2) and the combined aqueous layers were then washed with ethyl acetate (40 mL×2). The combined ethyl acetate layers were washed with water (15 mL×2), dried over anhydrous sodium sulfate and concentrated in vacuo. Crude residue was purified over silica gel with 50% ethyl acetate in hexanes as the eluant, yielding 7α,10α-epoxy-3'-dephenyl-3'-(2-furyl)-2-debenzoyl-2-(2,5-dimethoxybenzoyl)-docetaxel (33.5 mg, 81%): $^1$H NMR (CDCl₃) δ 1.16 (s, 3H), 1.30 (s, 3H), 1.40 (s, 9H), 1.79 (s, 3H), 1.87 (s, 3H), 2.03 (s, 3H), 2.06 (m, 1H), 2.34 (m, 3H), 3.58 (s, 1H), 3.66 (dd, J=7.2, 2.8 Hz, 1H), 3.78 (s, 3H), 3.88 (s, 3H), 3.93 (d, J=4.0 Hz, 1H), 4.34 (m, 2H), 4.49 (d, J=7.6 Hz, 1H), 4.67 (d, J=2.0 Hz, 1H), 4.81 (br s, 1H), 5.04 (d, J=2.0 Hz, 1H), 5.34 (m, 3H), 6.18 (br s, 1H), 6.26 (d, J=3.2 Hz, 1H), 6.31 (dd, J=3.2, 2.0 Hz, 1H), 6.92 (d, J=9.2 Hz, 1H), 7.03 (dd, J=9.2, 3.2 Hz, 1H), 7.24 (d, J=3.2 z, 1H), 7.34 (d, J=1.2 Hz, 1H). m/z LC/MS for $C_{43}H_{53}NO_{16}Na^+$: calcd: 862.3. found: 862.3.

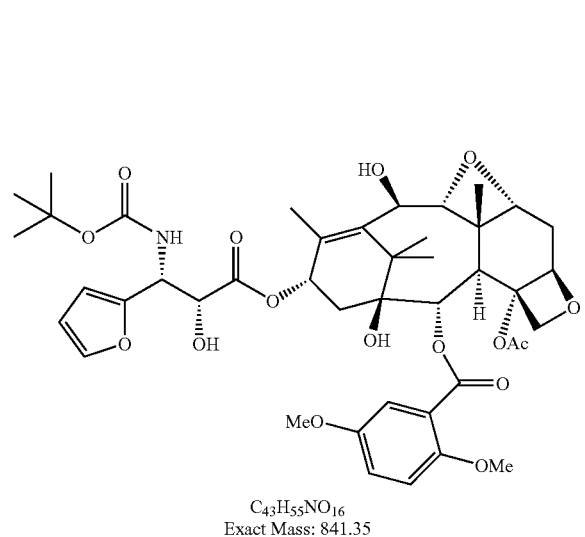

7α,9α-epoxy-3'-dephenyl-3'-(2-furyl)-2-debenzoyl-2-(2,5-dimethoxybenzoyl)-docetaxel 7α,9α-epoxy-2'-(triisopropylsilyloxy)-3'-dephenyl-3'-(2-furyl)-2-debenzoyl-2-(2,5-dimethoxybenzoyl)-docetaxel was dissolved in pyridine-acetonitrile (1/1, 1.5 mL) and cooled to 0° C. HF/pyridine (70:30, 0.2 mL) was added and the reaction was allowed to warm to room temperature slowly overnight. The reaction was quenched with saturated aqueous sodium bicarbonate and diluted with ethyl acetate. The ethyl acetate layer was washed with additional saturated aqueous sodium bicarbonate (10 mL×2). The combined aqueous layers were washed with ethyl acetate (20 mL×2). The combined ethyl acetate layers were then washed with water (10 mL×2), dried over anhydrous sodium sulfate and concentrated in vacuo. Crude residue was purified over silica gel with 75% ethyl acetate in hexanes as the eluant yielding 7α,9α-epoxy-3'-dephenyl-3'-(2-furyl)-2-debenzoyl-2-(2,5-dimethoxybenzoyl)-docetaxel as a white solid (10.26 mg, 70%): $^1$H NMR (CDCl$_3$) δ 1.09 (s, 3H), 1.23 (s, 3H), 1.40 (s, 9H), 1.77 (s, 3H), 1.95 (s, 3H), 2.07 (s, 3H), 2.21 (m, 2H), 2.37 (m, 2H), 2.50 (d, J=6.0 Hz, 1H), 3.51 (s, 1H), 3.71 (d, J=4.0 Hz, 1H), 3.77 (s, 3H), 3.91 (s, 3H), 4.02 (d, J=6.4 Hz, 1H), 4.26 (d, J=7.2 Hz, 1H), 4.29 (d, J=7.2 Hz, 1H), 4.68 (d, J=2.8 Hz, 1H), 4.78 (m, 3H), 4.88 (br s, 1H), 5.32 (m 2H), 5.63 (d, J=6.4Hz, 1H), 6.01 (t, J=8.8 Hz, 1H), 6.27 (d, J=3.2Hz, 1 H), 6.31 (dd, J=3.2, 2.0 Hz, 1H), 6.92 (d, J=9.2 Hz, 1H), 7.20 (dd, J=9.2, 3.2 Hz, 1H), 7.24 (d, J=3.2 Hz, 1H), 7.34 (d, J=0.8 Hz, 1H). m/z LC/MS for $C_{43}H_{55}NO_{16}Na^+$: calcd: 864.5. found: 864.3.

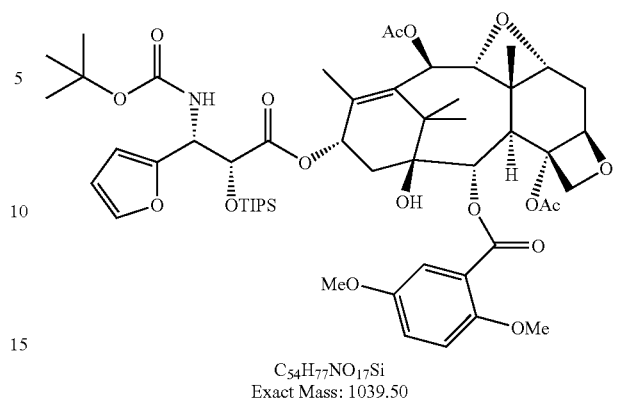

7α,9α-epoxy-2'-(triisopropylsilyloxy)-3'-dephenyl-3'-(2-furyl)-2-debenzoyl-2-(2,5-dimethoxybenzoyl)-10-acetoxy-docetaxel Acetic anhydride (8.1 μL, 0.858 mmol) and DMAP (5 mg, 0.043 mmol) were added to a solution of 7α,9α-epoxy-2'-(triisopropylsilyloxy)-3'-dephenyl-3'-(2-furyl)-2-debenzoyl-2-(2,5-dimethoxybenzoyl)-docetaxel (28.5 mg, 0.0286 mmol) in pyridine (0.5 mL). The reaction was complete after stirring at room temperature for 3 hours. Product was extracted into ethyl acetate (30 mL×1), washed with water (15 mL×1) and brine (15 mL×1), dried over anhydrous sodium sulfate and concentrated in vacuo. Crude residue was purified over silica gel with 50% ethyl acetate in hexanes as the eluant, yielding 7α,9α-epoxy-2'-(triisopropylsilyloxy)-3'-dephenyl-3'-(2-furyl)-2-debenzoyl-2-(2,5-dimethoxybenzoyl)-10-acetoxy-docetaxel as a white solid (25 mg, 85%) $^1$H NMR (CDCl$_3$) δ 0.95 (m, 21H), 1.26 (m, 6H), 1.44 (s, 9H), 1.76 (s, 3H), 1.99 (s, 3 H), 2.13 (s, 3H), 2.18 (s. 3H), 2.40 (m, 4H), 3.66 (s, 1H), 3.80 (s, 3H), 3.97 (s, 3 H), 4.02 (d, J=6.4 Hz, 1H), 4.27 (d, J=7.2 Hz, 1H), 4.35 (d, J=7.2 Hz, 1H), 4.82 (dd, J=8.4, 6.0 Hz, 1H), 4.86 (d, J=6.0 Hz, 1H), 4.95 (br s, 1H), 5.01 (s, 1H), 5.31 (s, 2H), 5.72 (m, 2H), 6.01 (t, J=8.8 Hz, 1H), 6.24 (d, J=3.2, 1H), 6.32 (dd, J=3.2, 1.6 Hz, 1H), 6.94 (d, J=9.2 Hz, 1H), 7.05 (dd, J=9.2, 3.2 Hz, 1H), 7.27 (d, J=3.2, 1H), 7.34 (d, J=0.8 Hz, 1H). m/z LC/MS for $C_{54}H_{77}NO_{17}SiNa^+$: calcd: 1062.5. found: 1062.5.

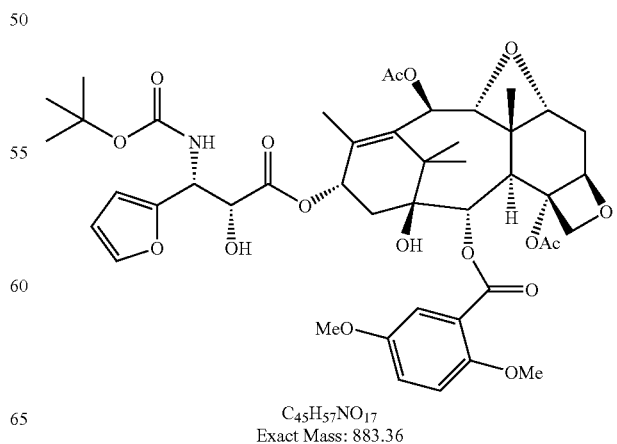

7α,9α-epoxy-3'-dephenyl-3'-(2-furyl)-2-debenzoyl-2-(2,5-dimethoxybenzoyl)-10-acetoxy-docetaxel 7α,9α-epoxy-2'-(triisopropylsilyloxy)-3'-dephenyl-3'-(2-furyl)-2-debenzoyl-2-(2,5-dimethoxybenzoyl)-10-acetoxy-docetaxel (25 mg, 0.025 mmol) was dissolved in pyridine-acetonitrile (1/1, 1.5 mL) and cooled to 0° C. HF/pyridine (70:30, 0.25 mL) was added and the reaction was allowed to warm to room temperature slowly overnight. The reaction was quenched with saturated aqueous sodium bicarbonate and diluted with ethyl acetate. The ethyl acetate layer was washed with additional saturated aqueous sodium bicarbonate (10 mL×2). The combined aqueous layers were washed with ethyl acetate (25 mL×2). The combined ethyl acetate layers were then washed with water (10 mL×2), dried over anhydrous sodium sulfate and concentrated in vacuo. Crude residue was purified over silica gel with 80% ethyl acetate in hexanes as the eluant yielding final product, 7α,9α-epoxy-3'-dephenyl-3'-(2-furyl)-2-debenzoyl-2-(2,5-dimethoxybenzoyl)-10-acetoxy-docetaxel (17.2 mg, 78%): $^1$H NMR (CDCl$_3$) δ 1.24 (s, 6, H), 1.41 (s, 9 H), 1,74 (s, 3H), 1.94 (s, 3H), 2.10 (s, 6H), 2.27 (m, 2H), 2.33 (m, 1H), 2.46 (m, 1 H), 3.62 (s, 1H), 3.79 (s, 4H), 3.93 (s, 3H), 4.01 (d, J=6.0 Hz, 1H), 4.26 (d, J=7.2 Hz, 1H), 4.30 (d, J=7.2 Hz, 1H), 4.72 (d, J=3.6 Hz, 1H), 4.80 (dd, J=5.6, 8.8 Hz 1H), 4.85 (d, J=6.0 Hz, 1H), 4.89 (br s, 1H), 5.34 (m, 2H), 5.65 (d, J=6.0 Hz, 1H), 5.70 (d, J=6.0 Hz, 1H), 6.02 (t, J=8.8 Hz, 1H), 6.29 (d, J=3.2 Hz, 1H), 6.33 (m, 1H), 6.94 (d, J=9.2 Hz, 1H), 7.05 (dd, J=9.2, 3.2 Hz, 1H), 7.26 (d, J=3.2 Hz, 1H), 7.36 (d, J=1.2 Hz, 1H). m/z LC/MS for C$_{45}$H$_{57}$NO$_{17}$Na$^+$: calcd: 906.4. found: 906.4.

3'-isobutenyl series with SS linkers

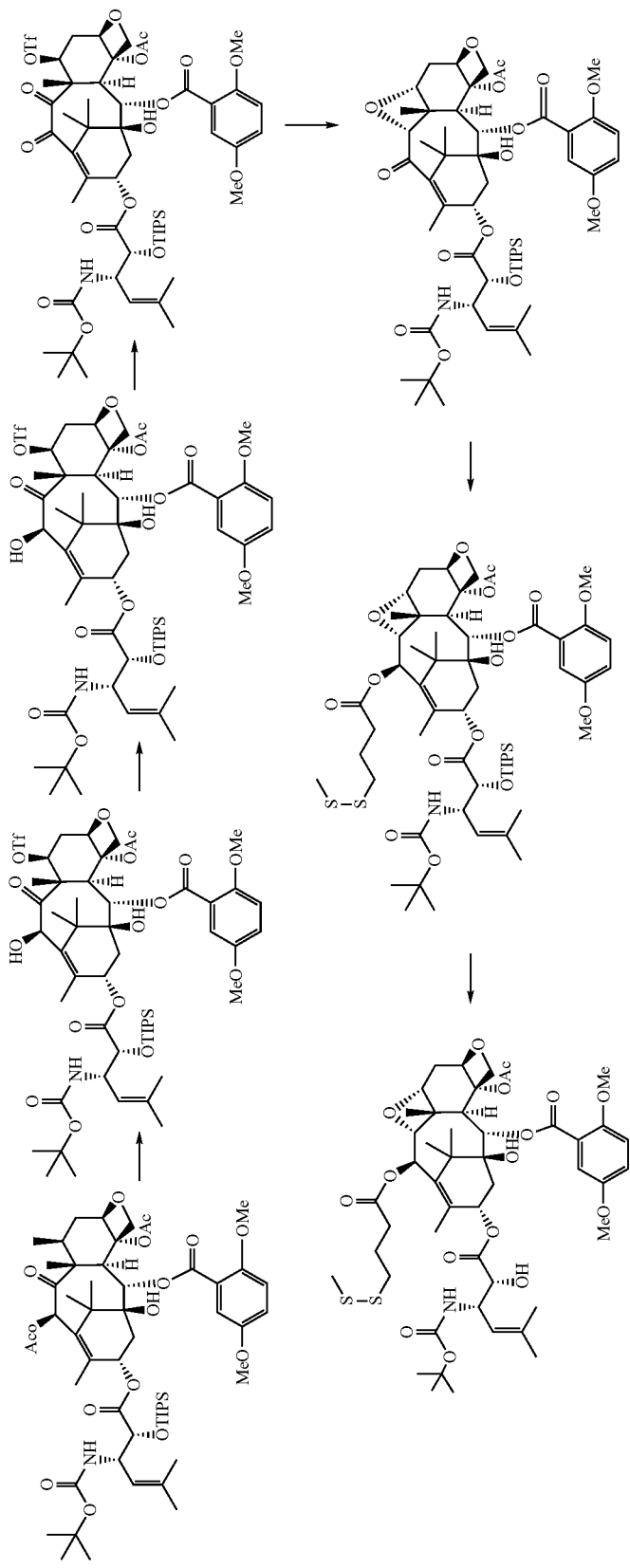

The following intermediates were previously described:

2'-(triisopropylsilyloxy)-3'-dephenyl-3'-(isobutenyl)-2-debenzoyl-2-(2,5-dimethoxybenzoyl)-docetaxel 7-(trifluoromethanesulfonyloxy)-2'-(triisopropylsilyloxy)-3'-dephenyl-3'-(isobutenyl)-2-debenzoyl-2-(2,5-dimethoxybenzoyl)-docetaxel 7-(trifluoromethanesulfonyloxy)-2'-(triisopropylsilyloxy)-3'-dephenyl-3'-(isobutenyl)-10-oxo-2-debenzoyl-2-(2,5-dimethoxybenzoyl)-docetaxel 7α,9α-epoxy-2'-(triisopropylsilyloxy)-3'-dephenyl-3'-(isobutenyl)-2-debenzoyl-2-(2,5-dimethoxybenzoyl)-docetaxel

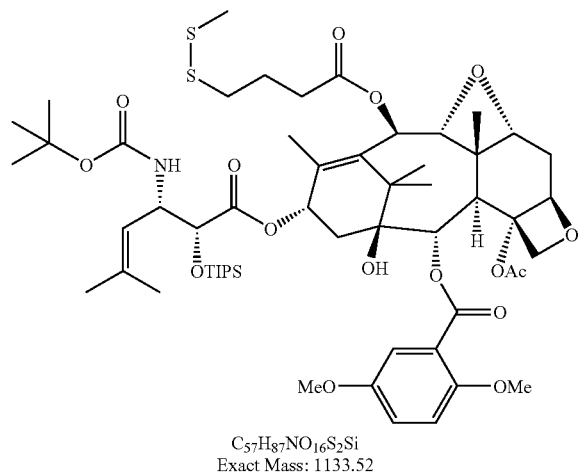

$C_{57}H_{87}NO_{16}S_2Si$
Exact Mass: 1133.52

7α,9α-epoxy-2'-(triisopropylsilyloxy)-3'-dephenyl-3'-(isobutenyl)-2-debenzoyl-2-(2,5-dimethoxybenzoyl)-10-(4-methyldithiobutanoyl)-docetaxel To a solution of 7α,9α-epoxy-2'-(triisopropylsilyloxy)-3'-dephenyl-3'-(isobutenyl)-2-debenzoyl-2-(2,5-dimethoxybenzoyl)-docetaxel (28 mg, 0.029 mmol) dissolved in methylene chloride (1.5 mL) under nitrogen was added DMAP (3.5 mg, 0.028 mmol) and 4-methyldithiobutanoic acid (50 mg, 0.28 mmol). To this mixture was added diisopropylcarbodiimide (0.045 mL, 0.28 mmol) and the resulting mixture was allowed to stir at room temperature overnight. The reaction was then quenched with ammonium chloride (15 mL) and extracted with methylene chloride (20 mL). The organic layer was then washed with brine (15 mL), dried over anhydrous sodium sulfate, filtered, and concentrated in vacuo. The residue was purified by silica ptlc using 40% ethyl acetate in hexane as the developing solvent. The band containing the desired product was scraped and rinsed with ethyl acetate at the filter. The organic layers were combined and concentrated in vacuo to give 23 mg of 7α,9α-epoxy-2'-(triisopropylsilyloxy)-3'-dephenyl-3'-(isobutenyl)-2-debenzoyl-2-(2,5-dimethoxybenzoyl)-10-(4-methyldithiobutanoyl)-docetaxel as a white solid.

$^1$H NMR (CDCl$_3$) δ 1.10 (m, 21H), 1.21 (s, 3H), 1.23 (s, 3H), 1.39 (s, 9H), 1.68 (s, 3H), 1.71 (s, 3H), 1.74 (s, 3H), 1.95 (s, 3H), 2.06 (dt, J=2.0, 7.2 Hz, 2H), 2.08 (s, 3H), 2.31 (m, 3H), 2.40 (s, 3H), 2.49 (m, 3H), 2.74 (dt, J=2.0, 7.2 Hz, 2 H), 3.80 (s, 3H), 3.98 (s, 4H), 4.25 (d, J=7.2 Hz, 1H), 4.33 (d, J=7.2 Hz, 1H), 4.46 (d, J=2.0 Hz, 1H), 4.77 (m, 2H), 4.84 (d, J=6.4 Hz, 1H), 4.92 (s, 1H), 4.92 (d, J=7.2 Hz, 1H), 5.36 (d, J=8.4 Hz, 1H), 5.71 (overlapping d, J=6.4 Hz, 2H), 5.90 (t, J=8.8 Hz, 1H), 6.95 (d, J=9.2 Hz, 1H), 7.06 (dd, J=3.2 9.2 Hz, 1H), 7.30 (d, J=3.2 Hz, 1H). m/z LC/MS for $C_{57}H_{87}NO_{16}S_2SiNa^+$: calcd: 1156.5. found: 1156.2.

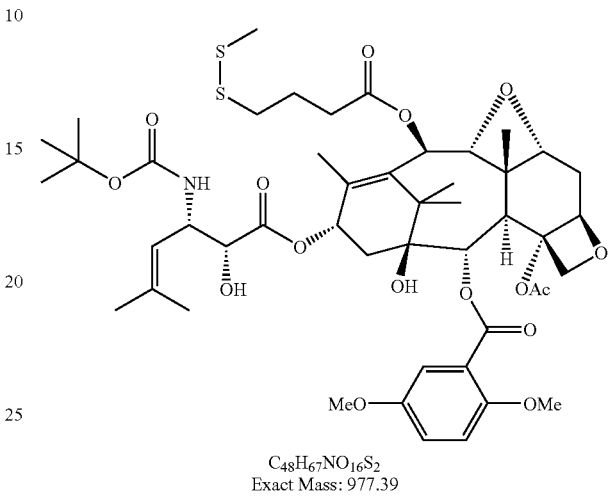

$C_{48}H_{67}NO_{16}S_2$
Exact Mass: 977.39

7α,9α-epoxy-3'-dephenyl-3'-(isobutenyl)-2-debenzoyl-2-(2,5-dimethoxybenzoyl)-10-(4-methyidithiobutanoyl)-docetaxel A solution containing 7α,9α-epoxy-2'-(triisopropylsilyloxy)-3'-dephenyl-3'-(isobutenyl)-2-debenzoyl-2-(2,5-dimethoxybenzoyl)-10-(4-methyldithiobutanoyl)-docetaxel (23 mg, 0.02 mmol) dissolved in a 1:1 mixture of acetonitrile:pyridine (1.6 mL) was cooled to 0° C. in an ice bath. To this was added hydrogen fluoride-pyridine (0.25 mL) and the solution was allowed to gradually warm to room temperature. After 16 hours the reaction was diluted with ethyl acetate (15 mL) and quenched with a saturated sodium bicarbonate solution (15 mL). The organic layer was washed once with brine (15 mL) and then dried over anhydrous sodium sulfate, filtered, and concentrated in vacuo. The crude residue was purified by silica ptlc using 65% ethyl acetate in hexane as the developing solvent. The band containing the desired product was scraped and rinsed with ethyl acetate at the filter. The organic layers were combined and concentrated in vacuo to give 16 mg of 7α,9α-epoxy-3'-dephenyl-3'-(isobutenyl)-2-debenzoyl-2-(2,5-dimethoxybenzoyl)-10-(4-methyidithiobutanoyl)-docetaxel.

$^1$H NMR (CDCl$_3$) δ 1.25 (s, 3H), 1.29 (s, 3H), 1.40 (s, 9H), 1.73 (s, 6H), 1.74 (s, 3H), 1.97 (s, 3H), 2.04 (m, 2H), 2.07 (s, 3H), 2.17 (m, 1H), 2.25 (m, 1H), 2.33 (m, 1H), 2.39 (s, 3H), 2.51 (m, 1H), 2.73 (t, J=7.2 Hz, 1H), 3.79 (s, 3H), 3.83 (s, 1H), 3.93 (s, 3H), 4.00 (d, J=6.0 Hz, 1H), 4.26 (m, 2H), 4.31 (d, J=7.6 Hz, 1H), 4.78 (m, 2H), 4.84 (d, J=6.0 Hz, 1H), 4.90 (s, 1H), 4.96 (d, J=9.2 Hz, 1 H), 5.27 (d, J=8.4 Hz, 1H), 5.68 (d, J=6.4 Hz, 1H), 5.70 (d, J=6.0 Hz, 1H), 6.00 (t, J=8.4 Hz, 1H), 6.94 (d, J=9.2 Hz, 1H), 7.05 (dd, J=3.2 9.2 Hz, 1H), 7.28 (d, J=3.2 Hz, 1H). m/z LC/MS for $C_{48}H_{67}NO_{16}S_2Na^+$: calcd: 1000.4. found: 1000.2.

3'-2-furyl series with SS linkers

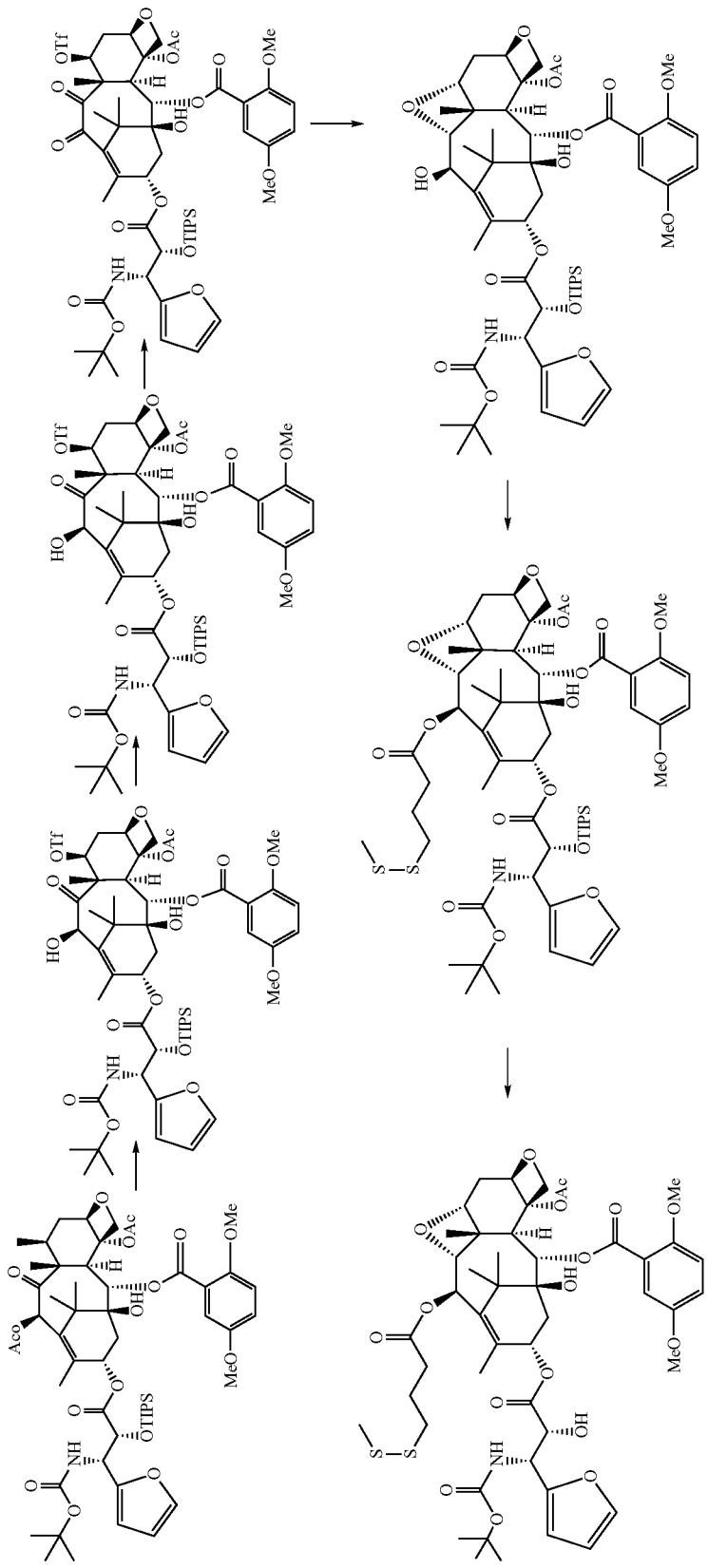

The following intermediates were previously described:

2'-(triisopropylsilyloxy)-3'-dephenyl-3'-(2-furyl)-2-debenzoyl-2-(2,5-dimethoxybenzoyl)-docetaxel 7-(trifluoromethanesulfonyloxy)-2'-(triisopropylsilyloxy)-3'-dephenyl-3'-(2-furyl)-2-debenzoyl-2-(2,5-dimethoxybenzoyl)-docetaxel 7-(trifluoromethanesulfonyloxy)-2'-(triisopropylsilyloxy)-3'-dephenyl-3'-(2-furyl)-10-oxo-2-debenzoyl-2-(2,5-dimethoxybenzoyl)-docetaxel 7α,9α-epoxy-2'-(triisopropylsilyloxy)-3'-dephenyl-3'-(2-furyl)-2-debenzoyl-2-(2,5-dimethoxybenzoyl)-docetaxel

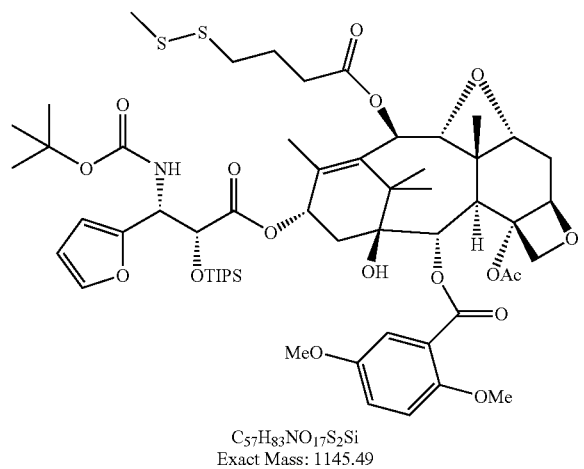

$C_{57}H_{83}NO_{17}S_2Si$
Exact Mass: 1145.49

7α,9α-epoxy-2'-(triisopropylsilyloxy)-3'-dephenyl-3'-(2-furyl)-2-debenzoyl-2-(2,5-dimethoxybenzoyl)-10-(4-methyidithiobutanoyl)-docetaxel DMAP (4.6 mg, 0.0374 mmol), 4-methyldithiobutanoic acid (62 mg, 0.374 mmol) and DIC (58.5 μL, 0.0374 mmol) were added to a solution of 7α,9α-epoxy-2'-(triisopropylsilyloxy)-3'-dephenyl-3'-(2-furyl)-2-debenzoyl-2-(2,5-dimethoxybenzoyl)-docetaxel (37.3 mg, 0.0374 mmol) in methylene chloride (0.5 mL). The reaction was allowed to stir at room temperature overnight, after which it was complete and quenched with saturated aqueous ammonium chloride. Product was extracted into ethyl acetate (25 mL×2), washed with water (15 mL×1), dried over magnesium sulfate and concentrated in vacuo. The crude residue was purified over silica gel with 50% ethyl acetate in hexane as the eluant, yielding 7α,9α-epoxy-2'-(triisopropylsilyloxy)-3'-dephenyl-3'-(2-furyl)-2-debenzoyl-2-(2,5-dimethoxybenzoyl)-10-(4-methyldithiobutanoyl)-docetaxel (48.2 mg, 100+ %): $^1$H NMR (CDCl$_3$) δ 0.92 (m, 21H), 1.24 (m, 6H), 1.41 (s, 9H), 1.73 (s, 3H), 1.95 (s, 3H), 2.05 (m, 2H), 2.15 (s, 3H), 2.32 (m, 3H), 2.38 (s, 3H), 2.44-2.56 (m 3H), 2.72 (m, 2H), 3.65 (s, 1 H), 3.77 (s, 3H), 3.94 (s, 3H), 3.98 (m, 1H), 4.26 (m, 2H), 4.77 (dd, J=8.4, 6.0 Hz, 1H), 4.83 (d, J=6.4 Hz, 1H), 4.92 (br s, 1H), 4.97 (s, 1H), 5.28 (s, 2H), 5.68 (m, 2 H), 5.98 (t, J=8.8 Hz, 1H), 6.20 (d, J=3.2 Hz, 1H), 6.29 (dd, J=3.2, 2.0 Hz, 1H), 6.90 (d, J=9.2 Hz, 1H), 7.01 (dd, J=9.2, 3.2 Hz, 1H), 7.24 (d, J=3.2 Hz, 1H), 7.31 (d, J=1.2, 1H). m/z LC/MS for $C_{57}H_{83}NO_{17}S_2SiNa^+$: calcd: 1168.5. found: 1168.4

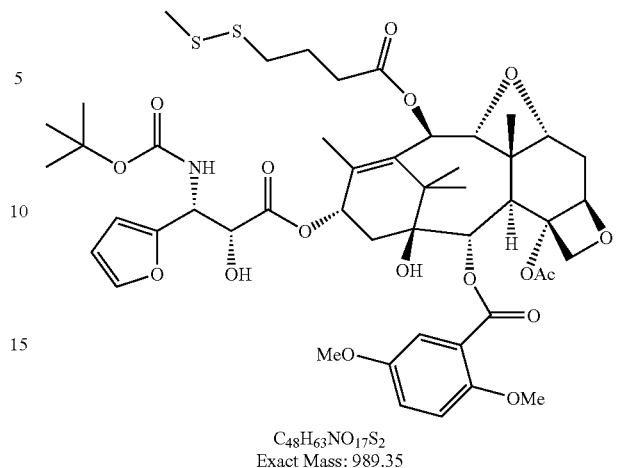

$C_{48}H_{63}NO_{17}S_2$
Exact Mass: 989.35

7α,9α-epoxy-3'-dephenyl-3'-(2-furyl)-2-debenzoyl-2-(2,5-dimethoxybenzoyl)-10-(4-methyidithiobutanoyl)-docetaxel 7α,9α-epoxy-2'-(triisopropylsilyloxy)-3'-dephenyl-3'-(2-furyl)-2-debenzoyl-2-(2,5-dimethoxybenzoyl)-10-(4-methyldithiobutanoyl)-docetaxel (42.8 mg, 0.0374 mmol) was dissolved in pyridine-acetonitrile (1/1, 3.0 mL) and cooled to 0° C. HF/pyridine (70:30, 0.5 mL) was added and the reaction was allowed to warm to room temperature slowly overnight. The reaction was quenched with saturated aqueous sodium bicarbonate and diluted with ethyl acetate. The ethyl acetate layer was washed with additional saturated aqueous sodium bicarbonate (15 mL×2) and the combined aqueous layers were then washed with ethyl acetate (40 mL×2). The combined ethyl acetate layers were washed with water (15 mL×2), dried over anhydrous sodium sulfate and concentrated in vacuo. Crude residue was purified over silica gel with 50% ethyl acetate in hexanes as the eluant yielding 7α,9α-epoxy-3'-dephenyl-3'-(2-furyl)-2-debenzoyl-2-(2,5-dimethoxybenzoyl)-10-(4-methyldithiobutanoyl)-docetaxel (22.9 mg, 62%, 2 steps): $^1$H NMR (CDCl$_3$) δ 1.24 (m, 6H), 1.41 (s, 9H), 1.74 (s, 3H), 1.93 (s, 3H), 2.04 (m, 2H), 2.09 (s, 3H), 2.24 (m, 2H), 2.33 (m, 1H), 2.37 (s, 3H), 2.42-2.56 (m, 3H), 2.72 (t, J=6.8 Hz, 2H), 3.62 (s, 1H), 3.75 (d, J=8.4 Hz, 1H), 3.78 (s, 3H), 3.93 (s, 3H), 3.99 (d, J=6.0 Hz, 1H), 4.26 (d, J=7.2 Hz, 1H), 4.30 (d, J=7.2 Hz, 1H), 4.70 (d, J=3.6 Hz, 1H), 4.77 (dd, J=8.8, 5.6 Hz, 1H), 4.83 (d, J=6.0 Hz, 1H), 4.88 (br s, 1H), 5.33 (br s, 2H), 5.67 (m, 2H), 6.01 (t, J=8.8 Hz, 1 H), 6.28 (d, J=3.2, 1H), 6.32 (dd, J=3.2, 2.0 Hz, 1H), 6.92 (d, J=9.2 Hz, 1H), 7.03 (dd, J=9.2, 3.2 Hz, 1H), 7.25 (d, J=3.2, 1H), 7.35 (m, 1H). m/z LC/MS for $C_{48}H_{63}NO_{17}S_2Na^+$: calcd: 1012.3. found: 1012.3.

The activity of the compounds of the present invention were determined following the proceeding described by Riou, Naudin and Lavelle in Biochemical and Biophysical Research Communications; Vol. 187, No1, 1992, p 164-170.

| taxoid | IGT# | A549 | MCF7 |
|---|---|---|---|
| non-disulfides | | | |
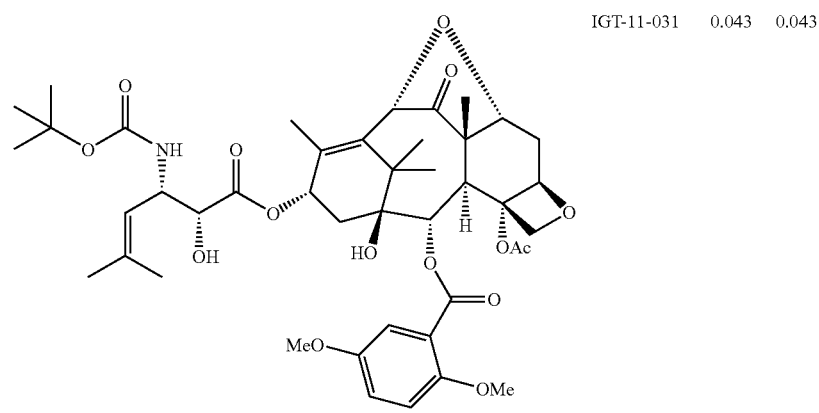
IGT-11-031  0.043  0.043
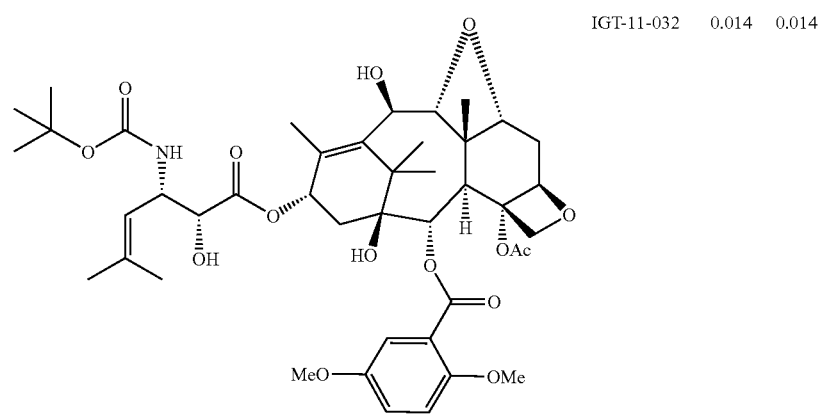
IGT-11-032  0.014  0.014
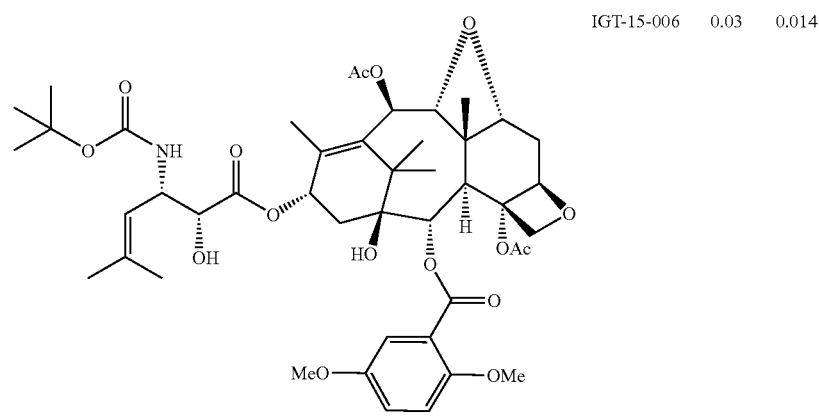
IGT-15-006  0.03  0.014

-continued
| taxoid | IGT# | A549 | MCF7 |
|---|---|---|---|
| 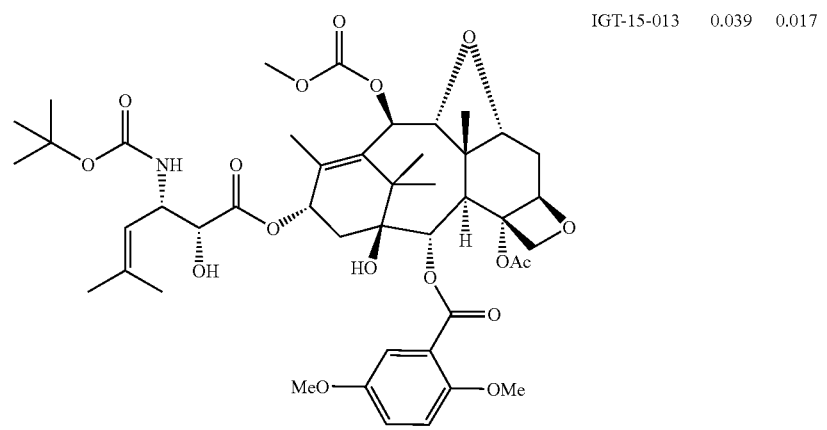 | IGT-15-013 | 0.039 | 0.017 |
| 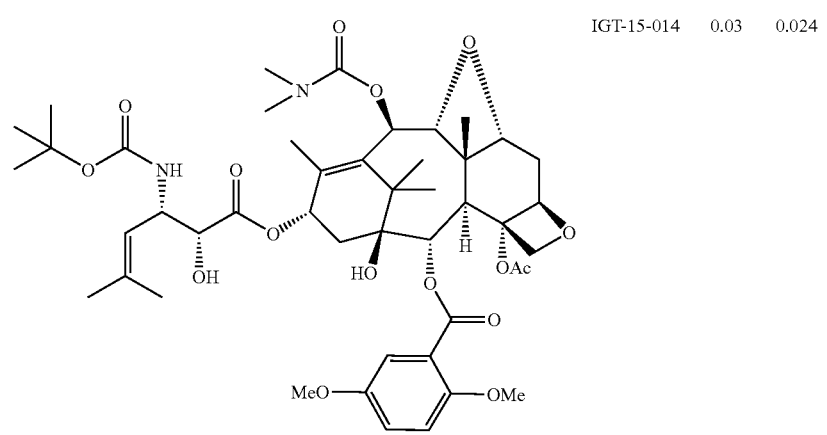 | IGT-15-014 | 0.03 | 0.024 |
| 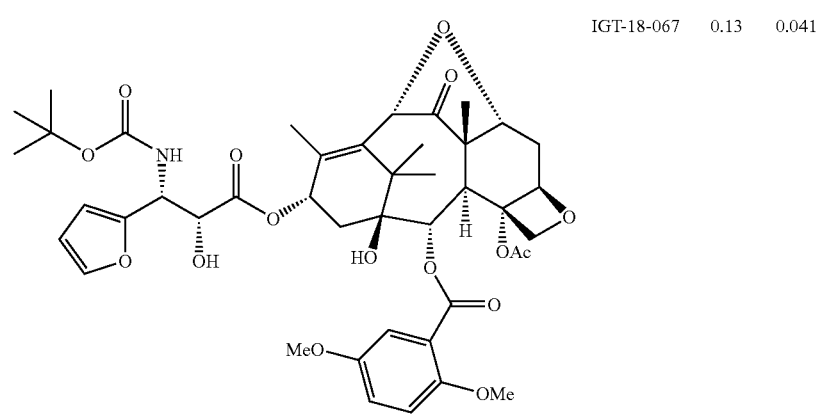 | IGT-18-067 | 0.13 | 0.041 |

-continued
| taxoid | IGT# | A549 | MCF7 |
|---|---|---|---|
| 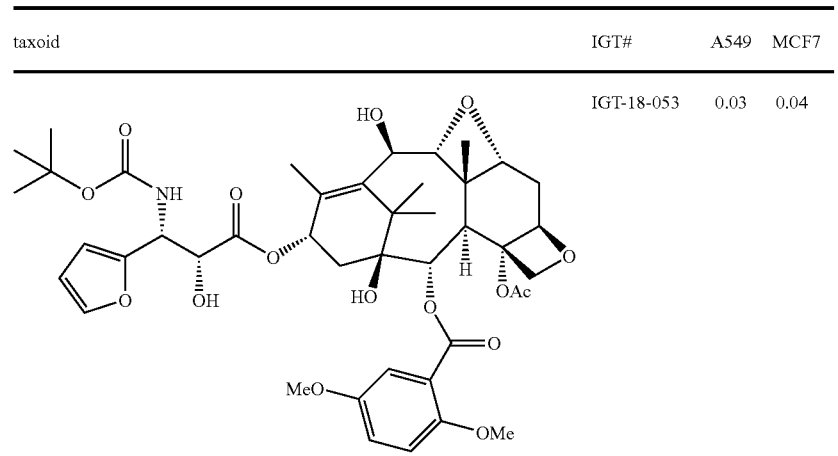 | IGT-18-053 | 0.03 | 0.04 |
| 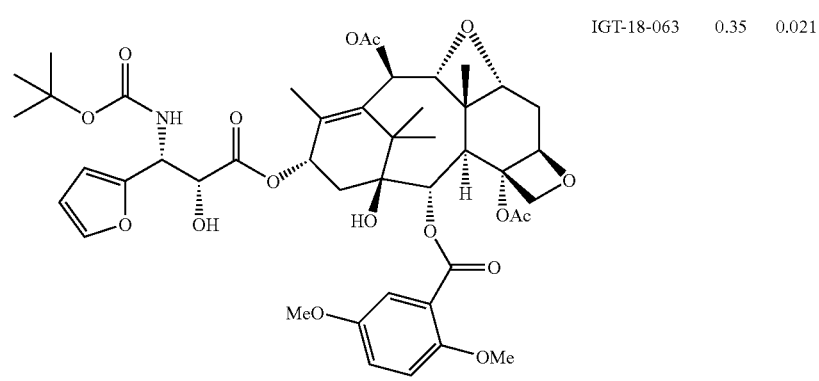 | IGT-18-063 | 0.35 | 0.021 |
disulfides
| | | | |
|---|---|---|---|
| 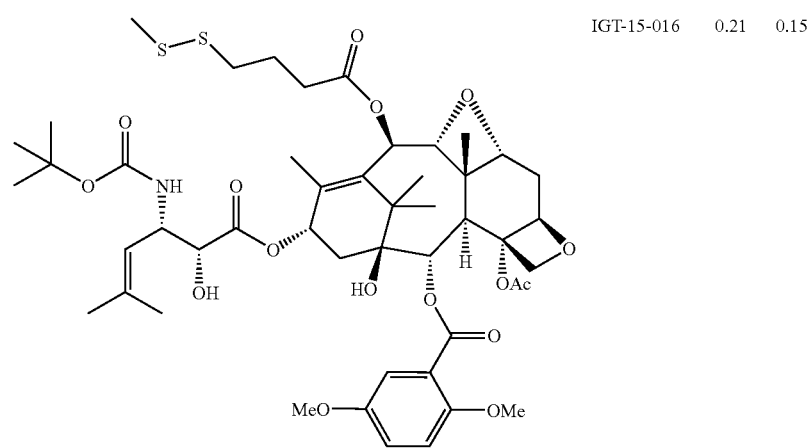 | IGT-15-016 | 0.21 | 0.15 |

| taxoid | IGT# | A549 | MCF7 |
|---|---|---|---|
| 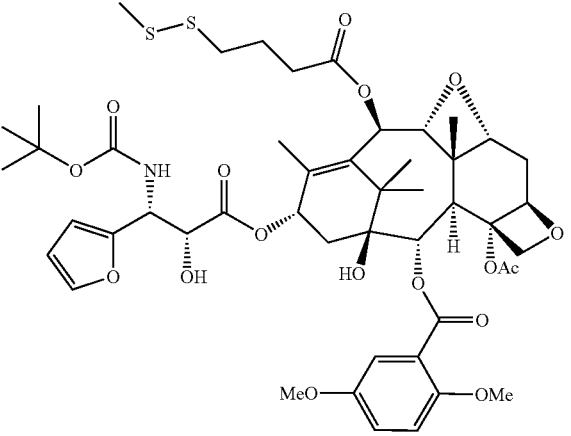 | IGT-18-059 | 0.35 | 0.13 |
| 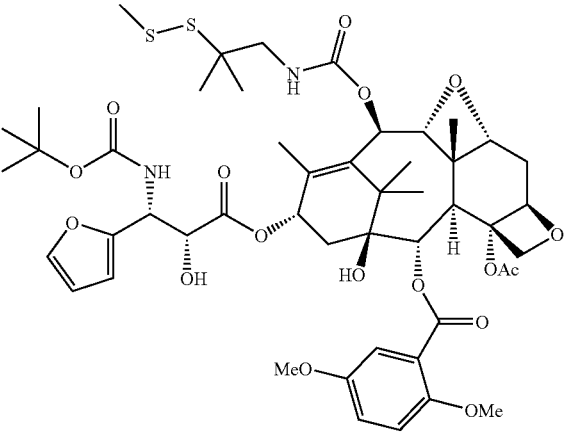 | IGT-15-075 | 0.025 | 0.036 |

Conjugates of the taxanes of the invention and a cell binding agent can be formed using any techniques presently known or later developed. Numerous methods of conjugation are taught in U.S. Pat. No. 5,416,064 and U.S. Pat. No. 5,475,092. The taxane ester can be modified to yield a free amino group and then linked to an antibody or other cell binding agent via an acid labile linker or a photolabile linker. The taxane ester can be condensed with a peptide and subsequently linked to a cell binding agent to produce a peptidase labile linker. The hydroxyl group on the taxane ester can be succinylated and linked to a cell binding agent to produce a conjugate that can be cleaved by intracellular esterases to liberate free drug. Most preferably, the taxane ethers, esters, or carbamates are treated to create a free or protected thiol group, and then the disulfide- or thiol-containing taxanes are linked to the cell binding agent via disulfide bonds.

Representative conjugates of the invention are antibody-taxane, antibody fragment-taxane epidermal growth factor (EGF)-taxane, melanocyte stimulating hormone (MSH)-taxane, thyroid stimulating hormone (TSH)-taxane, estrogen-taxane, estrogen analogue-taxane, androgen-taxane, androgen analogue-taxane, and folate-taxane.

Taxane conjugates of antibodies, antibody fragments, protein or peptide hormones, protein or peptide growth factors and other proteins are made in the same way by known methods. For example, peptides and antibodies can be modified with cross linking reagents such as N-succinimidyl 3-(2-pyridyldithio)propionate, N-succinimidyl 4-(2-pyridyldithio)pentanoate (SPP), 4-succinimidyl-oxycarbonyl-α-methyl-α-(2-pyridyl dithio)-toluene (SMPT), N-succinimidyl-3-(2-pyridyldithio) butyrate (SDPB), N-sulfosuccinimidyl-3-(2-(5-nitro-pyridyldithio) butyrate (SS-NPB), 2-iminothiolane, or S-acetylsuccinic anhydride by known methods. See, Carlsson et al, 173 *Biochem. J.* 723-737 (1978); Blattler et al, 24 *Biochem.* 1517-1524 (1985); Lambert et al, 22 *Biochem.* 3913-3920 (1983); Klotz et al, 96 *Arch. Biochem. Biophys.* 605 (1962); and Liu et al, 18 *Biochem.* 690 (1979), Blakey and Thorpe, 1 *Antibody, Immunoconjugates & Radiopharmaceuticals,* 1-16 (1988), Worrell et al 1 *Anti-Cancer Drug Design* 179-184 (1986). The free or protected thiol-containing cell binding agent thus derived is then reacted with a disulfide- or thiol-containing taxane to produce conjugates. The conjugates can be purified by HPLC or by gel filtration.

Preferably monoclonal antibody- or cell binding agent-taxane conjugates are those that are joined via a disulfide bond, as discussed above, that are capable of delivering taxane molecules. Such cell binding conjugates are prepared by known methods such as by modifying monoclonal antibodies with succinimidyl pyridyldithiopropionate (SPDP) (Carlsson et al, 173 *Biochem. J.* 723-737 (1978)). The resulting thiopyridyl group is then displaced by treatment with thiol-containing taxanes to produce disulfide linked conjugates. Alternatively, in the case of the aryldithio-taxanes, the formation of the cell binding conjugate is effected by direct displacement of the aryl-thiol of the taxane by sulfhydryl groups previously introduced into antibody molecules. Conjugates containing 1 to 10 taxane drugs linked via a disulfide bridge are readily prepared by either method.

More specifically, a solution of the dithio-nitropyridyl modified antibody at a concentration of 2.5 mg/ml in 0.05 M potassium phosphate buffer, at pH 7.5 containing 2 mM EDTA is treated with the thiol-containing taxane (1.3 molar eq./dithiopyridyl group). The release of thio-nitropyridine from the modified antibody is monitored spectrophotometrically at 325 nm and is complete in about 16 hours. The antibody-taxane conjugate is purified and freed of unreacted drug and other low molecular weight material by gel filtration through a column of Sephadex G-25 or Sephacryl S300. The number of taxane moieties bound per antibody molecule can be determined by measuring the ratio of the absorbance at 230 nm and 275 nm. An average of 1-10 taxane molecules/antibody molecule can be linked via disulfide bonds by this method.

The effect of conjugation on binding affinity towards the antiogen-expreesing cells can eb determined using the methods previously described by Liu et al., 93 Proc. Natl. Acad. Sci 8618-8623 (1996). Cytotoxicity of the taxanes and their antibody conjugates to non-adherent cell lines such as Namalwa and HL-60 can be measured by back-extrapolation of cell proliferation curves as. described in Goldmacher et al, 135 *J. Immunol.* 3648-3651 (1985). Cytotoxicity of these compounds to adherent cell lines such as COLO 205 and A-375 can be determined by clonogenic assays as described in Goldmacher et al, 102 *J. Cell Biol.* 1312-1319 (1986).

EXAMPLES

Synthesis of IGT-1 5-075-SH for Conjugation

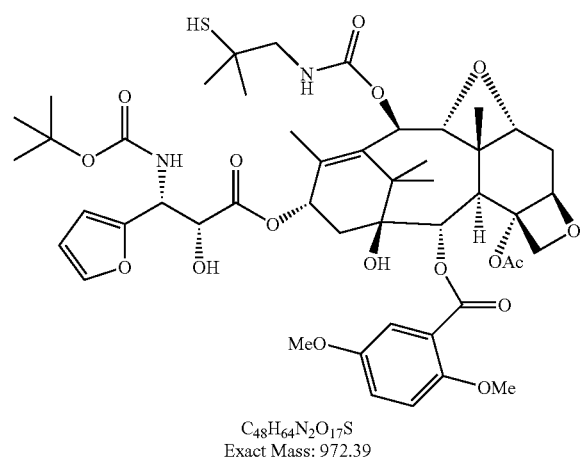

$C_{48}H_{64}N_2O_{17}S$
Exact Mass: 972.39

7α,9α-epoxy-3'-dephenyl-3'-(2-furyl)-2-debenzoyl-2-(2,5-dimethoxybenzoyl)-10-(N-2,2-dimethyl-2-sulfhydryl-ethylcarbamoyl)-docetaxel (IGT-15-075-SH)

In a small vial dissolved 7α,9α-epoxy-3'-dephenyl-3'-(2-furyl)-2-debenzoyl-2-(2,5-dimethoxybenzoyl)-10-(N-2,2-dimethyl-2-methyidithio-ethylcarbamoyl)-docetaxel (36 mg, 0.0353 mmol) in a mixture of methanol (1.0 mL) and ethyl acetate (0.73 mL). In a separate vial dissolved DTT (55 mg, 0.343 mmol) in 50 mM KP buffer pH 7.5 (0.73 mL) which was then added to the taxoid solution. The reaction was monitored by hplc until it was found to be complete (~19 hr). The reaction was quenched with 50 mM KP buffer pH 6.5 (6 mL) and extracted with ethyl acetate (3×20 mL). The combined organic layers were washed with water, dried over anhydrous sodium sulfate, and concentrated. The residue was purified by hplc using a diol column to give the desired product (27 mg, 79%) which was immediately aliquoted and stored for use in conjugation. m/z LC/MS for $C_{48}H_{64}N_2O_{17}SNa^+$: calcd: 995.4. found: 995.5.

Conjugation of taxoids to monoclonal antibodies

HuC242 antibody that binds to the CanAg antigen preferentially expressed on the surface of human colon tumor cells and on other solid tumors was selected for conjugation of taxoids.

In the first step, the antibody was reacted with the modifying agent N-sulfosuccinimidyl 5-nitro-2-pyridyldithiobutanoate (SSNPB) to introduce nitropyridyldithio groups. A solution of huC242 antibody (525 mg, 0.0036 mmol) at a concentration of 8 mg/mL in an aqueous buffer containing 0.05 M potassium phosphate, 0.05 M sodium chloride and 2 mM ethylenediaminetetra-acetic acid (EDTA), pH 6.5 (65.6 mL) was treated with a 8-fold molar excess of a solution of SSNPB (0.0288 mmol, 13.62 mg) in dimethylacetamide (DMA) (3.28 mL). The reaction mixture was stirred at room temperature for 90 min. and then loaded on to a Sephadex G25 gel filtration column (50 mm×35.5 mm, column volume=700 mL) that had been previously equilibrated into an aqueous buffer containing 0.05 M potassium phosphate, 0.05 M sodium chloride and 2 mM EDTA, pH 7.5 (65.6 mL). The modified antibody-containing fractions were collected and pooled to yield 502, 4 mg (95.7%) of product. A small aliquot of the modified antibody was treated with dithiothreitol to cleave the nitro-pyridyl disulfide and the released nitro-pyridine-2-thione was assayed spectrophotometrically ($\epsilon_{325\ nm}$=10,964 $M^{-1}cm^{-1}$ and $\epsilon_{280\ nm}$=3,344 $M^{-1}cm^{-1}$ for nitro-pyridine-2-thione, and $\epsilon_{280\ nm}$=217,560 $M^{-1}cm^{-1}$ for the antibody. An average of 4.53 nitro-pyridyldisulfide molecules were linked per molecule of antibody.

The modified antibody (502.0 mg, 0.0034 mmol) was diluted to 2.5 mg/mL in the above buffer at pH 7.5 and then treated with a solution of the taxoid IGT-15-075 (0.020 mmol, 19.5 mg) in DMA, such that the final concentration of DMA in the buffer was 20%. The conjugation mixture was stirred at room temperature for 16 h. The reaction mixture was purified by passage through a Sephacryl S300 gel filtration column (50 mm×42 cm, column volume=825 mL), that had been previously equilibrated in a phosphate-buffered saline (PBS) buffer at pH 6.5. Fractions containing monomeric antibody-taxoid conjugate were pooled and dialyzed into the PBS buffer. The final conjugate (251 mg) was assayed spectrophotometrically using the following extinction coefficients: ($\epsilon_{323\ nm}$=4,299 $M^{-1}cm^{-1}$, $\epsilon_{280\ nm}$=565 $M^{-1}cm^{-1}$ for the taxoid, and $\epsilon_{280\ nm}$=217,560 $M^{-1}cm^{-1}$ for the antibody. The conjugate contained, on the average, 4.16 taxoid Binding Assay The relative binding affinities of the huC242 antibody and its taxoid conjugate on antigen-expressing HT-29 human colon tumor cells was determined using a fluorescence-based assay. The antibody-taxoid conjugate and naked antibody at starting concentrations of 1 a $10^{-7}$ M were added to 96-well round bottom plates and titrated using 3-fold serial dilutions so that there are duplicates for each concentration. HT-29 cells, were added at 50,000 cells per well to each well containing various concentrations of the antibody or conjugate, as well as to control wells. The plates were incubated on ice for 3 hours. After the incubation period, the cells in the plate were washed, and a fluorescence labeled secondary antibody that binds to a humanized IgG, like huC242, was added, and the plates were incubated for 1 hour on ice. The plates were washed again after the incubation period, and the cells are fixed with 1% formaldehyde/PBS solution. The fluorescence in each well of the plates was read using a Becton Dickinson FACSCalibur fluorescence analyzer. Data are plotted as a percent of the maximum fluorescence obtained at the highest concentration of antibody or conjugate (FIG. 1).

The results demonstrate that conjugation of taxoids to antibodies does not alter the binding affinity to target cells.

In vitro potency and specificity of huC242-Taxoid conjugate

Samples of free taxoid or huC242-Taxoid conjugate were added to a 96-well flat bottomed tissue culture plate and titrated using serial dilutions ranging from $1 \times 10^{-12}$ M to $3 \times 10^{-7}$ M. Human colon tumor cells, COLO 205, or human melanoma cells, A-375, were added to the wells in such a way that there were triplicate samples for each drug concentration for each cell line. The plates were incubated at 37° C. in an atmosphere of 5% $CO_2$ for 4 days.

At the end of the incubation period, 20 μl of the tetrazolium reagent WST-8 (2-(2-methoxy-nitrophenyl)-3-(4-nitrophenyl)-5-(2,4-disulfophenyl)-2-tetrazolium, monosodium salt]) was added to each well, and the plates were returned to the incubator for 2 hours. The absorbance in each well of the plates was then measured using the Molecular Devices plate reader at 450 nm. Surviving fraction of cells at each concentration of taxoid or conjugate are plotted in FIGS. 2a, b.

The results demonstrate that conjugation to antibodies renders high targets specificity to the taxoid. Thus huC242-taxoid is very potent in killing target human colon cancer COLO 205 cells with an IC50 value of $8 \times 10^{-11}$ M. In contrast, antigen negative cells are about 150-fold less sensitive, with an $IC_{50}$ value of $1.2 \times 10^{-8}$ M, demonstrating the antigen specificity of the cytotoxic effect (FIG. 2x). The free taxoid, on the other hand, is equally potent towards both cell lines ($IC_{50} \sim 1 \times 10^{-10}$ M (FIG. 2b).

What is claimed is:

1. A taxane compound having the following formula (I):

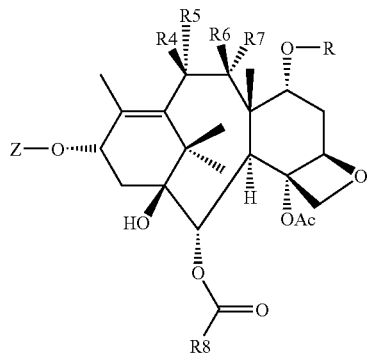

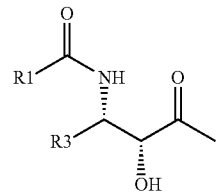

wherein Z=H or a radical of formula II;

$R_1$ is a linker;

$R_3$ is a linker or an optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms;

$R_4$ is a linker, H, a hydroxy radical, an alkoxy, an alkenyloxy, an optionally substituted alkanoyloxy, aroyloxy, alkenoyloxy, alkynoyloxy, cycloalkanoyloxy, alkoxyacetyl, alkylthioacetyl, alkyloxycarbonyloxy, cycloalkyloxy, cycloalkenyloxy, carbamoyloxy, alkylcarbamoyloxy, or dialkylcarbamoyloxy, a heterocyclic or aryl ether, ester or carbamate, or, a linear, branched, or cyclic alkyl or alkenyl ester or ether having from 1 to 10 carbon atoms or a carbamate of the formula —OCOX, wherein X is a nitrogen-containing heterocycle, or a carbamate of the formula —OCONR$_9$R$_{10}$, wherein $R_9$ and $R_{10}$ are the same or different and are H, linear, branched, or cyclic alkyl having from 1 to 10 atoms or simple or substituted aryl having from 1 to 10 carbon atoms;

$R_5$ and R together form a bond to form a cyclic ether, or $R_7$ and R together form a bond to form a cyclic ether; provided that when $R_5$ and R form a bond, then $R_7$ is H, and provided that when $R_7$ and R form a bond then $R_5$ is H;

$R_6$ is H; and $R_8$ is optionally substituted aryl or a heterocyclic radical.

2. A taxane compound having the following formula (I):

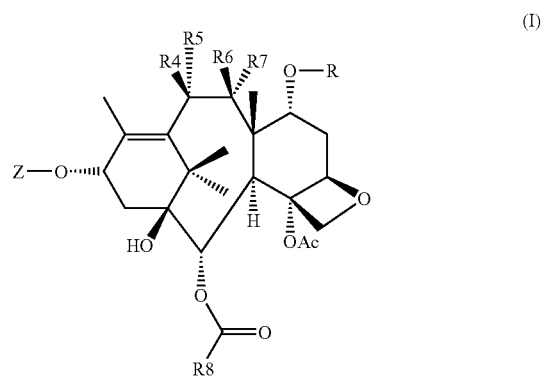

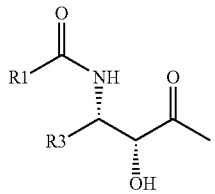

(II)

wherein Z=H or a radical of formula II;

R₁ is a linker;

R₂ is an alkyl radical having from 1 to 10 carbon atoms, alkenyl or alkynyl having from 2 to 10 carbon atoms, cycloalkyl or cycloalkenyl having from 3 to 10 carbon atoms, optionally substituted aryl or heterocyclic radical;

R₃ is a linker or an optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms;

R₄ is a linker, H, a hydroxy radical, an alkoxy, an alkenyloxy, an optionally substituted alkanoyloxy, aroyloxy, alkenoyloxy, alkynoyloxy, cycloalkanoyloxy, alkoxyacetyl, alkylthioacetyl, alkyloxycarbonyloxy, cycloalkyloxy, cycloalkenyloxy, carbamoyloxy, alkylcarbamoyloxy, or dialkylcarbamoyloxy, a heterocyclic or aryl ether, ester or carbamate, or, a linear, branched, or cyclic alkyl or alkenyl ester or ether having from 1 to 10 carbon atoms or a carbamate of the formula —OCOX, wherein X is unsubstituted or substituted piperidino, morpholino, piperazino, N-methylpiperazino, or a carbamate of the formula —OCONR₉R₁₀, wherein R₉ and R₁₀ are the same or different and are H, linear, branched, or cyclic alkyl having from 1 to 10 atoms or simple or substituted aryl having from 1 to 10 carbon atoms;

R₅ and R together form a bond to form a cyclic ether, or R₇ and R together form a bond to form a cyclic ether; provided that when R₅ and R form a bond, then R₇ is H, and provided that when R₇ and R form a bond then R₅ is H;

R₆ is H; and

R₈ is optionally substituted aryl or a heterocyclic radical.

3. A taxane compound having the following formula (I):

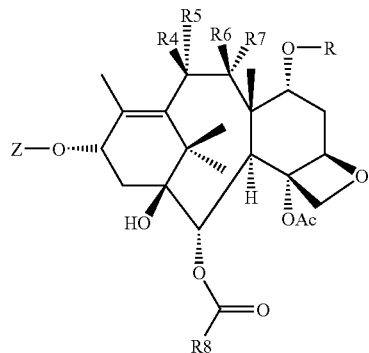

(I)

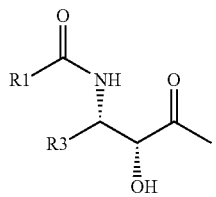

(II)

wherein Z=H or a radical of formula II;

R₁ is a linker or an optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms, —OR₂ or a carbamate formed from any of said alkyl having from 1 to 10 carbon atoms, alkenyl or alkynyl having from 2 to 10 carbon atoms, cycloalkyl or cycloalkenyl having from 3 to 10 carbon atoms, or optionally substituted aryl or heterocyclyl radical;

R₂ is an alkyl radical having from 1 to 10 carbon atoms, alkenyl or alkynyl having from 2 to 10 carbon atoms, cycloalkyl or cycloalkenyl having from 3 to 10 carbon atoms, optionally substituted aryl or heterocyclic radical;

R₃ is a linker;

R₄ is a linker, H, a hydroxy radical, an alkoxy, an alkenyloxy, an optionally substituted alkanoyloxy, aroyloxy, alkenoyloxy, alkynoyloxy, cycloalkanoyloxy, alkoxyacetyl, alkylthioacetyl, alkyloxycarbonyloxy, cycloalkyloxy, cycloalkenyloxy, carbamoyloxy, alkylcarbamoyloxy, or dialkylcarbamoyloxy, a heterocyclic or aryl ether, ester or carbamate, or, a linear, branched, or cyclic alkyl or alkenyl ester or ether having from 1 to 10 carbon atoms or a carbamate of the formula —OCOX, wherein X is a nitrogen-containing heterocycle, or a carbamate of the formula —OCONR₉R₁₀, wherein R₉ and R₁₀ are the same or different and are H, linear, branched, or cyclic alkyl having from 1 to 10 atoms or simple or substituted aryl having from 1 to 10 carbon atoms;

R₅ and R together form a bond to form a cyclic ether, or R₇ and R together form a bond to form a cyclic ether; provided that when R₅ and R form a bond, then R₇ is H, and provided that when R₇ and R form a bond then R₅ is H;

R₆ is H; and

R₈ is optionally substituted aryl or a heterocyclic radical.

4. A taxane compound having the following formula (I):

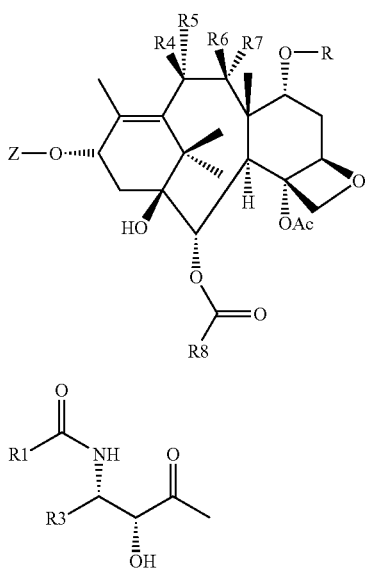

wherein Z=H or a radical of formula II;

$R_1$ is a linker or an optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms, —$OR_2$ or a carbamate formed from any of said alkyl having from 1 to 10 carbon atoms, alkenyl or alkynyl having from 2 to 10 carbon atoms, cycloalkyl or cycloalkenyl having from 3 to 10 carbon atoms, or optionally substituted aryl or heterocyclyl radical;

$R_2$ is an alkyl radical having from 1 to 10 carbon atoms, alkenyl or alkynyl having from 2 to 10 carbon atoms, cycloalkyl or cycloalkenyl having from 3 to 10 carbon atoms, optionally substituted aryl or heterocyclic radical;

$R_3$ is a linker or an optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms;

$R_4$ is a linker;

$R_5$ and R together form a bond to form a cyclic ether, or $R_7$ and R together form a bond to form a cyclic ether; provided that when $R_5$ and R form a bond, then $R_7$ is H, and provided that when $R_7$ and R form a bond then $R_5$ is H;

$R_6$ is H; and $R_8$ is optionally substituted aryl or a heterocyclic radical.

5. A compound according to claim 3 or claim 4 wherein $R_2$ is an alkyl group.

6. A compound according to claim 3 or claim 4 wherein $R_2$ is a tert-butyl group.

7. A compound according to claim 1 wherein the linkers contain one or more groups selected from the list consisting of disulfide groups, thioether groups, acid labile groups, photolabile groups, peptidase labile groups and esterase labile groups.

8. A compound according to claim 7 wherein the linkers contain one or more groups selected form the list consisting of disulfide groups and thioether groups.

9. A compound according to claim 7 wherein the linkers are thiol- or disulfide-containing, and wherein the side chain carrying the thiol or disulfide group can be linear or branched, aromatic or heterocyclic.

10. A compound according to claim 1 wherein the linker at $R_1$ is selected form the group consisting of —$(CR_{13}R_{14})_m(CR_{15}R_{16})_n(OCH_2CH_2)_ySZ'$, —$O(CR_{13}R_{14})_m(CR_{15}R_{16})_n(OCH_2CH_2)_ySZ'$, —$(CR_{13}R_{14})_m(CR_{17}=CR_{18})(CR_{15}R_{16})_m(OCH_2CH_2)_ySZ'$, —O—$(CR_{13}R_{14})_m$ $(CR_{17}=CR_{18})(CR_{15}R_{16})_m$ $(OCH_2CH_2)_ySZ'$, —$NR_{12}(CR_{13}R_{14})_m(CR_{15}R_{16})_n(OCH_2CH_2)_ySZ'$, phenyl-X'SZ', furyl-X'SZ', oxazolyl-X'SZ', thiazolyl-X'SZ', thienyl-X'SZ', imidazolyl-X'SZ', morpholino-X'SZ', -piperazino-X'SZ', piperidino-X'SZ', -furyl-X'SZ', -thienyl-X'SZ', -thiazolyl-X'SZ', —N-methylpiperazino-X'SZ', -morpholino-X'SZ', -piperazino-X'SZ', -piperidino-X'SZ', and —N-methylpiperazino-X'SZ', wherein:

Z' is H, a thiol protective group or SR';

and wherein —X' is a direct link or a linear alkyl or branched alkyl having from 1-10 carbon atoms or a polyethylene glycol spacer with 2 to 20 repeating ethylene oxy units;

R' and $R_{12}$ are the same or different and are linear alkyl, branched alkyl or cyclic alkyl having from 1 to 10 carbon atoms, or unsubstituted or substituted aryl or heterocyclic, and $R_{12}$ can in addition be H;

$R_{13}$, $R_{14}$, $R_{15}$ and $R_{16}$ are the same or different and are H or a linear or branched alkyl having from 1 to 4 carbon atoms;

$R_{17}$ and $R_{18}$ are H or alkyl;

n is an integer of 1 to 10;

m is an integer from 1 to 10 and can also be 0; and y is an integer from 1 to 20 and can also be 0.

11. A compound according to claim 1 wherein the linker at $R_4$ is selected from the group consisting of —$O(CR_{13}R_{14})_m(CR_{15}R_{16})_n(OCH_2CH_2)_ySZ'$, —$OCO(CR_{13}R_{14})_m(CR_{15}R_{16})_n$ $(OCH_2CH_2)_ySZ'$, —$O(CR_{13}R_{14})_m(CR_{17}=CR_{18})(CR_{15}R_{16})_m(OCH_2CH_2)_ySZ'$, —OCO—$(CR_{13}R_{14})_m(CR_{17}=CR_{18})(CR_{15}R_{16})_m(OCH_2CH_2)_ySZ'$, —$OCONR_{12}(CR_{13}R_{14})_m(CR_{15}R_{16})_n(OCH_2CH_2)_ySZ'$, —OCO-phenyl-X'SZ', —OCO-furyl-X'SZ', —OCO-oxazolyl-X'SZ', —OCO-thiazolyl-X'SZ', —OCO-thienyl-X'SZ', —OCO-imidazolyl-X'SZ', —OCO-morpholino-X'SZ', —OCO-piperazino-X'SZ', —OCO-piperidino-X'SZ', -OCO-N-methylpiperazino-X'SZ', and —OCO—N-methylpiperazino-X'SZ', wherein:

Z' is H, a thiol protective group or SR';

wherein X' is a direct link or a linear alkyl or branched alkyl having from 1-10 carbon atoms or a polyethylene glycol spacer with 2 to 20 repeating ethylene oxy units;

R' and $R_{12}$ are the same or different and are linear alkyl, branched alkyl or cyclic alkyl having from 1 to 10 carbon atoms, or simple or substituted aryl or heterocyclic, and $R_{12}$ can in addition be H;

$R_{13}$, $R_{14}$, $R_{15}$ and $R_{16}$ are the same or different and are H or a linear or branched alkyl having from 1 to 4 carbon atoms;

$R_{17}$ and $R_{18}$ are H or alkyl;

n is an integer of 1 to 10;

m is an integer from 1 to 10 and can also be 0; and y is an integer from 1 to 20 and can also be 0.

12. A compound according to claim 1 wherein the linker at $R_3$ is selected from the group consisting of —$(CR_{13}R_{14})_m(CR_{15}R_{16})_n(OCH_2CH_2)_ySZ'$, —$(CR_{13}R_{14})_m(CR_{17}=CR_{18})(CR_{15}R_{16})_m(OCH_2CH_2)_ySZ'$, phenyl-X'SZ', furyl-X'SZ', oxazolyl-X'SZ', thiazolyl-X'SZ', thienyl-X'SZ', and imidazolyl-X'SZ', wherein:

Z' is H, a thiol protective group or SR';

wherein X' is a direct link or a linear alkyl or branched alkyl having from 1-10 carbon atoms or a polyethylene glycol spacer with 2 to 20 repeating ethylene oxy units;

R' is linear alkyl, branched alkyl or cyclic alkyl having from 1 to 10 carbon atoms, or simple or substituted aryl or heterocyclic;

$R_{13}$, $R_{14}$, $R_{15}$ and $R_{16}$ are the same or different and are H or a linear or branched alkyl having from 1 to 4 carbon atoms;

$R_{17}$ and $R_{18}$ are H or alkyl;

n is an integer of 1 to 10;

m is an integer from 1 to 10 and can also be 0; and y is an integer from 1 to 20 and can also be 0.

13. A compound according to claim 1 wherein $R_8$ is 3-methoxyphenyl, 3-chlorophenyl, 2,5-dimethoxyphenyl, furyl, pyrollyl, thienyl, thiazolyl, imidazolyl, pyridyl, oxazolyl, indolyl, benzofuranyl or benzothienyl.

14. A compound according to claim 1 wherein $R_5$ is H and R and $R_7$ together form a bond.

15. A compound according to claim 4 wherein in the compound of formula (I)

Z is H or a radical of formula II;

$R_1$ is an optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms, —$OR_2$ or a carbamate formed from any of said alkyl having from 1 to 10 carbon atoms, alkenyl or alkynyl having from 2 to 10 carbon atoms, cycloalkyl or cycloalkenyl having from 3 to 10 carbon atoms, or optionally substituted aryl or heterocyclyl radical;

$R_2$ is an alkyl radical having from 1 to 10 carbon atoms, alkenyl or alkynyl having from 2 to 10 carbon atoms, cycloalkyl or cycloalkenyl having from 3 to 10 carbon atoms, optionally substituted aryl or heterocyclic radical;

$R_3$ is optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms;

$R_5$ and R together form a bond to form a cyclic ether, or $R_7$ and R together form a bond to form a cyclic ether; provided that when $R_5$ and R form a bond, then $R_7$ is H, and provided that when $R_7$ and R form a bond then $R_5$ is H;

$R_6$ is H; and $R_8$ is an optionally substituted aryl or heterocyclic radical.

16. A compound according to claim 1 wherein:

Z is a radical of formula II;

$R_3$ is optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms;

$R_4$ is H, a hydroxy radical, an alkoxy, an alkenyloxy, an optionally substituted alkanoyloxy, aroyloxy, alkenoyloxy, alkynoyloxy, cycloalkanoyloxy, alkoxyacetyl, alkylthioacetyl, alkyloxycarbonyloxy, cycloalkyloxy, cycloalkenyloxy, carbamoyloxy, alkylcarbamoyloxy, or dialkylcarbamoyloxy, a heterocyclic or aryl ether, ester or carbamate, or, a linear, branched, or cyclic alkyl or alkenyl ester or ether having from 1 to 10 carbon atoms or a carbamate of the formula —OCOX, wherein X is a nitrogen-containing heterocycle, or a carbamate of the formula —OCONR$_9$R$_{10}$, wherein $R_9$ and $R_{10}$ are the same or different and are H, linear, branched, or cyclic alkyl having from 1 to 10 atoms or unsubstituted or substituted aryl having from 5 to 10 carbon atoms;

$R_5$ and R together form a bond to form a cyclic ether, or $R_7$ and R together form a bond to form a cyclic ether; provided that when $R_5$ and R form a bond, then $R_7$ is H, and provided that when $R_7$ and R form a bond then $R_5$ is H;

$R_6$ is H; and $R_8$ is an optionally substituted aryl or heterocyclic radical.

17. A compound according to claim 1 wherein:

Z is a radical of formula II;

$R_3$ is optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms;

$R_4$ is H, a hydroxy radical, an alkoxy, an alkenyloxy, an optionally substituted alkanoyloxy, aroyloxy, alkenoyloxy, alkynoyloxy, cycloalkanoyloxy, alkoxyacetyl, alkylthioacetyl, alkyloxycarbonyloxy, cycloalkyloxy, cycloalkenyloxy, carbamoyloxy, alkylcarbamoyloxy, or dialkylcarbamoyloxy, a heterocyclic or aryl ether, ester or carbamate, or, a linear, branched, or cyclic alkyl or alkenyl ester or ether having from 1 to 10 carbon atoms or a carbamate of the formula —OCOX, wherein X is unsubstituted or substituted piperidino, morpholino, piperazino, N-methylpiperazino, or a carbamate of the formula —OCONR$_9$R$_{10}$, wherein $R_9$ and $R_{10}$ are the same or different and are H, linear, branched, or cyclic alkyl having from 1 to 10 atoms or unsubstituted or substituted aryl having from 5 to 10 carbon atoms;

$R_5$ and R together form a bond to form a cyclic ether, or $R_7$ and R together form a bond to form a cyclic ether; provided that when $R_5$ and R form a bond, then $R_7$ is H, and provided that when $R_7$ and R form a bond then $R_5$ is H;

$R_6$ is H; and $R_8$ is an optionally substituted aryl or heterocyclic radical.

18. A compound according to claim 3 wherein:

Z is a radical of formula II;

$R_1$ is an optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms, —$OR_2$ or a carbamate formed from any of said alkyl having from 1 to 10 carbon atoms, alkenyl or alkynyl having from 2 to 10 carbon atoms, cycloalkyl or cycloalkenyl having from 3 to 10 carbon atoms, or optionally substituted aryl or heterocyclyl radical;

$R_2$ is alkyl radical having from 1 to 10 carbon atoms, alkenyl or alkynyl having from 2 to 10 carbon atoms, cycloalkyl or cycloalkenyl having from 3 to 10 carbon atoms, optionally substituted aryl or heterocyclic radical;

$R_4$ is H, a hydroxy radical, an alkoxy, an alkenyloxy, an optionally substituted alkanoyloxy, aroyloxy, alkenoyloxy, alkynoyloxy, cycloalkanoyloxy, alkoxyacetyl, alkylthioacetyl, alkyloxycarbonyloxy, cycloalkyloxy, cycloalkenyloxy, carbamoyloxy, alkylcarbamoyloxy, or dialkylcarbamoyloxy, a heterocyclic or aryl ether, ester or carbamate, or, a linear, branched, or cyclic alkyl or alkenyl ester or ether having from 1 to 10 carbon atoms or a carbamate of the formula —OCOX, wherein X is a nitrogen-containing heterocycle, or a carbamate of the formula —OCONR$_9$R$_{10}$, wherein $R_9$ and $R_{10}$ are the same or different and are H, linear, branched, or cyclic alkyl having from 1 to 10 atoms or unsubstituted or substituted aryl having from 5 to 10 carbon atoms;

R$_5$ and R together form a bond to form a cyclic ether, or R$_7$ and R together form a bond to form a cyclic ether; provided that when R$_5$ and R form a bond, then R$_7$ is H, and provided that when R$_7$ and R form a bond then R$_5$ is H;

R$_6$ is H; and

R$_8$ is an optionally substituted aryl or heterocyclic radical.

19. A compound according to claim 3 wherein:

Z is a radical of formula II;

R$_1$ is an optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms, —OR$_2$ or a carbamate formed from any of said alkyl having from 1 to 10 carbon atoms, alkenyl or alkynyl having from 2 to 10 carbon atoms, cycloalkyl or cycloalkenyl having from 3 to 10 carbon atoms, or optionally substituted aryl or heterocyclyl radical;

R$_2$ is alkyl radical having from 1 to 10 carbon atoms, alkenyl or alkynyl having from 2 to 10 carbon atoms, cycloalkyl or cycloalkenyl having from 3 to 10 carbon atoms, optionally substituted aryl or heterocyclic radical;

R$_4$ is H, a hydroxy radical, an alkoxy, an alkenyloxy, an optionally substituted alkanoyloxy, aroyloxy, alkenoyloxy, alkynoyloxy, cycloalkanoyloxy, alkoxyacetyl, alkylthioacetyl, alkyloxycarbonyloxy, cycloalkyloxy, cycloalkenyloxy, carbamoyloxy, alkylcarbamoyloxy, or dialkylcarbamoyloxy, a heterocyclic or aryl ether, ester or carbamate, or, a linear, branched, or cyclic alkyl or alkenyl ester or ether having from 1 to 10 carbon atoms or a carbamate of the formula —OCOX, wherein X is unsubstituted or substituted piperidino, morpholino, piperazino, N-methylpiperazino, or a carbamate of the formula —OCONR$_9$R$_{10}$, wherein R$_9$ and R$_{10}$ are the same or different and are H, linear, branched, or cyclic alkyl having from 1 to 10 atoms or unsubstituted or substituted aryl having from 5 to 10 carbon atoms;

R$_5$ and R together form a bond to form a cyclic ether, or R$_7$ and R together form a bond to form a cyclic ether; provided that when R$_5$ and R form a bond, then R$_7$ is H, and provided that when R$_7$ and R form a bond then R$_5$ is H;

R$_6$ is H; and

R$_8$ is an optionally substituted aryl or heterocyclic radical.

20. A cytotoxic agent comprising one or more taxanes covalently bonded to a cell binding agent through a linking group, wherein at least one of said taxanes is a compound represented by formula (III):

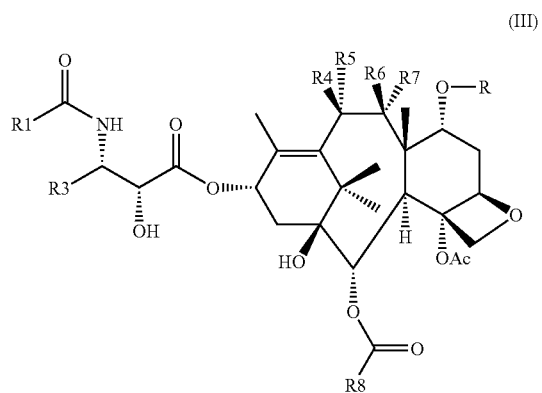

(III)

wherein:

R$_1$ is a linker;

R$_3$ is an optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms;

R$_4$ is H, a hydroxy radical, an alkoxy, an alkenyloxy, an optionally substituted alkanoyloxy, aroyloxy, alkenoyloxy, alkynoyloxy, cycloalkanoyloxy, alkoxyacetyl, alkylthioacetyl, alkyloxycarbonyloxy, cycloalkyloxy, cycloalkenyloxy, carbamoyloxy, alkylcarbamoyloxy, or dialkylcarbamoyloxy, a heterocyclic or aryl ether, ester or carbamate, or, a linear, branched, or cyclic alkyl or alkenyl ester or ether having from 1 to 10 carbon atoms or a carbamate of the formula —OCOX, wherein X is a nitrogen-containing heterocycle, or a carbamate of the formula —OCONR$_9$R$_{10}$, wherein R$_9$ and R$_{10}$ are the same or different and are H, linear, branched, or cyclic alkyl having from 1 to 10 atoms or unsubstituted or substituted aryl having from 1 to 10 carbon atoms;

R$_5$ and R together form a bond to form a cyclic ether, or R$_7$ and R together form a bond to form a cyclic ether; provided that when R$_5$ and R form a bond, then R$_7$ is H, and provided that when R$_7$ and R form a bond then R$_5$ is H;

R$_6$ is H; and

R$_8$=optionally substituted aryl or heterocyclic radical.

21. A cytotoxic agent according to claim 20 comprising one or more taxanes covalently bonded to a cell binding agent through a linking group, wherein at least one of said taxanes is a compound represented by formula (III):

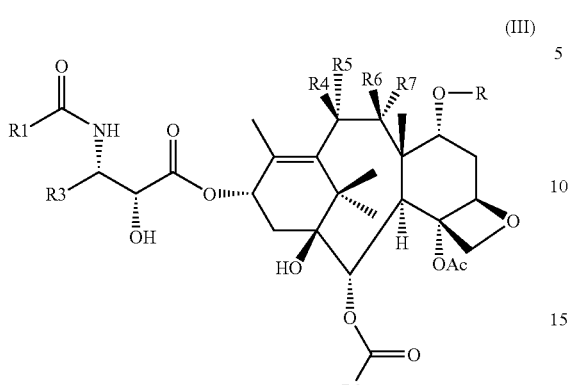

(III)

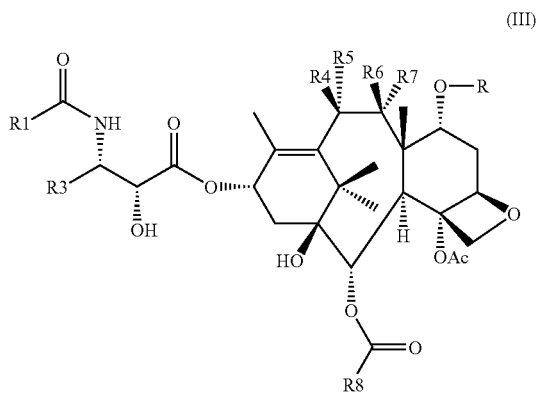

(III)

wherein:

R$_1$ is a linker;

R$_3$ is an optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms;

R$_4$ is H, a hydroxy radical, an alkoxy, an alkenyloxy, an optionally substituted alkanoyloxy, aroyloxy, alkenoyloxy, alkynoyloxy, cycloalkanoyloxy, alkoxyacetyl, alkylthioacetyl, alkyloxycarbonyloxy, cycloalkyloxy, cycloalkenyloxy, carbamoyloxy, alkylcarbamoyloxy, or dialkylcarbamoyloxy, a heterocyclic or aryl ether, ester or carbamate, or, a linear, branched, or cyclic alkyl or alkenyl ester or ether having from 1 to 10 carbon atoms or a carbamate of the formula —OCOX, wherein X is unsubstituted or substituted piperidino, morpholino, piperazino, N-methylpiperazino, or a carbamate of the formula —OCONR$_9$R$_{10}$, wherein R$_9$ and R$_{10}$ are the same or different and are H, linear, branched, or cyclic alkyl having from 1 to 10 atoms or unsubstituted or substituted aryl having from 1 to 10 carbon atoms;

R$_5$ and R together form a bond to form a cyclic ether, or R$_7$ and R together form a bond to form a cyclic ether; provided that when R$_5$ and R form a bond, then R$_7$ is H, and provided that when R$_7$ and R form a bond then R$_5$ is H;

R$_6$ is H; and

R$_8$=optionally substituted aryl or heterocyclic radical.

22. A cytotoxic agent comprising one or more taxanes covalently bonded to a cell binding agent through a linking group, wherein at least one of said taxanes is a compound represented by formula (III):

wherein:

R$_1$ is an optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms, —OR$_2$ or a carbamate formed from any of said alkyl having from 1 to 10 carbon atoms, alkenyl or alkynyl having from 2 to 10 carbon atoms, cycloalkyl or cycloalkenyl having from 3 to 10 carbon atoms, or optionally substituted aryl or heterocyclyl radical;

R$_2$ is an alkyl radical having from 1 to 10 carbon atoms, alkenyl or alkynyl having from 2 to 10 carbon atoms, cycloalkyl or cycloalkenyl having from 3 to 10 carbon atoms, optionally substituted aryl or heterocyclic radical;

R$_3$ is a linker;

R$_4$ is H, a hydroxy radical, an alkoxy, an alkenyloxy, an optionally substituted alkanoyloxy, aroyloxy, alkenoyloxy, alkynoyloxy, cycloalkanoyloxy, alkoxyacetyl, alkylthioacetyl, alkyloxycarbonyloxy, cycloalkyloxy, cycloalkenyloxy, carbamoyloxy, alkylcarbamoyloxy, or dialkylcarbamoyloxy, a heterocyclic or aryl ether, ester or carbamate, or, a linear, branched, or cyclic alkyl or alkenyl ester or ether having from 1 to 10 carbon atoms or a carbamate of the formula —OCOX, wherein X is a nitrogen-containing heterocycle, or a carbamate of the formula —OCONR$_9$R$_{10}$, wherein R$_9$ and R$_{10}$ are the same or different and are H, linear, branched, or cyclic alkyl having from 1 to 10 atoms or unsubstituted or substituted aryl having from 1 to 10 carbon atoms;

R$_5$ and R together form a bond to form a cyclic ether, or R$_7$ and R together form a bond to form a cyclic ether; provided that when R$_5$ and R form a bond, then R$_7$ is H, and provided that when R$_7$ and R form a bond then R$_5$ is H;

R$_6$ is H; and

R$_8$ is optionally substituted aryl or heterocyclic radical.

23. A cytotoxic agent according to claim 22 comprising one or more taxanes covalently bonded to a cell binding agent through a linking group, wherein at least one of said taxanes is a compound represented by formula (III):

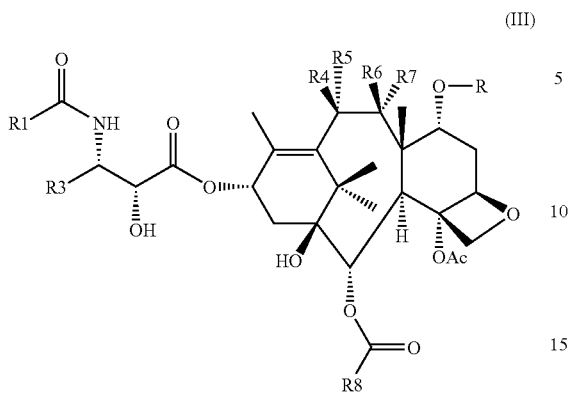 (III)

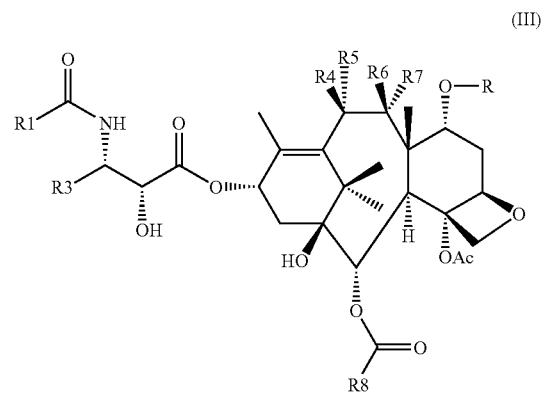 (III)

wherein:

$R_1$ is an optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms, —$OR_2$ or a carbamate formed from any of said alkyl having from 1 to 10 carbon atoms, alkenyl or alkynyl having from 2 to 10 carbon atoms, cycloalkyl or cycloalkenyl having from 3 to 10 carbon atoms, or optionally substituted aryl or heterocyclyl radical;

$R_2$ is an alkyl radical having from 1 to 10 carbon atoms, alkenyl or alkynyl having from 2 to 10 carbon atoms, cycloalkyl or cycloalkenyl having from 3 to 10 carbon atoms, optionally substituted aryl or heterocyclic radical;

$R_3$ is a linker;

$R_4$ is H, a hydroxy radical, an alkoxy, an alkenyloxy, an optionally substituted alkanoyloxy, aroyloxy, alkenoyloxy, alkynoyloxy, cycloalkanoyloxy, alkoxyacetyl, alkylthioacetyl, alkyloxycarbonyloxy, cycloalkyloxy, cycloalkenyloxy, carbamoyloxy, alkylcarbamoyloxy, or dialkylcarbamoyloxy, a heterocyclic or aryl ether, ester or carbamate, or, a linear, branched, or cyclic alkyl or alkenyl ester or ether having from 1 to 10 carbon atoms or a carbamate of the formula —OCOX, wherein X is unsubstituted or substituted piperidino, morpholino, piperazino, N-methylpiperazino, or a carbamate of the formula —OCON$R_9R_{10}$, wherein $R_9$ and $R_{10}$ are the same or different and are H, linear, branched, or cyclic alkyl having from 1 to 10 atoms or unsubstituted or substituted aryl having from 1 to 10 carbon atoms;

$R_5$ and R together form a bond to form a cyclic ether, or $R_7$ and R together form a bond to form a cyclic ether; provided that when $R_5$ and R form a bond, then $R_7$ is H, and provided that when $R_7$ and R form a bond then $R_5$ is H;

$R_6$ is H; and $R_8$ is optionally substituted aryl or heterocyclic radical.

24. A cytotoxic agent comprising one or more taxanes covalently bonded to a cell binding agent through a linking group, wherein at least one of said taxanes is a compound represented by formula (III):

wherein:

$R_1$ is an optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms, —$OR_2$ or a carbamate formed from any of said alkyl having from 1 to 10 carbon atoms, alkenyl or alkynyl having from 2 to 10 carbon atoms, cycloalkyl or cycloalkenyl having from 3 to 10 carbon atoms, or optionally substituted aryl or heterocyclyl radical;

$R_2$ is an alkyl radical having from 1 to 10 carbon atoms, alkenyl or alkynyl having from 2 to 10 carbon atoms, cycloalkyl or cycloalkenyl having from 3 to 10 carbon atoms, optionally substituted aryl or heterocyclic radical;

$R_3$ is an optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms;

$R_4$ is a linker;

$R_5$ and R together form a bond to form a cyclic ether, or $R_7$ and R together form a bond to form a cyclic ether; provided that when $R_5$ and R form a bond, then $R_7$ is H, and provided that when $R_7$ and R form a bond then $R_5$ is H;

$R_6$ is H; and $R_8$ is optionally substituted aryl or heterocyclic radical.

25. A therapeutic composition comprising:
a therapeutically effective amount of the cytotoxic agent of any one of claims 20, 22, or 24; and
a pharmaceutically acceptable carrier.

26. The cytotoxic agent of any one of claims 20, 22, or 24 wherein the cell binding agent is selected from the group consisting of antibodies, an antibody fragment, interferons, lymphokines, hormones, vitamins, growth factors, colony stimulating factors, and transferrin.

27. The cytotoxic agent of any one of claims 20, 22, or 24 wherein the cell binding agent is an antibody.

28. The cytotoxic agent of any one of claims 20, 22, or 24 wherein the cell binding agent is a monoclonal antibody.

29. The cytotoxic agent of any one of claims 20, 22, or 24 wherein the cell binding agent is an antigen specific antibody fragment.

30. The cytotoxic agent of any one of claims 20, 22, or 24 wherein the antibody fragment is sFV, Fab, Fab', or F(ab')$_2$.

31. The cytotoxic agent of any one of claims 20, 22, or 24 wherein the cell binding agent is a growth factor or colony stimulating factor.

32. A method of killing selected cell populations comprising contacting target cells or tissue containing target cells with an effective amount of the cytotoxic agent of any one of claims 20, 22, or 24.

33. A taxane compound having the following formula (I):

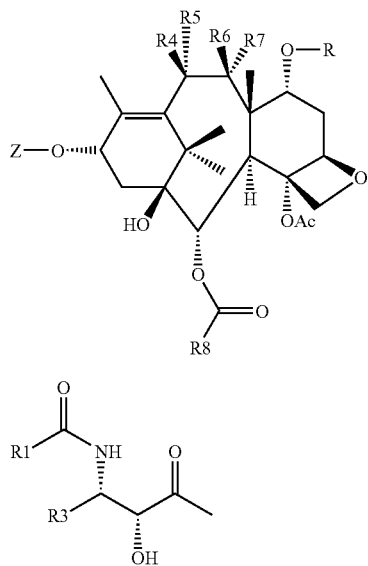

wherein Z=H or a radical of formula II;
$R_1$ is a linker or an optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms, —$OR_2$ or a carbamate formed from any of said alkyl having from 1 to 10 carbon atoms, alkenyl or alkynyl having from 2 to 10 carbon atoms, cycloalkyl or cycloalkenyl having from 3 to 10 carbon atoms, or optionally substituted aryl or heterocyclyl radical;
$R_2$ is an alkyl radical having from 1 to 10 carbon atoms, alkenyl or alkynyl having from 2 to 10 carbon atoms, cycloalkyl or cycloalkenyl having from 3 to 10 carbon atoms, optionally substituted aryl or heterocyclic radical;
$R_3$ is a linker;
$R_4$ is a linker, H, a hydroxy radical, an alkoxy, an alkenyloxy, an optionally substituted alkanoyloxy, aroyloxy, alkenoyloxy, alkynoyloxy, cycloalkanoyloxy, alkoxyacetyl, alkylthioacetyl, alkyloxycarbonyloxy, cycloalkyloxy, cycloalkenyloxy, carbamoyloxy, alkylcarbamoyloxy, or dialkylcarbamoyloxy, a heterocyclic or aryl ether, ester or carbamate, or, a linear, branched, or cyclic alkyl or alkenyl ester or ether having from 1 to 10 carbon atoms or a carbamate of the formula —OCOX, wherein X is unsubstituted or substituted piperidino, morpholino, piperazino, N-methylpiperazino, or a carbamate of the formula —$OCONR_9R_{10}$, wherein $R_9$ and $R_{10}$ are the same or different and are H, linear, branched, or cyclic alkyl having from 1 to 10 atoms or simple or substituted aryl having from 1 to 10 carbon atoms;
$R_5$ and R together form a bond to form a cyclic ether, or $R_7$ and R together form a bond to form a cyclic ether; provided that when $R_5$ and R form a bond, then $R_7$ is H, and provided that when $R_7$ and R form a bond then $R_5$ is H;
$R_6$ is H; and
$R_8$ is optionally substituted aryl or a heterocyclic radical.

34. A taxane compound having the following formula (I):

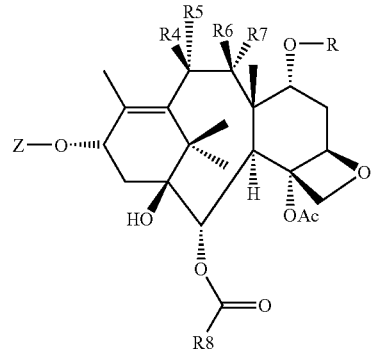

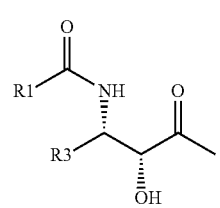

wherein Z=H or a radical of formula II;
$R_1$ is a linker or an optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms, —$OR_2$ or a carbamate formed from any of said alkyl having from 1 to 10 carbon atoms, alkenyl or alkynyl having from 2 to 10 carbon atoms, cycloalkyl or cycloalkenyl having from 3 to 10 carbon atoms, or optionally substituted aryl or heterocyclyl radical;
$R_2$ is an alkyl radical having from 1 to 10 carbon atoms, alkenyl or alkynyl having from 2 to 10 carbon atoms, cycloalkyl or cycloalkenyl having from 3 to 10 carbon atoms, optionally substituted aryl or heterocyclic radical;
$R_3$ is a linker or an optionally substituted aryl or heterocyclic radical, alkyl having from 1 to 10 carbon atoms, alkenyl or alkynyl having from 2 to 10 carbon atoms, cycloalkyl or cycloalkenyl having from 3 to 10 carbon atoms;
$R_4$ is a linker;
$R_5$ and R together form a bond to form a cyclic ether, or $R_7$ and R together form a bond to form a cyclic ether; provided that when $R_5$ and R form a bond, then $R_7$ is H, and provided that when $R_7$ and R form a bond then $R_5$ is H;
$R_6$ is H; and
$R_8$ is optionally substituted aryl or a heterocyclic radical.

35. A compound according to claim 3 wherein $R_2$ is an alkyl group.

36. A compound according to claim 35 wherein $R_2$ is a tert-butyl group.

37. A compound according to claim 4 wherein $R_2$ is an alkyl group.

38. A compound according to claim 37 wherein $R_2$ is a tert-butyl group.

39. A compound according to claim 3 wherein the linkers contain one or more groups selected from the list consisting of disulfide groups, thioether groups, acid labile groups, photolabile groups, peptidase labile groups and esterase labile groups.

40. A compound according to claim 39 wherein the linkers contain one or more groups selected from the list consisting of disulfide groups and thioether groups.

41. A compound according to claim 4 wherein the linkers contain one or more groups selected from the list consisting of disulfide groups, thioether groups, acid labile groups, photolabile groups, peptidase labile groups and esterase labile groups.

42. A compound according to claim 41 wherein the linkers contain one or more groups selected from the list consisting of disulfide groups and thioether groups.

43. A compound according to claim 39 wherein the linkers are thiol- or disulfide-containing, and wherein the side chain carrying the thiol or disulfide group can be linear or branched, aromatic or heterocyclic.

44. A compound according to claim 41 wherein the linkers are thiol- or disulfide-containing, and wherein the side chain carrying the thiol or disulfide group can be linear or branched, aromatic or heterocyclic.

45. A compound according to claim 3 wherein $R_8$ is 3-methoxyphenyl, 3-chlorophenyl, 2,5-dimethoxyphenyl, furyl, pyrollyl, thienyl, thiazolyl, imidazolyl, pyridyl, oxazolyl, indolyl, benzofuranyl or benzothienyl.

46. A compound according to claim 4 wherein $R_8$ is 3-methoxyphenyl, 3-chlorophenyl, 2,5-dimethoxyphenyl, furyl, pyrollyl, thienyl, thiazolyl, imidazolyl, pyridyl, oxazolyl, indolyl, benzofuranyl or benzothienyl.

47. A compound according to claim 3 wherein $R_5$ is H and R and $R_7$ together form a bond.

48. A compound according to claim 4 wherein $R_5$ is H and R and $R_7$ together form a bond.

* * * * *

UNITED STATES PATENT AND TRADEMARK OFFICE
CERTIFICATE OF CORRECTION

| | | |
|---|---|---|
| PATENT NO. | : 7,667,054 B2 | Page 1 of 1 |
| APPLICATION NO. | : 11/295294 | |
| DATED | : February 23, 2010 | |
| INVENTOR(S) | : Miller et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 955 days.

Signed and Sealed this

Seventh Day of December, 2010

David J. Kappos
*Director of the United States Patent and Trademark Office*

UNITED STATES PATENT AND TRADEMARK OFFICE
CERTIFICATE OF CORRECTION

PATENT NO.         : 7,667,054 B2
APPLICATION NO.    : 11/295294
DATED              : February 23, 2010
INVENTOR(S)        : Michael L. Miller et al.

It is certified that error appears in the above-identified patent and that said Letters Patent is hereby corrected as shown below:

In column 2, line 17, delete "calicheamycin" and insert -- calicheamicin --, therefor.

In column 2, line 42, delete "antibotic" and insert -- antibiotic --, therefor.

In column 3, line 19, delete "excipient" and insert -- excipient. --, therefor.

In column 4, line 36, delete "radical" and insert -- radical. --, therefor.

In column 4, line 42, delete "terbutyl" and insert -- tertbutyl --, therefor.

In column 4, line 46, delete "atoms" and insert -- atoms. --, therefor.

In column 5, line 18, delete "radical" and insert -- radical. --, therefor.

In column 5, line 22, delete "radical" and insert -- radical. --, therefor.

In column 5, line 23, delete "pyrollyl," and insert -- pyrrolyl, --, therefor.

In column 5, line 27-28, delete "dimethyacrylyl," and insert -- dimethylacrylyl, --, therefor.

In column 5, line 28, delete "furyl" and insert -- furyl. --, therefor.

In column 5, line 32, delete "atoms" and insert -- atoms. --, therefor.

In column 5, line 35, delete "pyrollyl," and insert -- pyrrolyl, --, therefor.

In column 5, line 37, delete "dimethyacrylyl," and insert -- dimethylacrylyl, --, therefor.

In column 6, line 11, delete "pyrollyl," and insert -- pyrrolyl, --, therefor.

In column 6, line 58, delete "atoms" and insert -- atoms. --, therefor.

In column 6, line 61, delete "pyrollyl," and insert -- pyrrolyl, --, therefor.

In column 6, line 63, delete "bufenyl," and insert -- butenyl, --, therefor.

In column 6, line 63, delete "dimethyacrylyl," and insert -- dimethylacrylyl, --, therefor.

In column 7, line 17, delete "pyrollyl," and insert -- pyrrolyl, --, therefor.

In column 7, line 31, delete "radical" and insert -- radical. --, therefor.

In column 7, line 35, delete "radical" and insert -- radical. --, therefor.

In column 7, line 37, delete "pyrollyl," and insert -- pyrrolyl, --, therefor.

Signed and Sealed this
Twenty-fourth Day of May, 2011

David J. Kappos
*Director of the United States Patent and Trademark Office*

CERTIFICATE OF CORRECTION (continued)

In column 7, line 40-41, delete "dimethyacrylyl," and insert -- dimethylacrylyl, --, therefor.

In column 8, line 24, delete "pyrollyl," and insert -- pyrrolyl, --, therefor.

In column 13-14, 5-7th Structures, delete

"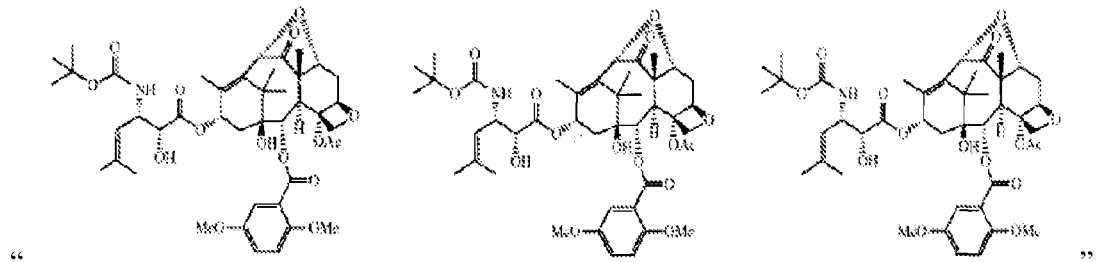"

and insert -- 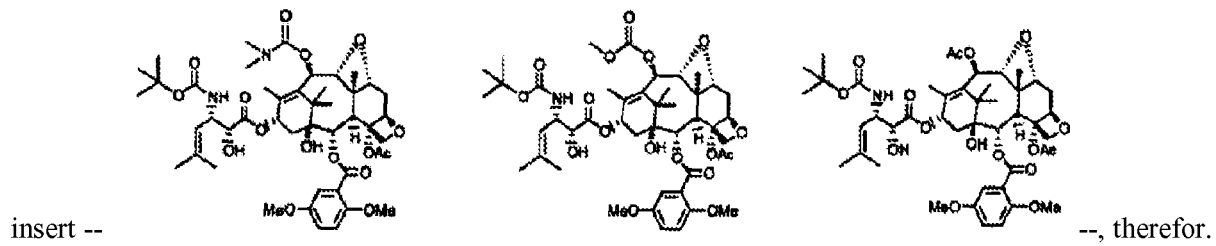 --, therefor.

In column 15, line 39, delete "1.88 s, 3H)" and insert -- 1.88 (s, 3H) --, therefor.

In column 16, line 32, delete "1156.4." and insert -- 1156.4; --, therefor.

In column 17, line 16, delete "1154.4." and insert -- 1154.4; --, therefor.

In column 18, line 18, delete "1008.5." and insert -- 1008.5; --, therefor.

In column 18, line 33, delete "1006.5." and insert -- 1006.5; --, therefor.

In column 19, line 17, delete "850.4." and insert -- 850.4; --, therefor.

In column 20, line 3, delete "852.4." and insert -- 852.4; --, therefor.

In column 20, line 67, delete "1050.5." and insert -- 1050.5; --, therefor.

In column 21, line 67, delete "894.4." and insert -- 894.4; --, therefor.

In column 22, line 67, delete "1066.5." and insert -- 1066.5; --, therefor.

In column 23, line 67, delete "910.4." and insert -- 910.4; --, therefor.

In column 24, line 26, delete "dimethyaminocarbonyloxy" and insert -- dimethylaminocarbonyloxy --, therefor.

In column 24, line 36, delete "carbamyl" and insert -- carbamoyl --, therefor.

In column 24, line 52, delete "dimethyaminocarbonyloxy" and insert -- dimethylaminocarbonyloxy --, therefor.

CERTIFICATE OF CORRECTION (continued)
U.S. Pat. No. 7,667,054 B2

In column 24, line 67, delete "1079.6." and insert -- 1079.6; --, therefor.

In column 25, line 23-24, delete "dimethyaminocarbonyloxy" and insert -- dimethylaminocarbonyloxy --, therefor.

In column 25, line 29, delete "dimethyaminocarbonyloxy" and insert -- dimethylaminocarbonyloxy --, therefor.

In column 26, line 16, delete "dimethyaminocarbonyloxy" and insert -- dimethylaminocarbonyloxy --, therefor.

In column 26, line 27, delete "923.4." and insert -- 923.4; --, therefor.

In column 28, 9th Structure, delete " 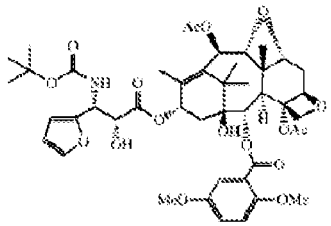 " and insert -- 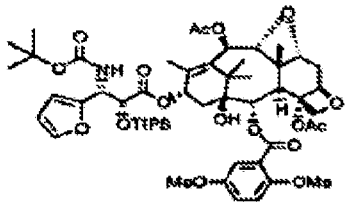 --, therefor.

In column 28, 10th Structure, delete " 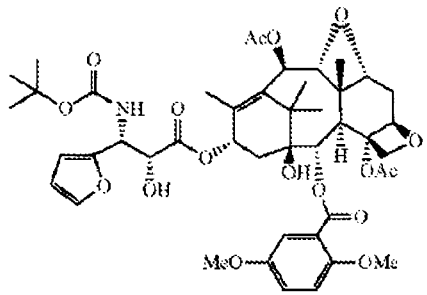 " and insert -- 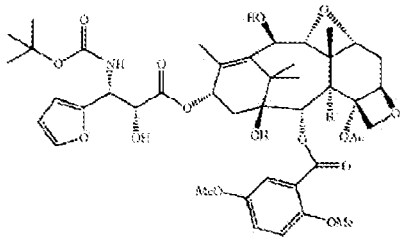 --, therefor.

CERTIFICATE OF CORRECTION (continued)
U.S. Pat. No. 7,667,054 B2

In column 29, line 66, delete "1192.6." and insert -- 1192.6; --, therefor.

In column 30, line 47, delete "1078.5." and insert -- 1078.5; --, therefor.

In column 31, line 26, delete "1036.5." and insert -- 1036.5; --, therefor.

In column 31, line 49, delete "5dimethoxybenzoyl" and insert -- 5-dimethoxybenzoyl --, therefor.

In column 32, line 7, delete "1168.4." and insert -- 1168.4; --, therefor.

In column 32, line 50, delete "supernatent" and insert -- supernatant --, therefor.

In column 32, line 67, delete "1166.4." and insert -- 1166.4; --, therefor.

In column 34, line 6, delete "1020.5." and insert -- 1020.5; --, therefor.

In column 34, line 20, delete "1018.5." and insert -- -1018.5; --, therefor.

In column 35, line 2, delete "862.3." and insert -- 862.3; --, therefor.

In column 35, line 67, delete "864.5." and insert -- 864.5; --, therefor.

In column 36, line 48, delete "1062.5." and insert -- 1062.5; --, therefor.

In column 38, line 9, delete "8.8 Hz 1H)" and insert -- 8.8 Hz, 1H) --, therefor.

In column 38, line 14, delete "906.4." and insert -- 906.4; --, therefor.

In column 41, line 43, delete "methyidithiobutanoyl" and insert -- methyldithiobutanoyl --, therefor.

In column 42, line 8, delete "1156.5." and insert -- 1156.5; --, therefor.

In column 42, line 33-34, delete "methyidithiobutanoyl" and insert -- methyldithiobutanoyl --, therefor.

In column 42, line 65, delete "1000.4." and insert -- 1000.4; --, therefor.

In column 45, line 41, delete "methyidithiobutanoyl" and insert -- methyldithiobutanoyl --, therefor.

In column 45, line 67, delete "1168.5." and insert -- 1168.5; --, therefor.

In column 45, line 67, delete "1168.4" and insert -- 1168.4. --, therefor.

In column 46, line 24-25, delete "methyidithiobutanoyl" and insert -- methyldithiobutanoyl --, therefor.

In column 46, line 49, delete "methyidithiobutanoyl" and insert -- methyldithiobutanoyl --, therefor.

In column 46, line 62, delete "1012.3." and insert -- 1012.3; --, therefor.

In column 55, line 24, delete "antiogen-expreesing" and insert -- antigen-expressing --, therefor.

In column 55, line 29, delete "as." and insert -- as --, therefor.

In column 55, line 37, delete "1 5" and insert -- 15 --, therefor.

In column 56, line 1, delete "methyidithio" and insert -- methyldithio --, therefor.

In column 56, line 14, delete "995.4." and insert -- 995.4; --, therefor.

In column 56, line 61, delete "taxoid" and insert -- taxoid. --, therefor.

In column 63, line 17, in claim 13, delete "pyrollyl" and insert -- pyrrolyl --, therefor.

CERTIFICATE OF CORRECTION (continued)
U.S. Pat. No. 7,667,054 B2

In column 74, line 7, in claim 45, delete "pyrollyl" and insert -- pyrrolyl --, therefor.

In column 74, line 11, in claim 46, delete "pyrollyl" and insert -- pyrrolyl --, therefor.